United States Patent
Ramirez et al.

(10) Patent No.: US 11,667,969 B2
(45) Date of Patent: Jun. 6, 2023

(54) PROTECTIVE SURFACE COATINGS FOR FLOW CELLS

(71) Applicants: ILLUMINA, INC., San Diego, CA (US); ILLUMINA CAMBRIDGE LIMITED, Cambridge (GB); ILLUMINA SINGAPORE PTE. LTD., Helios (SG)

(72) Inventors: Sean M. Ramirez, San Diego, CA (US); Brian D. Mather, San Diego, CA (US); Edwin Li, Los Angeles, CA (US); Sojeong Moon, San Diego, CA (US); Innsu Daniel Kim, San Diego, CA (US); Alexandre Richez, Cambourne (GB); Ludovic Vincent, San Diego, CA (US); Xavier von Hatten, Cambridge (GB); Hai Quang Tran, San Diego, CA (US); Maxwell Zimmerley, San Diego, CA (US); Julia Morrison, Grays (GB); Gianluca Andrea Artioli, Cambridge (GB); Krystal Sly, San Diego, CA (US); Hayden Black, San Diego, CA (US); Lewis J. Kraft, San Diego, CA (US); Hong Xie, Singapore (SG); Wei Wei, San Diego, CA (US); Ryan Sanford, Temecula, CA (US)

(73) Assignees: Illumina, Inc., San Diego, CA (US); Illumina Cambridge Limited, Cambridge (GB); Illumina Singapore Pte. Ltd., Helios (SG)

(*) Notice: Subject to any disclaimer, the term of this patent is extended or adjusted under 35 U.S.C. 154(b) by 464 days.

(21) Appl. No.: 15/969,562

(22) Filed: May 2, 2018

(65) Prior Publication Data
US 2018/0327832 A1 Nov. 15, 2018

Related U.S. Application Data

(60) Provisional application No. 62/504,977, filed on May 11, 2017.

(51) Int. Cl.
*B01L 3/00* (2006.01)
*C12Q 1/6874* (2018.01)
*C12Q 1/6806* (2018.01)

(52) U.S. Cl.
CPC ...... *C12Q 1/6874* (2013.01); *B01L 3/502707* (2013.01); *C12Q 1/6806* (2013.01);
(Continued)

(58) Field of Classification Search
CPC .... B01J 2219/00626; B01J 2219/00722; B01J 2219/0057
(Continued)

(56) References Cited

U.S. PATENT DOCUMENTS 6,589,778 B1 7/2003 Hawkins
8,580,209 B2 11/2013 Kurowski et al.
(Continued)

FOREIGN PATENT DOCUMENTS

CN 103951797 A 7/2014
CN 104039438 A 9/2014
(Continued)

OTHER PUBLICATIONS

International Search Report and Written Opinion for International Application No. PCT/US2018/030689 dated Aug. 29, 2018, 12 pages.

*Primary Examiner* — Natalia Levkovich
(74) *Attorney, Agent, or Firm* — Dierker & Kavanaugh, P, C.

(57) ABSTRACT

An example of a method includes providing a substrate with an exposed surface comprising a first chemical group,
(Continued)

wherein the providing optionally comprises modifying the exposed surface of the substrate to incorporate the first chemical group; reacting the first chemical group with a first reactive group of a functionalized polymer molecule to form a functionalized polymer coating layer covalently bound to the exposed surface of the substrate; grafting a primer to the functionalized polymer coating layer by reacting the primer with a second reactive group of the functionalized polymer coating layer; and forming a water-soluble protective coating on the primer and the functionalized polymer coating layer. Examples of flow cells incorporating examples of the water-soluble protective coating are also disclosed herein.

11 Claims, 16 Drawing Sheets

(52) U.S. Cl.
CPC .................. *B01L 2300/0819* (2013.01); *B01L 2300/0877* (2013.01); *B01L 2300/0887* (2013.01); *B01L 2300/16* (2013.01); *B01L 2300/165* (2013.01)

(58) Field of Classification Search
USPC ............................ 422/552, 82.05, 82.08, 603
See application file for complete search history.

(56) References Cited

U.S. PATENT DOCUMENTS

| | | |
|---|---|---|
| 8,822,346 B1 | 9/2014 | Weiner |
| 2003/0040129 A1 | 2/2003 | Shah |
| 2006/0254916 A1 | 11/2006 | Hernandez et al. |
| 2009/0054264 A1 | 2/2009 | Ugolin et al. |
| 2009/0093064 A1 | 4/2009 | Kolesnychenko |
| 2011/0008776 A1 | 1/2011 | Warthoe et al. |
| 2012/0061014 A1 | 3/2012 | Patel et al. |
| 2013/0116153 A1* | 5/2013 | Bowen ................. C12Q 1/6844 506/16 |
| 2013/0178369 A1 | 7/2013 | Burns et al. |
| 2015/0005447 A1 | 1/2015 | Berti et al. |
| 2015/0259735 A1 | 9/2015 | George et al. |
| 2016/0023208 A1 | 1/2016 | Fisher et al. |

FOREIGN PATENT DOCUMENTS

| | | |
|---|---|---|
| CN | 104508060 A | 4/2015 |
| CN | 104736235 A | 6/2015 |
| CN | 105431554 A | 3/2016 |
| JP | 2007171030 A | 7/2007 |
| KR | 1020150129651 | 11/2015 |
| WO | WO 2014/133905 | 9/2014 |
| WO | 2016/019026 A1 | 2/2016 |
| WO | WO 2016/022266 | 2/2016 |
| WO | 2016/075204 A1 | 5/2016 |
| WO | WO 2017/024271 | 2/2017 |

* cited by examiner

To Fig 5E  To Fig 5I

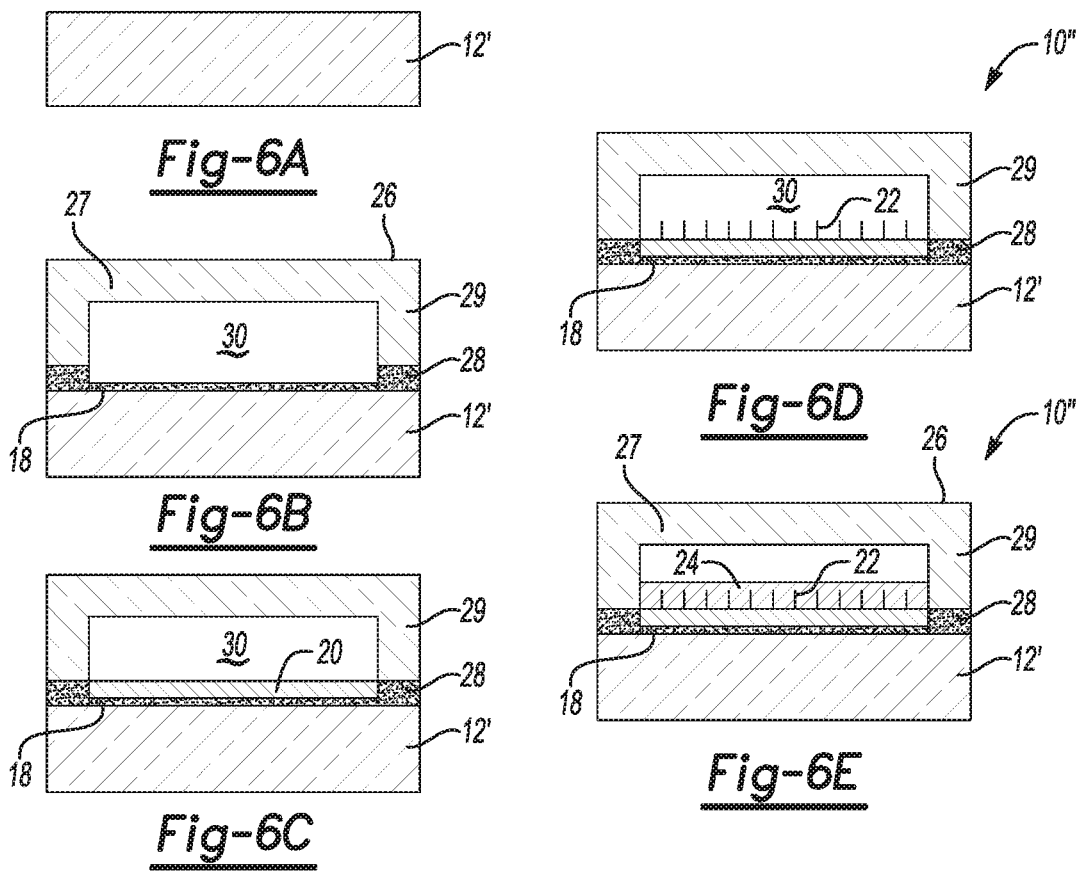
*Fig-6A*
*Fig-6B*
*Fig-6C*
*Fig-6D*
*Fig-6E*
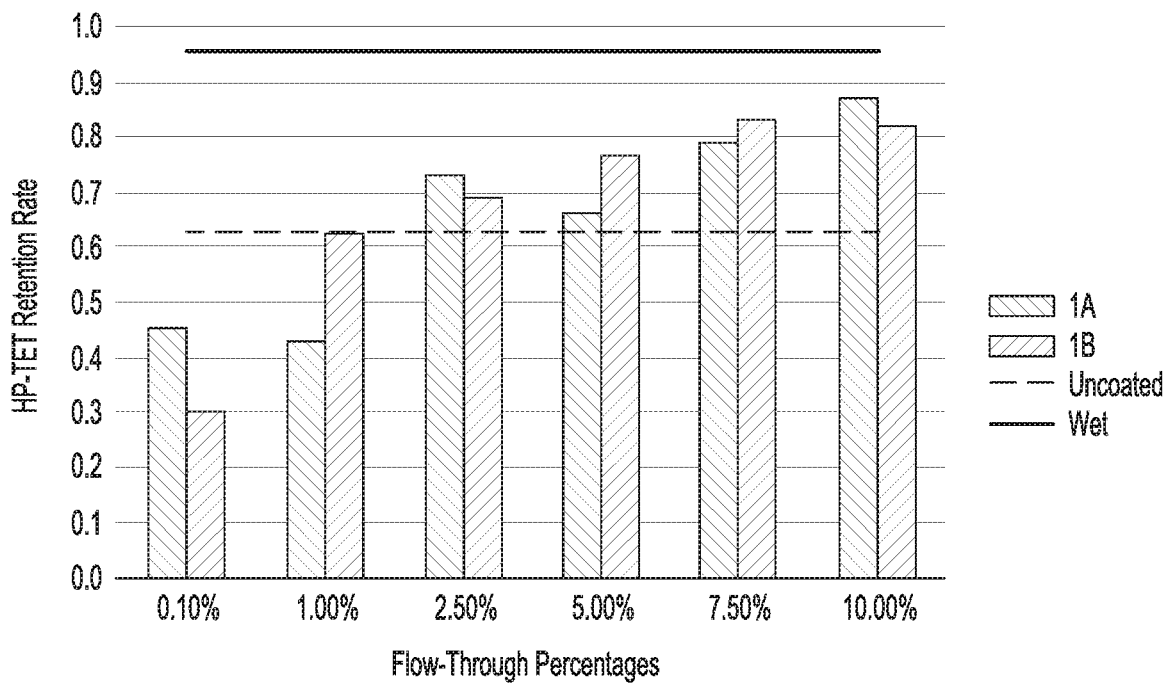
*Fig-7*

PROTECTIVE SURFACE COATINGS FOR FLOW CELLS

CROSS-REFERENCE TO RELATED APPLICATIONS

This application claims priority to U.S. Provisional Application No. 62/504,977, filed May 11, 2017, which is incorporated by reference in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes of humans and other organisms. In certain applications, for example, individual DNA and RNA probes may be attached at small locations in a geometric grid (or randomly) on an array support. A test sample, e.g., from a known person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of bases are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

SUMMARY

In one aspect a flow cell comprises: a substrate, a lid bonded to a bonding region of the substrate wherein the lid and the substrate at least partially define a flow channel, and surface chemistry positioned on the substrate and in the flow channel. A water-soluble protective coating covers the surface chemistry on the substrate.

In one aspect a flow cell comprises: a substrate comprising an exposed surface; a functionalized polymer coating layer covalently bound to the exposed surface of the substrate through a chemical group on the exposed surface; a primer grafted to the functionalized polymer coating layer; and a water-soluble protective coating on the primer and the functionalized polymer coating layer. In some examples, the flow cell further comprises a lid bonded to a bonded region of the substrate, wherein the lid and the substrate at least partially define a flow channel.

In some aspects of the flow cells described herein, the functionalized polymer coating layer is covalently bound to the exposed surface due to reaction of a chemical group on the exposed surface with a first reactive group of the functionalized polymer coating layer. In some examples, the primer is grafted to the functionalized polymer coating layer due to reaction of the primer with a second reactive group of the functionalized polymer coating layer.

An example of a flow cell disclosed herein includes a patterned substrate. The patterned substrate includes depressions separated by interstitial regions, and surface chemistry positioned in the depressions. In some examples, a lid is bonded to a bonding region of the patterned substrate, wherein the lid at least partially defines a flow channel that is in selective communication with the depressions. A water-soluble protective coating covers the surface chemistry in the depressions. In some examples, the chemical group on the exposed surface is attached to the substrate in the depressions.

Another example of a flow cell disclosed herein includes a non-patterned substrate. In some examples, a lid is bonded to a bonding region of the non-patterned substrate, wherein the lid and the non-patterned substrate at least partially define a flow channel including the exposed surface. Surface chemistry is positioned on the non-patterned substrate and in the flow channel. A water-soluble protective coating covers the surface chemistry. In some examples, the chemical group on the exposed surface is attached to the non-patterned substrate.

In another aspect, a method of using a flow cell as described herein comprises: inserting the flow cell into a sequencing instrument; and removing the water-soluble protective coating by exposing the water-soluble protective coating to water (optionally in the form of an aqueous buffer). In some aspects, the removing is done by performing a flow through process to remove the water-soluble protective coating. The removing of the water-soluble protective coating reveals the primer, which can then be used to hybridize to a target oligonucleotide comprising a sequence complementary to at least a portion of the primer.

In an example of a method disclosed herein, surface chemistry is added to a portion of a flow cell substrate, and a water-soluble protective coating is applied on at least the surface chemistry.

In another aspect a method comprises: providing a substrate with an exposed surface comprising a first chemical group, wherein the providing optionally comprises modifying the exposed surface of the substrate to incorporate the first chemical group; reacting the first chemical group with a first reactive group of a functionalized polymer molecule to form a functionalized polymer coating layer covalently bound to the exposed surface of the substrate; grafting a primer to the functionalized polymer coating layer by reacting the primer with a second reactive group of the functionalized polymer coating layer; and forming a water-soluble protective coating on the primer and the functionalized polymer coating layer.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIGS. 5A through 5D and 5I through 5L are cross-sectional views which together illustrate another example of the method shown in FIG. 4;

FIGS. 6A through 6E are cross-sectional views which together illustrate another example of the methods disclosed herein;

FIG. 7 is a bar graph depicting the Hairpin-TET (HP-TET) retention rate for flow cells after storage for 7 days at 30° C. with different examples of the protective coating thereon;

DETAILED DESCRIPTION

Figure 1:
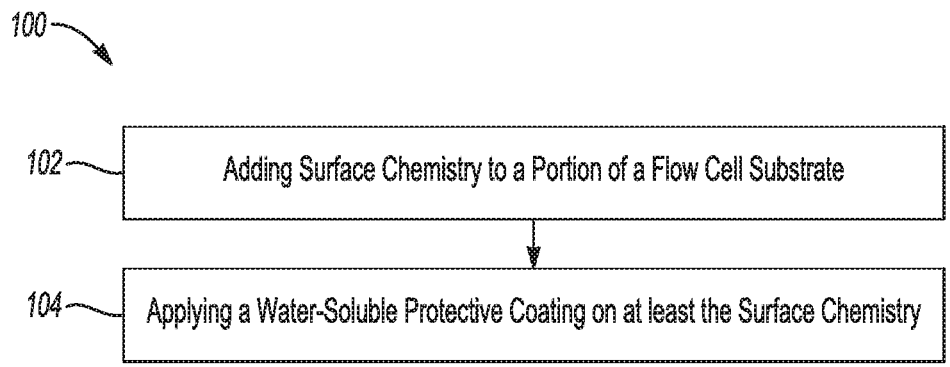
FIG. 1 is a flow diagram illustrating an example of the methods disclosed herein.

A first aspect of a flow cell comprises a patterned substrate, including depressions separated by interstitial regions and surface chemistry (e.g., a functionalized polymer coating layer and a primer grafted thereto) positioned in the depressions; a lid bonded to a bonding region of the patterned substrate, wherein the lid at least partially defines a flow channel that is in selective communication with the depressions; and a water-soluble protective coating covering the surface chemistry in the depressions and at least a portion of the patterned substrate.

In one aspect a flow cell comprises: a substrate comprising an exposed surface; a functionalized polymer coating layer covalently bound to the exposed surface of the substrate; a primer grafted to the functionalized polymer coating layer; and a water-soluble protective coating on the primer and the functionalized polymer coating layer. In some examples, the flow cell further comprises a lid bonded to a bonded region of the substrate, wherein the lid and the substrate at least partially define a flow channel.

In some examples, the functionalized polymer coating layer is covalently bound to the exposed surface due to reaction of a chemical group on the exposed surface with a first reactive group of the functionalized polymer coating layer. In some examples, the primer is grafted to the functionalized polymer coating layer due to reaction of the primer with a second reactive group of the functionalized polymer coating layer. In some examples, the primer comprises an alkynyl group for reaction with the second reactive group. In some examples, the chemical group attached to the exposed surface is an alkenyl, cycloalkenyl, or norbornenyl group. In some examples, the chemical group is part of linker, such as a silane or silane derivative, which is attached to the exposed surface of the substrate.

In some examples, the substrate is a patterned substrate. The patterned substrate includes depressions separated by interstitial regions. In some examples, a lid is bonded to a bonding region of the patterned substrate, wherein the lid at least partially defines a flow channel that is in selective communication with the depressions. In some examples, the water-soluble protective coating covers the functionalized polymer coating layer and the primer in the depressions. In some examples, the chemical group on the exposed surface is attached to the substrate in the depressions, optionally via a linker.

In other examples, the flow cell substrate is a non-patterned substrate. In some examples, a lid is bonded to a bonding region of the non-patterned substrate, wherein the lid and the non-patterned substrate at least partially define a flow channel including the exposed surface. The functionalized polymer coating layer and primer are on the non-patterned substrate and in the flow channel. The water-soluble protective coating covers the functionalized polymer coating layer and primer. In some examples, the chemical group on the exposed surface is attached to the substrate, optionally via a linker. Thus, in some aspects, a flow cell comprises a non-patterned substrate; a lid bonded to a bonding region of the non-patterned substrate, wherein the lid and the non-patterned substrate at least partially define a flow channel; surface chemistry (e.g., functionalized polymer coating layer and primer grafted thereto) positioned on the non-patterned substrate and in the flow channel; and a water-soluble protective coating covering the surface chemistry.

In a first aspect, a method comprises adding surface chemistry to a portion of a flow cell substrate, and applying a water-soluble protective coating on at least the surface chemistry. In an example of this first aspect of the method, adding the surface chemistry involves forming a functionalized polymer coating layer, and grafting a primer to the functionalized polymer coating layer; and the water-soluble protective coating is applied after the primer is grafted. Also in this example of this first aspect, the water-soluble protective coating is patterned to define a bonding region of the flow cell substrate after the water-soluble protective coating is formed; and the method further comprises bonding a lid to the defined bonding region of the flow cell substrate to form a flow channel.

In another example of this first aspect of the method, adding the surface chemistry involves forming a functionalized polymer coating layer, and the water-soluble protective coating is applied after the functionalized polymer coating layer is formed. Also in this example of this first aspect, the water-soluble protective coating is selected from the group consisting of a polyvinyl alcohol/polyethylene glycol graft copolymer, sucrose, polyacrylamide, and polyethylene glycol. Still further in this example of this first aspect, the water-soluble protective coating is patterned to define a bonding region of the flow cell substrate after the water-soluble protective coating is formed; and the method further comprises bonding a lid to the defined bonding region of the flow cell substrate to form a flow channel. After bonding, the method further comprises removing the water-soluble protective coating, thereby exposing the functionalized polymer coating layer and another portion of the substrate; grafting a primer to the functionalized polymer coating layer; and forming a second water-soluble protective coating on the primer, the functionalized polymer coating layer and the other portion of the flow cell substrate. In an example of this aspect, removing the water-soluble protective coating involves a dissolution process. Also in this aspect, the second water-soluble protective coating is selected from the group consisting of a non-cationic synthetic polymer; a natural polysaccharide or a derivative thereof; a natural protein or a derivative thereof; a water-soluble salt; a small molecule compound selected from the group consisting of a water-soluble surfactant, a sugar, an antioxidant, a chelator, a buffer, a glycol, glycerol, and a cyclodextrin; and combinations thereof.

In one aspect is a method wherein a functionalized polymer coating layer is formed on an exposed surface of a substrate. A primer is grafted to the functionalized polymer coating layer. A water-soluble protective coating is formed on the functionalized polymer coating layer. In some examples, the exposed surface comprises a linker (e.g., a silane or a silane derivative) attached thereto. In some aspects, the method comprises attaching the linker (e.g., silane or silane derivative) to the exposed surface. In some aspects, the substrate is non-patterned. In other aspects, the substrate is patterned, and the attaching provides derivatized (e.g., silanized) depressions and derivatized (e.g., silanized) interstitial regions.

In one aspect a method comprises: modifying an exposed surface of a substrate to incorporate a first chemical group; reacting the first chemical group with a first reactive group of a functionalized polymer molecule to form a functionalized polymer coating layer covalently bound to the exposed surface of the substrate; grafting a primer to the functionalized polymer coating layer by reacting the primer with a second reactive group of the functionalized polymer coating layer; and forming a water-soluble protective coating on the primer and the functionalized polymer coating layer.

In another example of a method disclosed herein, the modifying of the exposed surface comprises attaching a linker (e.g., a silane or a silane derivative) to the exposed surface of a substrate. In some examples, the linker (e.g., silane or silane derivative) comprises the first chemical group. In some examples, the linker is a silane or a silane derivative. In some examples, the modifying of the exposed surface comprises plasma ashing. In some examples, the modifying comprises plasma ashing to form a plasma-ashed surface and attaching the linker (e.g., silane or silane derivative) thereto.

In some examples, the substrate is non-patterned. In some examples, the reacting of the first chemical group with the first reactive group of the functionalized polymer molecule forms a functionalized polymer coating layer covalently bound to the exposed surface of the substrate via the linker (e.g., silane or silane derivative). In some examples, after the modifying of the exposed surface, the method further comprises bonding a lid to a bonding region of the non-patterned substrate, wherein the lid and the non-patterned substrate at least partially define a flow channel including some of the exposed surface.

In other examples, the substrate is non-patterned. In some examples, modifying of the exposed surface comprises plasma ashing, and after the modifying of the exposed surface, the method further comprises bonding a lid to a bonding region of the non-patterned substrate, wherein the lid and the non-patterned substrate at least partially define a flow channel including some of the exposed surface.

In some examples, the substrate is a patterned substrate (comprising depressions separated by interstitial regions). In some examples, the functionalized polymer coating layer is formed in the depressions to form functionalized depressions, and the water-soluble protective coating is formed on the functionalized depressions. In some aspects, the chemical group is attached to the substrate in the depressions, and the flow channel is in selective communication with the depressions. In some examples, the water-soluble protective coating is in the depressions and on at least a portion of the interstitial regions.

In some examples, the patterned substrate comprises a linker (e.g., silane or silane derivative) attached to the exposed surface. In some examples, the linker is attached to the exposed surface in the depressions, and in some examples, the linker is attached to the exposed surface in the depressions and interstitial regions, to form derivatized (e.g., silanized) depressions and derivatized (e.g., silanized) interstitial regions. In some examples, the modifying of the exposed surface involves attaching a linker (e.g., silane or a silane derivative) comprising the first chemical group to the exposed surface to form derivatized (e.g., silanized) depressions and, optionally, derivatized (e.g., silanized) interstitial regions. In some examples, the reacting forms the functionalized polymer coating layer in the derivatized (e.g., silanized) depressions and interstitial regions. In some examples, prior to the grafting of the primer, the method further comprises removing the functionalized polymer coating layer from the derivatized (e.g., silanized) interstitial regions. In some examples, the removing is done by polishing the functionalized polymer coating layer from the interstitial regions. A primer is grafted to the functionalized polymer coating layer in the derivatized (e.g., silanized) depressions to form functionalized depressions. In some such examples, the grafting attaches the primer to the functionalized polymer coating layer in the derivatized (e.g., silanized) depressions, thereby forming functionalized depressions. A water-soluble protective coating is formed on the functionalized depressions and at least a portion of the interstitial regions. In some examples, the forming yields the water-soluble protective coating on the functionalized depressions and at least some of the interstitial regions. In some examples, after the removing of the functionalized polymer coating layer, the method further comprises bonding a lid to a bonding region of the patterned substrate, wherein the lid and the non-patterned substrate at least partially define a flow channel including the silanized depressions having the functionalized polymer coating thereon.

Thus, in some examples, the method comprises attaching a silane or a silane derivative to a surface of a patterned substrate including depressions separated by interstitial regions, thereby forming silanized depressions and silanized interstitial regions; forming a functionalized polymer coating layer in the silanized depressions and on the silanized interstitial regions; polishing the functionalized polymer coating layer from the silanized interstitial regions; grafting a primer to the functionalized polymer coating layer in the silanized depressions to form functionalized depressions; and forming a water-soluble protective coating on the functionalized depressions and at least a portion of the interstitial regions.

In some aspects of the method, the water-soluble protective coating is formed after the primer is grafted; the water-soluble protective coating is patterned such that a bonding region of the patterned substrate remains exposed after the water-soluble protective coating is formed; and the method further comprises bonding a lid to the bonding region of the patterned substrate to form a flow channel that is in selective fluid communication with at least some of the functionalized depressions.

In other aspects of the method, after the functionalized polymer coating layer is removed (e.g., by polishing) from interstitial regions of a patterned substrate and before i) the primer is grafted and ii) the water-soluble protective coating is formed, the method further comprises: patterning an initial water-soluble protective coating on the functionalized polymer coating layer such that a bonding region of the patterned substrate remains exposed; bonding a lid to the bonding region of the patterned substrate to form a flow channel that is in selective fluid communication with at least some of the depressions; and removing the initial water-soluble protective coating.

In some examples, the modifying of the exposed surface, the reacting of the first chemical group with the first reactive group, the grafting of the primer, and/or the forming of the water-soluble protective coating involve respective flow through processes. In some examples, the grafting of the primer and the forming of the water-soluble protective coating involve respective flow through processes. In some examples, applying the water-soluble protective coating involves flow through deposition, dip coating, spin coating, spray coating, ultrasonic spray coating, doctor blade coating, aerosol printing, or inkjet printing.

In some examples, the methods further comprise bonding a lid to a bonding region of the flow cell substrate to form a flow channel, and then adding the surface chemistry (e.g., functionalized polymer coating layer and primer) and applying the water-soluble protective coating.

In some examples, following grafting of the primer, the method further comprises at least partially removing the water-soluble protective coating, and performing a dye-based assay to detect any degradation (e.g., loss or loss of function) of the primer.

In some examples, after the functionalized polymer coating layer is formed and before the grafting of the primer and the forming of the water-soluble protective coating, the method further comprises: patterning an initial water-soluble protective coating on the functionalized polymer coating layer such that a bonding region of the substrate remains exposed; bonding a lid to the bonding region of the substrate to form a flow channel that is in selective fluid communication with the initial water-soluble protective coating; and removing the initial water-soluble protective coating. In some examples, the initial water-soluble protecting coating is applied by spray coating or a flow through process. In some examples, the initial water-soluble protective coating and the water-soluble protective coating are formed from the same material, and in other examples, they are formed from different materials.

In some examples, the forming of the water-soluble protective coating involves applying an aqueous solution of a water-soluble material to the exposed surface of the substrate. In some examples, the aqueous solution of the water-soluble material is then dried on the exposed surface (e.g., by warming, heating, evaporation, vacuum exposure, or the like). In some examples, the aqueous solution includes up to about 15%, or about 1 to 15%, or about 1 to 10%, or about 1 to 5%, or about 2 to 5%, or about 4 to 8%, or about 5 to 7.5%, or about 5%, or about 7.5% (mass to volume), of a water-soluble material. In some examples, the aqueous solution comprises about 5 to about 7.5%, or about 5%, or about 7.5% (mass to volume) of a water-soluble material. In some examples, the percentage of the water-soluble material in the aqueous solution is adjusted based on a primer density of the primer. In some examples, the aqueous solution also comprises a co-solvent, such as ethanol. In some examples, the aqueous solution is about 5 to about 7.5%, or about 5%, or about 7.5% of the water-soluble material in 10% aqueous ethanol.

In some examples of the methods and flow cells described herein, the water-soluble protective coating comprises a water-soluble, non-cationic synthetic polymer; a water-soluble natural polysaccharide or a derivative thereof; a water-soluble natural protein or a derivative thereof; a water-soluble salt; or a water-soluble small molecule compound selected from the group consisting of a water-soluble surfactant, a sugar, an antioxidant, a chelator, a buffer, a glycol, glycerol, and a cyclodextrin; or a combination thereof. In some examples, the water-soluble protective coating comprises a water-soluble, non-cationic synthetic polymer. In some examples, the water-soluble protective coating comprises:
(a) the non-cationic synthetic polymer, optionally comprising polyacrylamide, poly(acrylic acid) or polyacrylate (e.g., sodium polyacrylate), poly(methacrylic acid), poly(vinyl pyrrolidone), poly(vinyl alcohol), poly (methacrylamide), a poly(N-alkyl acrylamide), a poly(N-dialkyl acrylamide), poly(N-(2-hydroxypropyl)methacrylamide), poly(divinyl ether-maleic anhydride), a poly(phosphate), a poly(-alkyl-2-oxazoline), poly(hydroxyethyl methacrylate), poly(-hydroxyethyl acrylate), polyethylene glycol, poly(sulfobetaine methacrylate), a polyether (e.g., a polyvinyl ether, polyethylene glycol, poly(ethylene oxide), and the like), poly(vinyl ether-maleic acid), a hydroxyl functional polymer (e.g., PEG or PVA), a non-natural polypeptide (e.g., poly(glutamic acid) or a salt thereof), or a silicone, or a combination thereof; including, for example, random, block and graft copolymers and branched analogues; or
(b) the natural polysaccharide or derivative thereof, optionally selected from the group consisting of starch, carboxymethylcellulose, xanthan gum, pectin, dextran, carrageenan, guar gum, cellulose, hydroxypropylmethyl cellulose (HPMC), hydroxypropyl cellulose (HPC), hydroxyethyl cellulose (HEC), methyl cellulose, carboxymethylhydroxyethyl cellulose (CMHEC), hyaluronic acid, starch phosphate, hydroxypropyl starch, hydroxyethyl starch, agarose, agar, and alginate, and combinations thereof or
(c) the natural protein or derivative thereof optionally selected from casein and albumin; or
(d) the water-soluble salt optionally selected from the group consisting of sodium or potassium salt of chloride, bromide, sulfate, phosphate, carbonate, acetate, and citrate, such as sodium chloride, sodium bromide, sodium sulfate, sodium phosphate, sodium carbonate, sodium acetate, sodium citrate, potassium chloride, potassium bromide, potassium sulfate, potassium phosphate, potassium carbonate, potassium acetate, potassium citrate, or saline sodium citrate, or a combination thereof; or
(e) the buffer (e.g., an aqueous solution of a weak acid and its conjugate base), wherein the weak acid or conjugate base is optionally saline sodium citrate, tris(hydroxymethyl)aminomethane (e.g., Tris or Tris Base) optionally with EDTA, 4-(2-hydroxyethyl)-1-piperazineethanesulfonic acid (HEPES), 3-[[1,3-dihydroxy-2-(hydroxymethyl)propan-2-yl]amino]-2-hydroxypropane-1-sulfonic acid (TAPSO), N-(2-hydroxy-1,1-bis(hydroxymethyl)ethyl) glycine (tricine), 3-(N-morpholino)propanesulfonic acid (MOPS), or 3-(N,N-bis([2-hydroxyethyl]amino)-2-hydroxypropanesulfonic acid (DIPSO); or
(f) the water-soluble surfactant that is optionally an anionic or nonionic surfactant, or that is optionally sodium dodecyl sulfate, an alkyl ethoxylate, an ethoxylated oil, a fat, or a sulfosuccinate; or
(g) the sugar (e.g., sucrose), the antioxidant, the glycol, glycerol, or the cyclodextrin; or
(h) the chelator that is optionally ethylenediaminetetraacetic acid sodium salt, tris(3-hydroxypropyltriazolylmethyl) amine, (tris(2-carboxyethyl)phosphine), or bathophenanthrolinedisulfonic acid disodium salt; or
(i) a combination thereof.

An example of a suitable non-cationic synthetic polymer is a polyvinyl alcohol/polyethylene glycol graft copolymer (one example of which includes KOLLICOAT® IR, available from BASF Corp.). An example of a suitable hydroxyl functional polymer is commercially available from BASF Corp. under the tradename KOLLICOAT® IR. Any of the water-soluble non-cationic synthetic polymers that include acid groups may be used in an alkali metal salt form.

In some of the examples disclosed herein, when applied after primer grafting, the protective coating may be a polyvinyl alcohol/polyethylene glycol graft copolymer (e.g., KOLLICOAT® IR, both available from BASF Corp.), sucrose, dextran (e.g., molecular weight of 200,000 Da), polyacrylamide (e.g., molecular weight of 40,000 Da, 200, 000 Da, etc.), polyethylene glycol, ethylenediaminetetraacetic acid sodium salt (i.e., EDTA), tris(hydroxymethyl) aminomethane with ethylenediaminetetraacetic acid, (tris(2-carboxyethyl)phosphine), tris(3-hydroxypropyltriazolylmethyl)amine, bathophenanthrolinedisulfonic acid disodium salt, hydroxyl functional polymers, glycerol, or saline sodium citrate. In some other of the examples disclosed herein, when applied after or during functionalized polymer coating layer formation, the protective coating may be a polyvinyl alcohol/polyethylene glycol graft copolymer, sucrose, polyacrylamide, or polyethylene glycol. For at least sucrose and polyacrylamide, it is to be understood that the functionalized polymer coating layer should be cured prior to applying the protective coating of these materials.

In some examples, the water-soluble protective coating comprises a non-cationic synthetic polymer; a natural polysaccharide or a derivative thereof; a natural protein or a derivative thereof; a water-soluble salt; a small molecule compound selected from the group consisting of a water-soluble surfactant, a sugar, an antioxidant, a chelator, a buffer, a glycol, glycerol, or a cyclodextrin; or a combination thereof. In some examples, the water-soluble protective coating comprises a polyvinyl alcohol/polyethylene glycol graft copolymer, sucrose, dextran, a polyacrylamide, a glycol, tris(hydroxymethyl)aminomethane or a salt thereof, ethylenediaminetetraacetic acid or a salt thereof, (tris(2-carboxyethyl)phosphine), tris(3-hydroxypropyltriazolylmethyl)amine or a salt thereof, bathophenanthrolinedisulfonic acid disodium salt, a hydroxyl functional polymer, glycerol, or saline sodium citrate, or a mixture thereof. In some examples, the water-soluble protective coating comprises a polyvinyl alcohol/polyethylene glycol graft copolymer, sucrose, or a mixture thereof. In some examples, the water-soluble protective coating comprises a polyvinyl alcohol/polyethylene glycol graft copolymer. In some examples, the graft copolymer comprises about 75% polyvinyl alcohol and about 25% polyethylene glycol.

In some examples of the methods or flow cells described herein, the functionalized polymer coating layer comprises a poly(N-(5-azidoacetamidylpentyl)acrylamide-co-acrylamide (PAZAM).

In some examples of the methods or flow cells described herein, the water-soluble protective coating is present on (or is applied to) the flow cell as a mixture with the functionalized polymer coating layer. In such examples, the flow cell comprises: a substrate comprising an exposed surface; a functionalized polymer coating layer covalently bound to the exposed surface of the substrate; a primer grafted to the functionalized polymer coating layer; and a water-soluble protective coating mixed with the functionalized polymer coating layer. Related methods comprise: modifying an exposed surface of a substrate to incorporate a first chemical group; reacting the first chemical group with a mixture of a water-soluble protective coating and a functionalized polymer molecule comprising a first reactive group to form a functionalized polymer coating layer covalently bound to the exposed surface of the substrate and mixed with the water-soluble protective coating; and grafting a primer to the functionalized polymer coating layer by reacting the primer with a second reactive group of the functionalized polymer coating layer. In such examples, then the functionalized polymer coating layer and water-soluble protecting layer are applied at the same time. In such examples, the functionalized polymer coating layer is cured following application of the mixture of the functionalized polymer molecule and the water-soluble protecting coating. In some examples, the mixture is from 5 wt % to about 95 wt % of the water-soluble coating relative to the functionalized polymer molecule, or about 10 wt % to about 80 wt %, or about 25 wt % to about 75 wt %, or about 25 wt %, 50 wt %, or 75 wt %. The water-soluble protecting coating can protect the surface during the curing step. In some examples, a mixture comprising a water-soluble coating precursor and a functional polymer molecule is applied. In some examples, the mixture further comprises a solvent, such as ethanol. In some examples, the water-soluble coating precursor is KOLLICOAT® IR and the functionalized polymer molecule is PAZAM. In one example, applying a mixture of 5% w/v KOLLICOAT® IR, 0.25% w/v PAZAM, and 5% ethanol in water during the functionalized polymer coating step improved CFR intensity and read 1 cycle 1 intensity, and maintained % passing filter of resulting grafted primers that were loaded at concentrations of 0.8, 1.1, 1.5, and 5 µM, relative to a control (0.25% w/v PAZAM and 5% ethanol in water). In some examples, the mixture is 5% w/v water-soluble coating precursor (e.g., KOLLICOAT® IR), 0.25% w/v functional polymer molecule (e.g., PAZAM), and 5% ethanol. In such examples, the water-soluble coating may remain in place during the primer grafting step. For patterned substrates, the water-soluble coating may be removed during a subsequent polishing step (which employs aqueous conditions), or during rehydration of the flow cell before grafting (the functionalized polymer coating dehydrates during curing).

In some examples of the methods or flow cells described herein, the chemical group incorporated on the exposed surface of the substrate is optionally substituted alkenyl, optionally substituted cycloalkenyl, optionally substituted norbornenyl, optionally substituted cyclooctynyl, optionally substituted bicyclononynyl, optionally substituted alkynyl, azido, optionally substituted tetrazinyl, hydrazonyl, optionally substituted tetrazolyl, formyl, or hydroxyl. In some examples, the chemical group is norbornenyl or substituted norbornenyl. In some examples, the chemical group is covalently linked to the exposed surface of the substrate through a linker. The linker may comprise, for example, alkylene, ethylene glycol, propylene glycol, acetyl, carbonyl, acetamido, amido, silane, silicon, silyl ether, or other spacer units, or a combination thereof. In some examples, the linker comprises a silane or silane derivative, and is referred to herein as a silane linker. In some examples, the silane linker comprises —Si(X)$_2$—C$_{2-6}$alkyl-, wherein each X is —OH, —O-alkyl, or a —O—SiR$_3$ derivative (e.g., a siloxane). In some examples, the linker is —Si(OR)$_2$—CH$_2$—. In some examples, the linker comprises a silyl ether and an alkylene group.

In some examples of the flow cells or methods described herein, the first and second reactive groups are independently optionally substituted alkenyl, optionally substituted cycloalkenyl, optionally substituted norbornenyl, optionally substituted cyclooctynyl, optionally substituted bicyclononynyl, optionally substituted alkynyl, azido, optionally substituted tetrazinyl, hydrazonyl, optionally substituted tetrazolyl, formyl, or hydroxyl. In some examples, the first and second reactive groups are the same. In some examples, the first and second reactive groups are both azido.

In some examples of the flow cells or methods described herein, the primer is modified at one terminus with a moiety for reaction with the second reactive group. For example, the primer comprises an alkynyl group for reaction with the second reactive group.

In some examples of the flow cells or methods described herein, the primer is a plurality of primers that includes two populations of functional primers. In some examples, the primer is a population of functional primers (which may include two subpopulations of functional primers, e.g., Primer A and Primer B) and a population of non-functional primers. In some aspects, the primer comprises a primer sequence. Where two subpopulations of functional primers are used, they include different primer sequences. A target oligonucleotide is hybridized to the primer (via a sequence complementary to the primer sequence), and the primer is extended in the presence of a polymerase to form a complementary copy of the target oligonucleotide that is bound to the substrate.

It is to be understood that any features of the flow cells and of the methods of making the flow cells described herein may be combined together in any desirable manner and/or configuration. Moreover, it is to be understood that any combination of features from any of the methods and/or from the flow cells may be used together, and/or that any features from any or all of these aspects may be combined with any of the features of the examples disclosed herein.

Examples of the method disclosed herein involve the application of a protective coating during flow cell manufacturing workflows. The protective coating may be applied directly on chemically and/or biologically active surface chemistry (e.g., a functionalized polymer coating layer, a primer) that is deposited on a substrate. The protective coating may protect the surface chemistry during subsequent processing techniques (e.g., assembly techniques, such as lid bonding, wafer dicing, etc.) and/or during shipping of the flow cell and/or during short and/or long term storage of the flow cell. In an example, the storage period may be up to 120 days, or longer. In another example, the storage period may range from about 1 day to about 75 days. In another example, the storage period may range from about 1 day to about 2 years, or may be about 12 months, 18 months, or 24 months. While examples have been provided, it is to be understood that the storage period may range from any time after the protective coating has been applied until it is desirable to use the flow cell. As an example, the protective coating may protect the surface chemistry from chemical or physical degradation, e.g., from debris and/or contamination that may otherwise contact the surface chemistry during lid bonding or other assembly processes. As another example, the protective coating may protect the surface chemistry from scratches or other handling related defects that may result during shipping. As still another example, the protective coating may protect the surface chemistry from environmental factors (e.g., temperature, humidity, etc.) during manufacturing, shipping, and/or short and/or long term storage (e.g., at a temperature ranging from about 4° C. to about 80° C., or in some instances lower temperatures, down to about −25° C.). The protective coating helps to maintain the inherent stability of the surface chemistry, and thus improves the shelf life, temperature tolerance, durability, and ambient storage capability of the flow cell. The stabilization of the surface chemistry is an efficient process and the surface chemistry is then stable over time.

The method(s) disclosed herein may be performed entirely at the wafer level, entirely at the die level, in part at the wafer level, and/or in part at the die level. As an example of performing the method partially at the wafer and die levels, the method may be initiated using a wafer, which is then diced to form several dies, and the method may continue using each of the dies. The ability to perform open wafer processing (e.g., chemical or physical steps undertaken prior to lid bonding), at least in some examples, enables a variety of metrology/analytical techniques to be used for quality control and characterization. Prior to being bonded to form a flow cell, the patterned and surface modified wafer/substrate may be exposed to, for example, atomic force microscopy (AFM), scanning electron microscopy (SEM), ellipsometry, goniometry, scatterometry, and/or fluorescence techniques. Alternatively, the bonded flow cell may be exposed to these techniques. At the die level, the method(s) may be performed on an open faced die, or on an assembled flow cell (with an enclosed flow channel).

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc., are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like. The alkenyl group may be designated as, for example, "C2-4 alkenyl," which indicates that there are two to four carbon atoms in the alkenyl chain.

As used herein, "alkynyl" refers to a straight or branched hydrocarbon chain containing one or more triple bonds. The alkynyl group may have 2 to 20 carbon atoms. The alkynyl group may be designated, for example, as "C2-4 alkynyl," which indicates that there are two to four carbon atoms in the alkynyl chain.

An "amino" functional group refers to an —$NR_aR_b$ group, where $R_a$ and $R_b$ are each independently selected from hydrogen, C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, which may be designated as C6-18. Examples of aryl groups include phenyl, naphthyl, azulenyl, and anthracenyl.

As used herein, the term "attached" refers to the state of two things being joined, fastened, adhered, connected or bound to each other. For example, a nucleic acid can be attached to a functionalized polymer coating layer by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to —$N_3$.

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms (i.e., C3-20). Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to —C(O)OH.

As used herein, "cycloalkyl" means a fully saturated carbocyclyl ring or ring system. Examples include cyclopropyl, cyclobutyl, cyclopentyl, and cyclohexyl.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornene or norbornenyl. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "depositing," as used herein, refers to any suitable application technique, which may be manual or automated, and results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, inkjet printing, or the like. In some aspects, the water-soluble protective coating is applied by spray coating. In other aspects, the water-soluble protecting coating is applied by flow through coating.

As used herein, the term "depression" refers to a discrete concave feature in a patterned substrate having a surface opening that is completely surrounded by interstitial region(s) of the patterned substrate surface. Depressions can have any of a variety of shapes at their opening in a surface including, as examples, round, elliptical, square, polygonal, hexagonal, star shaped (with any number of vertices), etc. The cross-section of a depression taken orthogonally with the surface can be curved, square, polygonal, hyperbolic, conical, angular, etc. As an example, the depression can be a well. Also as used herein, a "functionalized depression" refers to the discrete concave feature where the functionalized polymer coating layer and primer(s) are attached.

The term "each," when used in reference to a collection of items, is intended to identify an individual item in the collection, but does not necessarily refer to every item in the collection. Exceptions can occur if explicit disclosure or context clearly dictates otherwise.

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like, in the chamber.

As used herein, a "flow channel" may be an area defined between two bonded components, which can selectively receive a liquid sample. In some examples, the flow channel may be defined between a patterned substrate and a lid, and thus may be in fluid communication with one or more depressions defined in the patterned substrate. In other examples, the flow channel may be defined between a non-patterned substrate and a lid.

The "functionalized polymer coating layer" referred to herein is intended to mean a semi-rigid material that is permeable to liquids and gases. The functionalized polymer coating layer may be a hydrogel that can swell when liquid (e.g., water) is taken up and that can contract when liquid is removed by drying. Typically, while a hydrogel may absorb water, it is not water-soluble. In an example, the functionalized polymer coating layer is poly(N-(5-azidoacetamidylpentyl) acrylamide-co-acrylamide) (PAZAM). The functionalized polymer coating layer may also include other molecules, which include one or more functional groups selected from the group consisting of optionally substituted alkenyl, azide/azido, optionally substituted amino, carboxyl, optionally substituted hydrazone, optionally substituted hydrazine, hydroxyl, optionally substituted tetrazole, optionally substituted tetrazine, nitrile oxide, nitrone, or thiol. In some aspects, the functional groups are reactive groups that are used to attach the functionalized polymer coating layer with the substrate surface and/or the primer to form a covalent bond between these components.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). The heterocyclyl group may be designated as "3-6 membered heterocyclyl" or similar designations. In some examples, the heteroatom(s) are O, N, or S.

The term "hydrazine" or "hydrazinyl" as used herein refers to a —NHNH$_2$ group.

As used herein, the term "hydrazone" or "hydrazonyl" as used herein refers to a

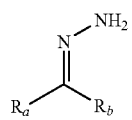

group in which R$_a$ and R$_b$ are defined herein.

As used herein, "hydroxy" or "hydroxyl" refers to an —OH group.

As used herein, the term "interstitial region" refers to an area in a substrate or on a surface that separates depressions. For example, an interstitial region can separate one feature of an array from another feature of the array. The two features that are separated from each other can be discrete, i.e., lacking physical contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. The separation provided by an interstitial region can be partial or full separation. Interstitial regions may have a surface material that differs from the surface material of the features defined in the surface. For example, features of an array can have an amount or concentration of the coating layer and primer(s) that exceeds the amount or concentration present at the interstitial regions. In some examples, the coating layer and primer(s) may not be present at the interstitial regions.

"Nitrile oxide," as used herein, means a "R$_a$C≡N$^+$O$^-$" group in which R$_a$ is defined herein. Examples of preparing nitrile oxide include in situ generation from aldoximes by treatment with chloramide-T or through action of base on imidoyl chlorides [RC(C1)=NOH].

"Nitrone," as used herein, means a "R$_a$R$_b$C=NR$_c^+$O$^-$" group in which R$_a$ and R$_b$ are defined herein and R$_c$ is selected from C1-6 alkyl, C2-6 alkenyl, C2-6 alkynyl, C3-7 carbocyclyl, C6-10 aryl, 5-10 membered heteroaryl, and 5-10 membered heterocyclyl, as defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The term "open wafer processing," as used herein, refers to a series of sequential processes used to modify the surface of a substrate wafer with surface chemistry and protective coating, prior to any assembly (e.g., bonding) process.

The term "flow cell substrate" or "substrate" refers to a support upon which the surface chemistry may be added. The term "patterned substrate" refers to a support in which or on which depressions are defined. The term "non-patterned substrate" refers to a substantially planar support. The substrate may be a wafer, a panel, a rectangular sheet, a die, or any other suitable configuration. The substrate is generally rigid and is insoluble in an aqueous liquid. The substrate may be inert to a chemistry that is used to modify the depressions. For example, a substrate can be inert to chemistry used to form the functionalized polymer coating layer, to form the protective coating, to attach the primer(s) to the functionalized polymer coating layer, etc. Examples of suitable substrates include epoxy siloxane, complementary metal-oxide semiconductor (CMOS) materials, silsesquioxane (e.g., polyhedral silsesquioxanes or POSS materials), glass (such as EAGLE XG® glass from Corning) and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials, aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The substrate may also be glass or silicon, with a coating layer of tantalum oxide or another ceramic oxide at the surface. The substrate may be rigid or flexible.

As used herein, "plasma ashing" refers to a process of removing organic matter from a substrate by an oxygen plasma. The products that result from plasma ashing may be removed with a vacuum pump/system. Plasma ashing can activate the substrate by introducing reactive hydroxyl groups. In some aspects, the linker groups may then be attached to the hydroxyl groups.

As used herein, the "primer" is defined as a single stranded nucleic acid sequence (e.g., single strand DNA or single strand RNA) that serves as a starting point for DNA or RNA synthesis. The 5' terminus of the primer may be modified to allow a coupling reaction with the functionalized polymer coating layer. In some aspects, the 5' terminus of the primer is modified with an alkyne group. The primer length can be any number of bases long and can include a variety of non-natural nucleotides. In an example, the sequencing primer is a short strand, ranging for example, from 20 to 40 bases. In some aspects, the primer is applied to the substrate in a solution at a concentration (referred to herein as "primer density") of from about 5 to 50 µM, or about 10 to 40 µM, or about 15 to 30 µM. The "primer density" as used herein is not a measurement of on-surface grafted primers, but is an inferred density based on the concentration of primer in the grafting mixture. In some aspects, the primer density is from about 1 to about 20 µM (primers grafted onto the surface using a 1-20 µM primer solution). In some aspects, the primer is a mixture of functional primer (capable of serving as a starting point for oligonucleotide synthesis) and a non-functional primer. Non-functional primers are oligonucleotides that do not function as primers, such as truncated primer sequences or short oligonucleotide sequences tagged with detectable, optionally cleavable, labels. Non-functional primers allow for independent (separate) control of the total oligonucleotide/primer density as well as the functional primer density on the grafted substrate. In some examples, the primer density is 12 µM primer and 6 µM non-functional primer (e.g., an oligonucleotide with a quality control tracer attached thereto). In some examples, total primer density is about 18 µM. In some examples, total primer density is about 22 µM. Grafted primers may be present on the surface from about 10,000 to about 50,000, or about 25,000 primers per square micrometer.

As used herein, the term "protective coating" refers to a water-soluble material in the form of a solid (e.g., a thin film), a liquid, or a gel that is applied on the surface chemistry, for example in a depression of a patterned substrate or on flow channel area(s) of an at least substantially planar substrate (i.e., a non-patterned substrate). The protective coating may be any water-soluble material that does not deleteriously affect the underlying surface chemistry or substrate and that serves to protect and/or preserve the functionality of the surface chemistry. A water-soluble protective coating is, by definition, distinguishable from a hydrogel, as the protective coating dissolves when exposed to water, and maybe washed away in this manner, while a hydrogel is water-insoluble. For example, the protective coating may swell the functionalized layer and at least substantially prevent the layer from undergoing deleterious changes during processing and/or shipping and/or storage. For another example, the protective coating may preserve the accessibility of the primer and at least substantially prevent degradation of the functionalized layer.

While several examples have been provided, it is to be understood that other water-soluble, non-cationic synthetic polymers and small molecules may be used to form the protective coating, as long as the selected material does not deleteriously affect the underlying surface chemistry or substrate. Moreover, it may also be desirable to select a material that can readily be removed, that does not interfere with subsequently performed process(es) (e.g., primer attachment, washing, etc.), and/or does not interfere with subsequently performed sequencing technique(s). In an example, the protective coating is not an auto-fluorescent material.

In an example, the thickness or depth of the water-soluble protective coating is at least about 25 nm. In an example, the thickness or depth of the water-soluble protective coating ranges from about 50 nm to about 100 nm. In another example, the thickness or depth of the water-soluble protective coating ranges from about 1 µm to about 15 µm. In yet another example, the thickness or depth of the water-soluble protective coating ranges from about 1.5 µm to about 12 µm. The upper limit on the thickness may depend, at least in part, upon the architecture and dimensions of the flow channel and the flow cell that is formed. In an example, the upper end of the thickness range may range from about 10 µm to about 15 µm.

As used herein, the terms "silane" and "silane derivative" refer to an organic or inorganic compound containing one or more silicon atoms. An example of an inorganic silane compound is $SiH_4$, or halogenated $SiH_4$ where hydrogen is replaced by one or more halogen atoms. An example of an organic silane compound is $X—R^B—Si(OR^C)_3$, wherein X is a nonhydrolyzable organic group, such as amino, vinyl, epoxy

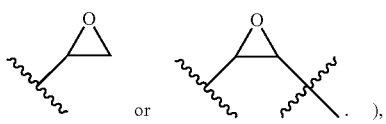

methacrylate, sulfur, alkyl, alkenyl, alkynyl; $R^B$ is a spacer, for example —$(CH_2)_n$—, wherein n is 0 to 1000; $R^C$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the terms "silane" and "silane derivative" can include mixtures of different silane and/or silane derivative compounds.

In some examples, the silane or silane derivative includes an unsaturated moiety that is capable of reacting with a functional group of the functionalized polymer coating layer. As used herein, the term "unsaturated moiety" refers to a chemical group which includes cycloalkenes, cycloalkynes, heterocycloalkenes, heterocycloalkynes, or optionally substituted variants thereof including at least one double bond or one triple bond. The unsaturated moieties can be mono-valent or di-valent. When the unsaturated moiety is mono-valent, cycloalkene, cycloalkyne, heterocycloalkene, and heterocycloalkyne are used interchangeably with cycloalkenyls, cycloalkynyls, heterocycloalkenyl, and heterocycloalkynyl, respectively. When the unsaturated moiety is di-valent, cycloalkene, cycloalkyne, heterocycloalkene, and heterocycloalkyne are used interchangeably with cycloalkenylene, cycloalkynylene, heterocycloalkenylene, and heterocycloalkynylene, respectively.

The unsaturated moiety can be covalently attached either directly to the silicon atoms of the silane or silane derivative, or indirectly attached via linkers. Examples of suitable the linkers include optionally substituted alkylenes (i.e., bivalent saturated aliphatic radicals (such as ethylene) regarded as being derived from an alkene by opening of the double bond or from an alkane by removal of two hydrogen atoms from different carbon atoms), substituted polyethylene glycols, or the like.

A "spacer layer," as used herein refers to a material that bonds two components together. In some examples, the spacer layer can be a radiation-absorbing material that aids in bonding, or can be put into contact with a radiation-absorbing material that aids in bonding.

The term "surface chemistry," as used herein refers to chemically and/or biologically active component(s) that are incorporated into the chamber of the flow cell. Examples of the surface chemistry disclosed herein include the functionalized polymer coating layer attached to at least a portion of a surface of the substrate and/or and the primer(s) attached to at least a portion of the functionalized polymer coating layer.

A "thiol" functional group refers to —SH.

As used herein, the terms "tetrazine" and "tetrazinyl" refer to a six-membered heteroaryl group comprising four nitrogen atoms. Tetrazine can be optionally substituted.

"Tetrazole," as used herein, refers to a five-membered heterocyclic group including four nitrogen atoms. Tetrazole can be optionally substituted.

As used herein, the term "YES method" refers to a chemical vapor deposition process developed by Illumina, Inc. which uses the chemical vapor deposition tool provided by Yield Engineering Systems ("YES"). The tool includes three different vapor deposition systems. The automated YES-VertaCoat silane vapor system is designed for volume production with a flexible wafer handling module that can accommodate 200 mm or 300 mm wafers. The manual load YES-1224P Silane Vapor System is designed for versatile volume production with its configurable large capacity chambers. Yes-LabKote is a low-cost, tabletop version that is ideal for feasibility studies and for R&D.

The aspects and examples set forth herein and recited in the claims can be understood in view of the above definitions.

Examples of the flow cell including the protective coating and methods for making and using the same will now be described in reference to the figures.

An example of the method 100 is depicted in FIG. 1. The method 100 includes adding surface chemistry to a portion of a substrate (as shown at reference numeral 102), and applying a water-soluble protective coating at least on the surface chemistry (as shown at reference numeral 104). In an example, the method 100 includes adding surface chemistry to a portion of a flow cell substrate, wherein the surface chemistry is a sequencing primer, or a functionalized polymer coating layer to attach the sequencing primer, or the sequencing primer and the functionalized polymer coating layer; and applying a water-soluble protective coating on at least the surface chemistry. Two examples of the method 100 are shown in FIG. 2, as methods 100' and 100".

Figure 2:
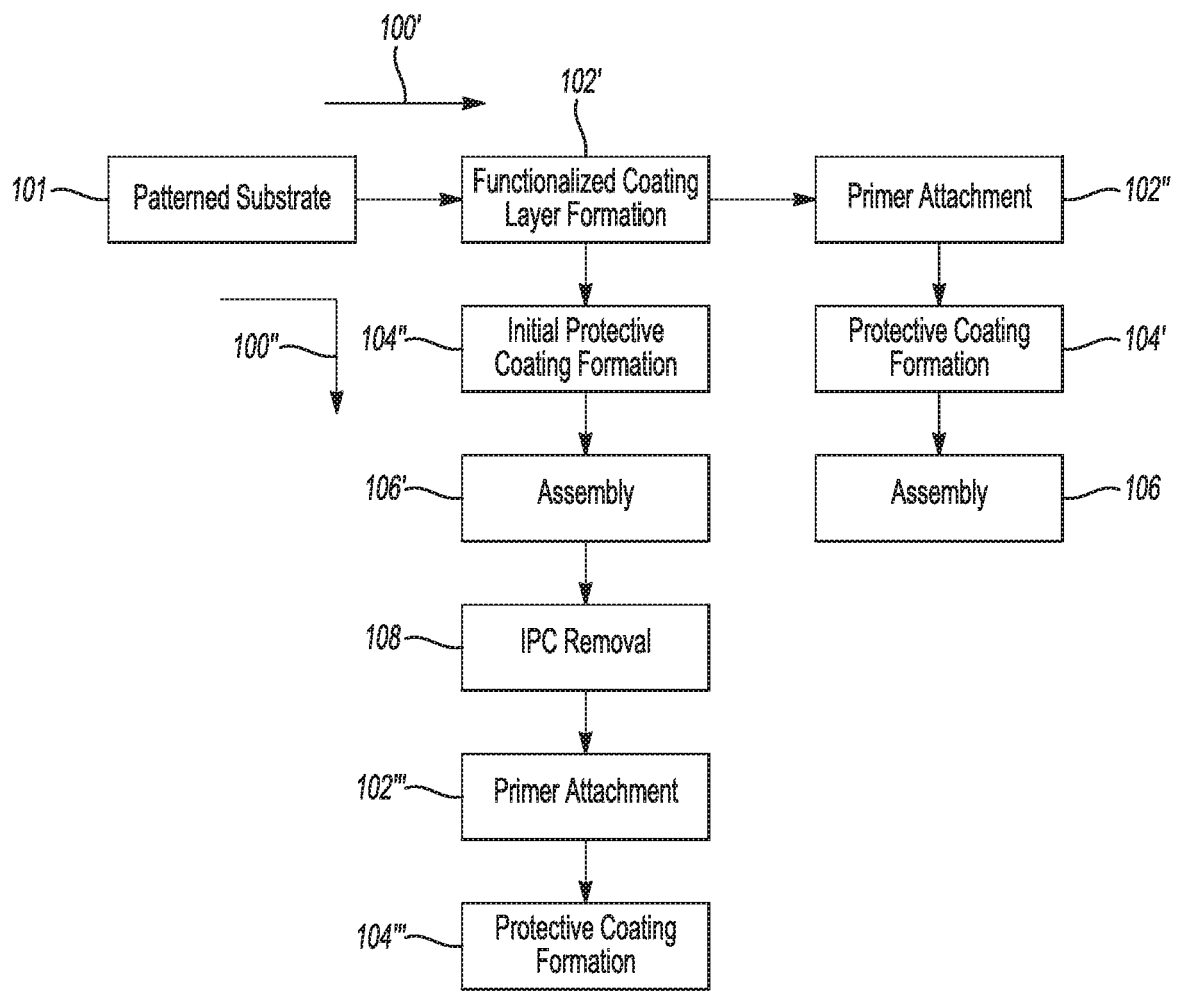
FIG. 2 is a flow diagram illustrating more detailed examples of the method shown in FIG. 1.

The methods 100', 100" may involve the patterned substrate, as shown at reference numeral 101 in FIG. 2, or a non-patterned substrate. Another example of the method 100 involving the non-patterned substrate 12' is further described in reference to FIGS. 6A through 6E. The patterned substrate may be a patterned wafer or a patterned die or any of the other patterned substrates disclosed herein. Any example of the substrate described herein may be used. The patterned substrate (shown as at reference numeral 12 in FIG. 3) includes depressions defined on or in an exposed layer or surface of the substrate, and interstitial regions separating adjacent depressions. The depressions may be fabricated in or on the substrate using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the substrate. Many different layouts of the depressions may be envisaged, as is discussed below in reference to FIG. 5A.

While not shown in FIG. 2, prior to adding the surface chemistry, each of the methods 100', 100" may involve exposing the patterned substrate to a cleaning process and/or to another process that prepares the surface (e.g., depressions and, in some instances, adjacent interstitial regions) of the patterned substrate for the subsequent deposition of the surface chemistry. Examples of the cleaning process and surface preparation process(es) are discussed further below in reference to FIGS. 4 and 5A through 5L.

In the example method 100', the surface chemistry may be both the functionalized polymer coating layer and the primer(s), and a single protective coating may be used. In this example, adding the surface chemistry involves forming the functionalized polymer coating layer in the depression(s) (reference numeral 102') and grafting the primer to the functionalized polymer coating layer (reference numeral 102"), and the water-soluble protective coating is formed after the primer is grafted (reference numeral 104').

At reference numeral 102' in method 100', functionalized polymer coating layer formation takes place. An example of the functionalized polymer coating layer includes a recurring unit of Formula (I):

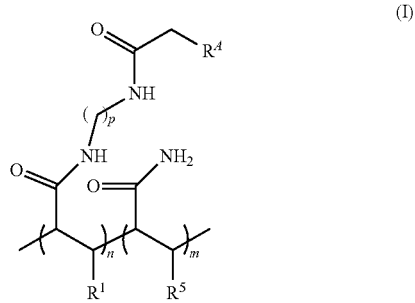

wherein:
$R^1$ is H or optionally substituted alkyl;
$R^4$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^5$ is selected from the group consisting of H and optionally substituted alkyl;
each of the $-(CH_2)_p-$ can be optionally substituted;
p is an integer in the range of 1 to 50;
n is an integer in the range of 1 to 50,000; and
m is an integer in the range of 1 to 100,000.
In the structure of Formula (I), one of ordinary skill in the art will understand that the "n" and "m" subunits are recurring subunits that are present in a random order throughout the polymer.

A particular example of a functionalized polymer coating layer is poly(N-(5-azidoacetamidylpentyl) acrylamide-co-acrylamide, PAZAM (see for example, U.S. Patent Publication Nos. 2014/0079923 A1, or 2015/0005447 A1, each of which is incorporated herein by reference in its entirety), which comprises the structure shown below:

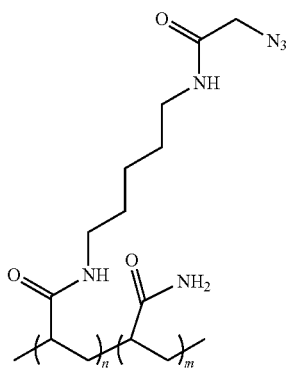

wherein n is an integer in the range of 1-20,000, and m is an integer in the range of 1-100,000. As with Formula (I), one of ordinary skill in the art will recognize that the "n" and "m" subunits are recurring units that are present in random order throughout the polymer structure.

The molecular weight of the Formula (I) or PAZAM polymer may range from about 10 kDa to about 1500 kDa, or may be, in a specific example, about 312 kDa.

In some examples, the Formula (I) or PAZAM polymer is a linear polymer. In some other examples, the Formula (I) or PAZAM polymer is a lightly cross-linked polymer. In other examples, the Formula (I) or PAZAM polymer comprises branching.

Other examples of suitable polymer materials include those having a colloidal structure, such as agarose; or a polymer mesh structure, such as gelatin; or a cross-linked polymer structure, such as polyacrylamide polymers and copolymers, silane free acrylamide (SFA, see, for example, U.S. Patent Publication No. 2011/0059865, which is incorporated herein by reference in its entirety), or an azidolyzed version of SFA. Examples of suitable polyacrylamide polymers may be formed from acrylamide and an acrylic acid or an acrylic acid containing a vinyl group as described, for example, in WO 2000/031148 (incorporated herein by reference in its entirety) or from monomers that form [2+2] photo-cycloaddition reactions, for example, as described in WO 2001/001143 or WO 2003/0014392 (each of which is incorporated herein by reference in its entirety). Other suitable polymers are co-polymers of SFA and SFA derivatized with a bromo-acetamide group (e.g., BRAPA), or co-polymers of SFA and SFA derivatized with an azido-acetamide group.

It is to be understood that other functionalized molecules may be used to form the functionalized polymer coating layer, as long as they are functionalized to interact with the patterned substrate and the subsequently applied primer(s). Other examples of suitable molecules for forming the functionalized polymer coating layer include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions.

The functionalized polymer molecule (e.g., PAZAM) may be deposited on the surface of the patterned substrate using spin coating, or dipping or dip coating, or flow of the functionalized molecule under positive or negative pressure, or other suitable techniques. The functionalized molecule may be present in a solution. In an example, the solution includes PAZAM in an ethanol and water mixture. In some aspects, the functionalized polymer molecule is applied to the substrate prior to complete polymerization, and polymerization to form the coating is done on the substrate surface.

After being coated, the functionalized molecule may also be exposed to a curing process to form the functionalized polymer coating layer across the entire patterned substrate (i.e., on depression(s) and interstitial region(s)). In an example, curing the functionalized molecule may take place at a temperature ranging from room temperature (e.g., about 25° C.) to about 60° C. for a time ranging from about 5 minutes to about 2 hours. In some instances, the functionalized polymer coating layer is cured prior to the application of the protective coating.

To form the functionalized polymer coating layer in the depression(s) and not on the interstitial region(s) of the patterned substrate, the functionalized polymer coating layer may be polished off of the interstitial regions using i) a basic, aqueous slurry having a pH ranging from about 7.5 to about 11 and including an abrasive particle or ii) a polishing pad and a solution free of the abrasive particle.

In this example of the method 100', the primer is then grafted to the functionalized polymer coating layer remaining in the depression(s), as shown as primer attachment at reference numeral 102". Examples of suitable primers include forward amplification primers or reverse amplification primers. Specific examples of suitable primers include P5 or P7 primers, which are used on the surface of commercial flow cells sold by Illumina Inc. for sequencing on HiSeq™, HiSeqX™, MiSeq™, MiSeqX™, NextSeq™ NovaSeq™, Genome Analyzer™, and other instrument platforms.

Grafting may be accomplished by dunk coating, spray coating, puddle dispensing, or by another suitable method that will attach the primer(s) to the functionalized polymer coating layer in at least some of the depressions. Each of these example techniques may utilize a primer solution or mixture, which may include the primer(s), water, a buffer, and a catalyst.

Dunk coating may involve submerging the patterned substrate (having the functionalized polymer coating layer in the depression(s) thereof) into a series of temperature controlled baths. The baths may also be flow controlled and/or covered with a nitrogen blanket. The baths may include the primer solution or mixture. Throughout the various baths, the primer(s) will attach to the functionalized polymer coating layer in at least some of the depression(s). In an example, the coated and polished patterned substrate will be introduced into a first bath including the primer solution or mixture where a reaction takes place to attach the primer(s), and then the patterned substrate will be moved to additional baths for washing. The patterned substrate may be moved from bath to bath with a robotic arm or manually. A drying system may also be used in dunk coating.

Spray coating may be accomplished by spraying the primer solution or mixture directly onto the coated and polished patterned substrate. The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the coated and polished patterned substrate. The applied primer solution or mixture may be applied to or spread across the entire surface of the coated and polished patterned substrate. The primer coated patterned substrate may be incubated for a time ranging from about 2 minutes to about 60 minutes at a temperature ranging from about 0° C. to about 80° C. After incubation, the primer solution or mixture may be diluted and removed using, for example, the spin coater.

In one example, after the primer is grafted to the functionalized polymer coating layer in the depression(s), this example of the method 100' further includes applying the water-soluble protective coating on the surface chemistry and on at least a portion of the substrate (as shown as protective coating formation at reference numeral 104'). In another example, the primer solution or mixture may include a water-soluble, film forming material that forms the protective coating, and thus simultaneous primer grafting and protective coating formation may take place.

When primer grafting and protective coating formation are separate processes, the water-soluble protective coating may be selectively deposited, or patterned, such that the surface chemistry (in this example the functionalized coating layer and the primer(s) thereon) is covered and such that a bonding region of the patterned substrate remains exposed. The bonding region of the patterned substrate is generally located on some of the interstitial region(s) of the patterned substrate where a lid will be bonded to the patterned substrate. When the patterned substrate is a wafer, the bonding region may define the boundaries of several flow cells that are being formed from the wafer. When the patterned substrate is a die, the bonding region may define the outer boundaries of one flow cell that is being formed. It is to be understood that other portion(s) of the patterned substrate that are not part of the bonding region may be coated with the water-soluble protective coating.

In this example of the method 100', selectively depositing or patterning the water-soluble protective coating may be accomplished via dip coating, spin coating, spray coating, ultrasonic spray coating, doctor blade coating, aerosol printing, or inkjet printing. A mask may be used to cover the bonding region of the patterned substrate so that the water-soluble protective coating is not applied on the bonding region.

Each of the example selective deposition or patterning techniques for the water-soluble protective coating may utilize an aqueous solution, which may include the water and up to about 15% (mass to volume) of a water-soluble material. In some examples, the water-soluble material makes up 15% or less of the aqueous solution. In other examples, the aqueous solution includes from about 2% to about 13% of the water-soluble material, or from about 2.5% to about 10% of the water-soluble material. It is to be understood that the concentration of the aqueous solution may vary depending upon the flow cell architecture (e.g., the dimensions of the flow channel, input and output ports (see reference numerals "I" and "O," respectively, in FIG. 5H), etc.). For example, when flow through deposition is utilized, the concentration may be selected so that the aqueous solution can flow through the flow cell without clogging the port(s), flow channel, etc. As such, the concentration may also be greater than about 15%. To obtain a desirable thickness, the lower limit of the concentration may be about 2 wt % (mass to volume). The water-soluble material (and the resulting protective coating), in this example of the method 100' may be any of the examples disclosed herein (i.e., a water-soluble non-cationic synthetic polymer; a water-soluble natural polysaccharide or a derivative thereof; a water-soluble natural protein or a derivative thereof; a water-soluble salt; a water-soluble small molecule compound selected from the group consisting of a water-soluble surfactant, a sugar, an antioxidant, a chelator, a buffer, a glycol; or a cyclodextrin). In an example, the water-soluble material may be a polyvinyl alcohol/polyethylene glycol graft copolymer (an example of this is commercially available as KOLLICOAT® IR, available from BASF Corp.), sucrose, dextran, polyacrylamide, polyethylene glycol, ethylenediaminetetraacetic acid disodium salt (EDTA), tris (hydroxymethyl)aminomethane with ethylenediaminetetraacetic acid, (tris(2-carboxyethyl)phosphine), tris(3-hydroxypropyltriazolylmethyl)amine, bathophenanthrolinedisulfonic acid disodium salt, glycerol, or saline sodium citrate.

The aqueous solution may also include additives, such as water-soluble co-solvents, antioxidants, dyes, ultraviolet light stabilizers, processing aids, or the like. These additives may be included in the aqueous solution in amounts that do not deleteriously affect the flowability or the solution or the film forming ability of the water-soluble, film forming material. For example, a co-solvent, such as ethanol, may be present, optionally in an amount ranging from about 1% to about 10%, or from about 2.5% to about 7.5%. In another example, the aqueous solution may include about 5% of the water-soluble material, about 5% of the co-solvent, and a balance (about 90%) of water. In other examples, the aqueous solution may include about 5 to about 7.5% of the water-soluble material, and about 5 to about 10% co-solvent, with the balance of water (e.g., 7.5% w/v KOLLICOAT® IR in 10% aq. ethanol).

After the aqueous solution is applied, it may be dried to form the water-soluble protective coating in solid or gel form. Drying may be accomplished via air exposure, nitrogen exposure, vacuum, heating (e.g., in an oven), or spin coating (i.e., spinning until dry).

Some examples of the protective coating may remain in liquid form, such as sodium chloride-sodium citrate (SSC). The liquid form of the protective coating constitutes wet storage because the solution may at least substantially fill a flow channel and cover the surface chemistry. The liquid form of the protective coating may be used, for example, when the flow channel is formed prior to protective coating application (e.g., at step 104''' in FIG. 2 or in FIGS. 6A-6E), so that the liquid can be contained therein. In an example, SSC is applied as a 0.75 M NaCl, 0.075M sodium citrate mixture.

This example of the method 100' then includes assembly, as shown at reference numeral 106. The protective coating protects the surface chemistry during any assembly processes. In an example, assembly involves bonding a lid to the bonding region of the patterned substrate to form a flow channel that is in selective fluid communication with the depression(s). When the patterned substrate is a wafer, different areas of the lid may at least partially define respective flow channels that are being formed using the wafer. When the patterned substrate is a die, the lid may define the one or more flow channels that is/are being formed.

The lid may be any material that is transparent to an excitation light that is directed toward the surface chemistry in the depression(s). As examples, the lid may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

In some examples, the lid may be integrally formed with sidewall(s) that correspond with the shape of bonding region, and that will be bonded to the bonding region. For example, a recess may be etched into a transparent block to form a substantially planar portion and sidewall(s) extending from the substantially planar portion. When the etched block is mounted to the bonding region of the patterned substrate, the recess may become the flow channel.

In other examples, the sidewall(s) and the lid may be separate components that are coupled to each other. For example, the lid may be a substantially rectangular block having an at least substantially planar exterior surface and an at least substantially planar interior surface that defines a portion (e.g., a top portion) of the flow channel (once bonded to the patterned substrate). The block may be mounted onto (e.g., bonded to) the sidewall(s), which are bonded to the bonding region of the patterned substrate and form sidewall (s) of the flow channel. In this example, the sidewall(s) may include any of the materials set forth herein for the spacer layer (described below).

The lid may be bonded to the bonding region of the patterned substrate using any suitable technique, such as laser bonding, diffusion bonding, anodic bonding, eutectic bonding, plasma activation bonding, glass frit bonding, or others methods known in the art. In an example, a spacer layer may be used to bond the lid to the bonding region of the patterned substrate. The spacer layer may be any material that will seal at least some of the interstitial regions (e.g., the bonding region) of the patterned substrate and the lid together.

In one example, the spacer layer may be a radiation-absorbing material that absorbs radiation at a wavelength that is transmitted by the lid and/or the patterned substrate. The absorbed energy, in turn, forms the bond between the spacer layer and the lid and between the spacer layer and the patterned substrate. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer is the radiation-absorbing material, the spacer layer may be positioned at an interface between the lid and the patterned substrate so that the spacer layer contacts the desired bonding region. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer may include a radiation-absorbing material in contact therewith. The radiation-absorbing material may be applied at the interface between the spacer layer and the lid as well as at the interface between the spacer layer and the patterned substrate. As an example, the spacer layer may be polyimide and the separate radiation-absorbing material may be carbon black. In this example, the separate radiation-absorbing material absorbs the laser energy that forms the bonds between the spacer layer and the lid and between the spacer layer and the patterned substrate. In this example, compression may be applied at the respective interfaces while laser energy at a suitable wavelength is applied to the interfaces (i.e., the radiation-absorbing material is irradiated).

When the patterned substrate is a wafer, the spacer layer and sidewalls (of or connected to the lid) may physically separate one flow channel from an adjacent flow channel and may be located at the periphery of the wafers. When the patterned substrate is a die and the flow cell that is being formed is to include a single flow channel or lane, the spacer layer and sidewalls (of or connected to the lid) may be located at the periphery of the die to define the flow channel and seal the flow cell. When the patterned substrate is a die and the flow cell that is being formed is to include multiple isolated flow channels (e.g., eight flow channels or four flow lanes), the spacer layer and sidewalls (of or connected to the lid) may physically separate one flow channel/lane from an adjacent flow channel/lane and may be located at the periphery of the die. It is to be understood, however, that the spacer layer and sidewalls may be located in any desired region depending on the implementation.

When the patterned substrate is a die, the assembly 106 of the method 100' involves the bonding of the lid, which forms the flow cell. When the patterned substrate is a wafer, the assembly 106 of the method 100' may involve additional processing, such as dicing. In one example, the lid may be bonded to the patterned wafer and dicing forms individual flow cells. As mentioned herein, on a wafer, the sidewalls may physically separate one flow channel from an adjacent flow channel, and thus dicing may take place through at least some of the sidewalls, so that each individual flow cell includes a desirable number of flow channels, each of which has a portion of the original sidewall surrounding its periphery. In another example, the patterned wafer may be diced to form non-lidded dies, which can have respective lids bonded thereto to form individual flow cells.

In one example, after the assembly 106, one or more flow cells are formed.

Referring now to the example method 100" in FIG. 2, the surface chemistry may be both the functionalized polymer coating layer and the primer(s), and two different protective coatings may be used. Like the method 100', adding the surface chemistry during the method 100" involves forming the functionalized polymer coating layer in the depression(s) (reference numeral 102') and grafting the primer to the functionalized polymer coating layer (reference numeral 102'). However, unlike the method 100', during the method 100" an initial water-soluble protective coating is formed after the functionalized polymer coating layer is formed (reference numeral 104") and another water-soluble protective coating is formed after the primer is grafted (reference numeral 104''').

At reference numeral 102' and 104" in method 100", adding the surface chemistry involves forming the functionalized polymer coating layer in the depression (102'), and the initial water-soluble protective coating is formed after the functionalized polymer coating layer is formed (104"). It is to be understood that materials and methods for forming the functionalized polymer coating layer as described herein may be used in the method 100". In an example, it may be desirable to deposit the initial water-soluble protective coating within about 5 hours of polishing the functionalized polymer coating layer. This time frame may decrease the surface decay rate of the functionalized polymer coating layer and may also provide a larger thermal processing window.

The initial water-soluble protective coating may be selectively deposited, or patterned, such that the surface chemistry (in this example, the functionalized polymer coating layer) is covered and such that a bonding region of the patterned substrate remains exposed. The bonding region is generally located on some of the interstitial region(s) of the patterned substrate where a lid will be bonded to the patterned substrate.

Selective deposition or patterning of the water-soluble protective coating may be accomplished via dip coating, spin coating, spray coating, ultrasonic spray coating, doctor blade coating, aerosol printing, or inkjet printing. As mentioned above, a mask may be used to cover the bonding region of the patterned substrate so that the initial water-soluble protective coating is not applied on the bonding region.

Each of the example selective deposition or patterning techniques for the initial water-soluble protective coating may utilize an aqueous solution, which may include the water and up to about 15% (mass to volume) of the water-soluble material. As mentioned herein, the concentration of the aqueous solution may vary depending upon the flow cell architecture (e.g., the dimensions of the flow channel, input and output ports, etc.), and thus may be greater than 15% or less than 15%. To obtain a desirable thickness, the lower limit of the concentration may be about 2 wt % (mass to volume). The water-soluble material (and the resulting protective coating), in this example of the method 100", may be the polyvinyl alcohol/polyethylene glycol graft copolymer, sucrose, polyacrylamide, or polyethylene glycol. In this example, the aqueous solution may also include additives, such as antioxidants, dyes, ultraviolet light stabilizers, processing aids, or the like.

As shown at reference numeral 106', the method 100" involves assembly of the flow cell after the initial protective coating is formed. In this example, the initial protective coating protects the functionalized polymer coating layer during any assembly processes. When the patterned substrate is a wafer, assembly involves bonding a lid to the bonding region to form respective flow channels that are in selective fluid communication with respective sets of the depressions, and then dicing the bonded lid and substrate to form respective flow cells. When the patterned substrate is a die, assembly involves bonding a lid to the bonding region to form a single flow cell with one or more flow channels. The bonding and/or dicing processes may be performed as described herein.

After the assembly 106' (i.e., bonding, or bonding and dicing), one or more flow cells are formed. The method 100' then involves removing the initial water-soluble protective coating, thereby exposing the functionalized polymer coating layer and the at least the portion of the patterned substrate (reference numeral 108, shown as IPC removal); grafting a primer to the functionalized polymer coating layer (reference numeral 102', shown as primer attachment); and forming a second water-soluble protective coating on the primer, the functionalized polymer coating layer and the at least the portion of the patterned substrate (reference numeral 104''', shown as protective coating formation).

The processes 108, 102''', and 104''' may take place in each of, or any one or more of the flow cells formed as a result of the assembly 106'.

Because the initial protective coating is water soluble, its removal may involve a dissolution process. Water and a buffer, or water, or an aqueous buffer may be introduced into the flow channel(s) of the flow cell(s) through respective input port(s) formed in the lid or the patterned substrate, may be maintained in the flow channel(s) for a time sufficient to dissolve the initial protective coating, and then may be removed from respective output port(s) formed in the lid or the patterned substrate. As such, the dissolution may be performed as a flow through process. When the protective coating dissolves, the solution that is formed will have a concentration of the water-soluble material that is relatively low (in some instances, e.g., about 15% or less, mass to volume), which enables the flow channel(s) and port(s) to remain unclogged. Upon dissolution of the initial protective coating and removal of the solution from the flow cell(s), the functionalized polymer coating layer and any of the patterned substrate that had been coated by the initial protective coating are exposed.

In this example of the method 100", the primer is then grafted to the functionalized polymer coating layer in the depression(s), as represented by reference numeral 102'. Any of the primers described herein may be used. In this example of the method 100", grafting may be accomplished by a flow through process. In the flow through process, the primer solution or mixture described herein may be introduced into the flow channel(s) of the flow cell(s) through respective input port(s), may be maintained in the flow channel(s) for a time sufficient (i.e., an incubation period) for the primer to attach to the functionalized polymer coating layer in one or more of the depressions, and then may be removed from respective output port(s). After primer attachment, the additional fluid(s) may be directed through the flow channel(s) to wash the now functionalized depressions and the flow channel(s).

In an example, after the primer is grafted to the functionalized polymer coating layer in the depression(s), this example of the method 100" further includes forming the (second) water-soluble protective coating on the surface chemistry (in this example, the functionalized polymer coating layer having the primer(s) attached thereto) and on at least a portion of the patterned substrate (reference numeral 104''').

In this example method 100", the (second) water-soluble protective coating may be deposited by a flow through process. In the flow through process, the aqueous solution (including water and, in some instances, up to about 15% (mass to volume) of the water-soluble, material) may be introduced into the flow channel(s) of the flow cell(s) through respective input port(s) and may be maintained in the flow channel(s). Enough of the aqueous solution may be introduced to cover the surface chemistry and any exposed surfaces of the patterned substrate within the flow channel. While the solution is in the flow channel(s), the flow cell(s) may be exposed to a dry down process where air, nitrogen, or vacuum is flushed through the input port for a set amount of time to dry the (second) water-soluble protective coating on the surface chemistry and any exposed portions of the substrate. In other example, the drying process may not be performed, and a liquid protective coating may be formed in the flow cell flow channel.

In this example method 100", the (second) water-soluble protective coating may be any of the examples disclosed herein (i.e., a water-soluble non-cationic synthetic polymer; a water-soluble natural polysaccharide or a derivative thereof; a water-soluble natural protein or a derivative thereof; a water-soluble salt; a water-soluble small molecule compound selected from the group consisting of a water-soluble surfactant, a sugar, an antioxidant, a chelator, a buffer, a glycol; or a cyclodextrin). In an example, the water-soluble material may be the polyvinyl alcohol/polyethylene glycol graft copolymer (e.g., KOLLICOAT® IR, available from BASF Corp.), sucrose, dextran, polyacrylamide, glycols, ethylenediaminetetraacetic acid sodium salt, tris(hydroxymethyl)aminomethane with ethylenediaminetetraacetic acid, (tris(2-carboxyethyl)phosphine), tris(3-hydroxypropyltriazolylmethyl)amine, bathophenanthrolinedisulfonic acid disodium salt, hydroxyl functional polymers, glycerol, or saline sodium citrate.

In another example, primer grafting and (second) water-soluble protective coating on the surface chemistry 20, 22 may occur simultaneously via a flow through process. In this example, a single solution includes the primer and the water-soluble material.

In one example, after the protective coating formation 104''', one or more flow cells are formed.

Figure 3:
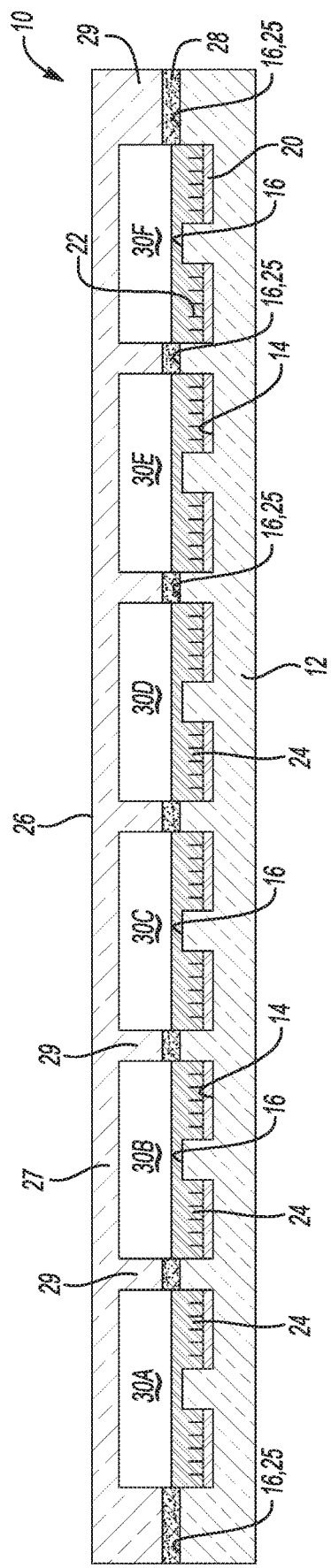
FIG. 3 is a cross-sectional view of an example flow cell formed by the methods shown in FIG. 2.

An example of the flow cell 10 formed by the method 100' or 100" is shown in FIG. 3. The flow cell 10 includes the patterned substrate 12, which may be a die that has been exposed to the processes of the method 100' or 100", or a wafer that has been that has been exposed to the processes of the method 100' or 100" and has been diced as a part of the assembly 106 or 106'.

Generally, the patterned substrate 12 includes depressions 14 separated by interstitial regions 16, and surface chemistry 20, 22 positioned in the depressions 14. The surface chemistry includes the functionalized polymer coating layer 20 and the primers 22. While not shown, it is to be understood that the depressions 14 may also have surface preparation chemistry (e.g., silane or a silane derivative) positioned between the substrate 12 and the functionalized polymer coating layer. This same surface preparation chemistry may also be positioned on the interstitial regions 16.

The flow cell 10 also includes the lid 26 bonded to bonding region(s) 25 of the patterned substrate 12, wherein the lid 26 at least partially defines a flow channel 30A, 30B, etc. that is in selective communication with the depressions 14. In the example shown in FIG. 3, the lid 26 includes a top portion 27 that is connected to several sidewalls 29, and these components 27, 29 define a portion of each of the six flow channels 30A, 30B, 30C, 30D, 30E, 30F. The respective sidewalls 29 isolate one flow channel 30A, 30B, 30C, 30D, 30E, 30F from each adjacent flow channel 30A, 30B, 30C, 30D, 30E, 30F, each flow channel 30A, 30B, 30C, 30D, 30E, 30F is in selective fluid communication with a respective set of the depressions 14.

While not shown, the lid 26 or the patterned substrate 12 may include inlet and outlet ports that are to fluidically engage other ports (not shown) for directing fluid(s) into the respective flow channels 30A, 30B, 30C, 30D, 30E, 30F (e.g., from a reagent cartridge or other fluid storage system) and out of the flow channel (e.g., to a waste removal system).

The water-soluble protective coating 24 covers the surface chemistry 20, 22 in the depressions 14, and at least a portion of the patterned substrate 12 (e.g., those interstitial regions 16 that are not also bonding regions 25). In the example flow cell 10, the protective coating 24 has been formed by the process shown at reference numeral 104' in method 100' or the process shown at reference numeral 104''' in method 100". As such, the protective coating 24 may be any of the examples disclosed herein (i.e., a water-soluble non-cationic synthetic polymer; a water-soluble natural polysaccharide or a derivative thereof; a water-soluble natural protein or a derivative thereof; a water-soluble salt; a water-soluble small molecule compound selected from the group consisting of a water-soluble surfactant, a sugar, an antioxidant, a chelator, a buffer, a glycol; or a cyclodextrin).

The flow cell 10 can be shipped, stored, etc. with the protective coating 24 in place. When it is desirable to utilize the flow cell 10 in an application (e.g., a sequencing operation), the protective coating may be at least partially removed via the dissolution process described in reference to reference numeral 108. Removal may take place as part of a sequencing operation. Alternatively, removal may not take place in order for sequencing to proceed.

The flow cell 10 shown in FIG. 3 could be formed using a non-patterned substrate instead of a patterned substrate. With a non-patterned substrate, a continuous surface would include the same surface chemistry 20, 22 that is found in the wells 14' of FIG. 3. An example is shown and further described in reference to FIGS. 6A through 6E.

Figure 4:
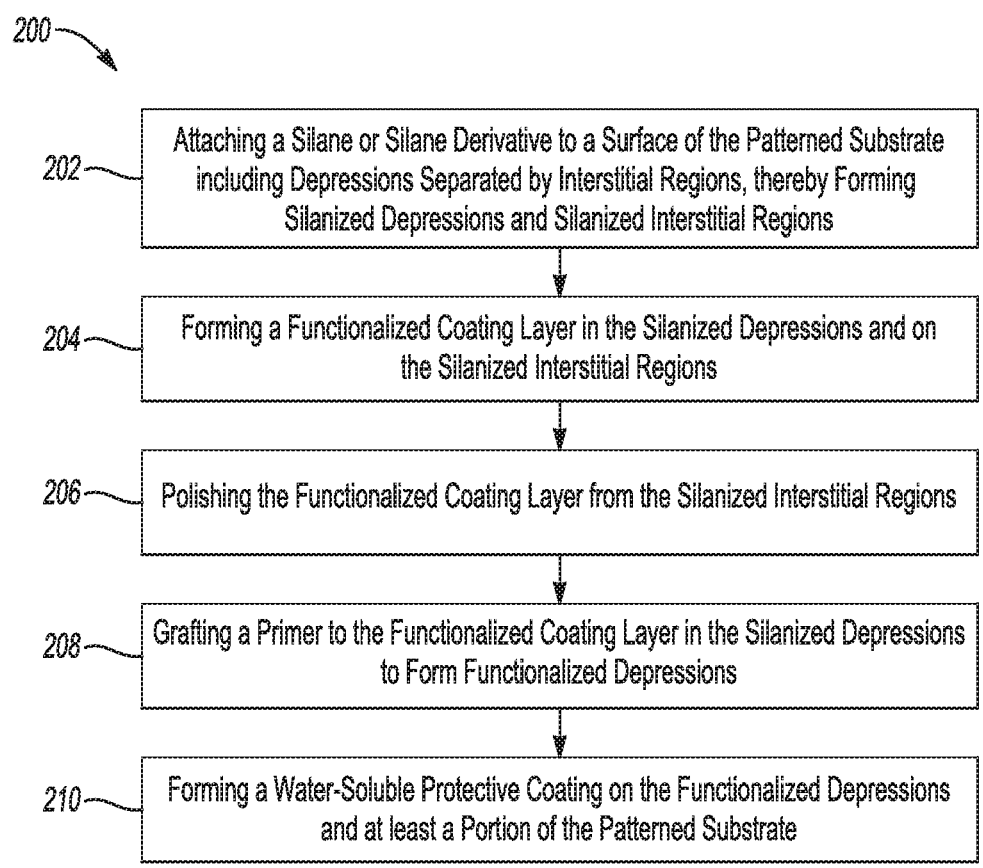
FIG. 4 is a flow diagram illustrating another example of the methods disclosed herein.

Another example of the method 200 is depicted in FIG. 4. This example of the method 200 is a variation of the method 100, and describes in detail some of the other processes that may be involved, such as process(es) that prepare the surface (i.e., depressions 14 and, in some instances, adjacent interstitial regions 16) of the patterned substrate 12 for the subsequent deposition of the surface chemistry 20, 22.

The method 200 includes attaching a silane or a silane derivative to a surface of the patterned substrate including depressions separated by interstitial regions, thereby forming silanized depressions and silanized interstitial regions (as shown at reference numeral 202); forming a functionalized polymer coating layer in the silanized depressions and on the silanized interstitial regions (as shown at reference numeral 204); polishing the functionalized polymer coating layer from the silanized interstitial regions (as shown at reference numeral 206); grafting a primer to the functionalized polymer coating layer in the silanized depressions to form functionalized depressions (as shown at reference numeral 208); and forming a water-soluble protective coating on the functionalized depressions and at least a portion of the patterned substrate (as shown at reference numeral 210).

Examples of the method 200 will be further described in reference to FIGS. 5A through 5H (which is similar to method 100'), or FIGS. 5A through 5D and 5I through 5L (which is similar to method 100"). Any details of the method 200 may also be combined with or included in the methods 100' or 100".

Figure 5A:
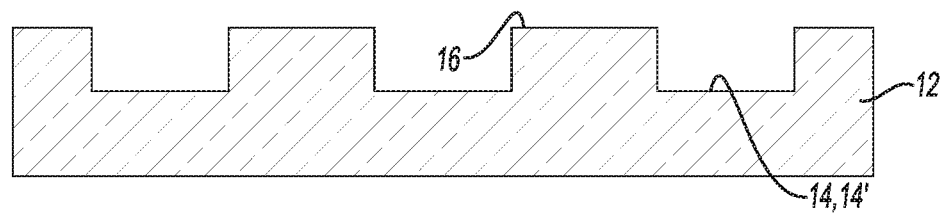
FIGS. 5A through 5H are cross-sectional views which together illustrate an example of the method shown in FIG. 4.

FIG. 5A is a cross-sectional view of the patterned substrate 12. The patterned substrate 12 may be a patterned wafer or a patterned die or any other patterned substrate (e.g., panel, rectangular sheet, etc.). Any example of the substrate 12 described herein may be used. The patterned wafer may be used to form several flow cells, and the patterned die may be used to form a single flow cell. In an example, the substrate may have a diameter ranging from about 2 mm to about 300 mm, or a rectangular sheet or panel having its largest dimension up to 10 feet (~3 meters). In an example, the substrate wafer has a diameter ranging from about 200 mm to about 300 mm. In another example, the substrate die has a width ranging from about 0.1 mm to about 10 mm. While example dimensions have been provided, it is to be understood that substrates with any suitable dimensions may be used.

The patterned substrate 12 includes depressions 14 defined on or in an exposed layer or surface of the substrate 12, and interstitial regions 16 separating adjacent depressions 14. In the examples disclosed herein, the depressions 14 become functionalized with surface chemistry (e.g., 20, 22), while the interstitial regions 16 may be used for bonding but will not have primer(s) (shown in FIGS. 5E and 5K) present thereon.

The depressions 14 may be fabricated in or on the substrate 12 using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the substrate 12.

Many different layouts of the depressions 14 may be envisaged, including regular, repeating, and non-regular patterns. In an example, the depressions 14 are disposed in a hexagonal grid for close packing and improved density. Other layouts may include, for example, rectilinear (i.e., rectangular) layouts, triangular layouts, and so forth. In some examples, the layout or pattern can be an x-y format of depressions 14 that are in rows and columns. In some other examples, the layout or pattern can be a repeating arrangement of depressions 14 and/or interstitial regions 16. In still other examples, the layout or pattern can be a random arrangement of depressions 14 and/or interstitial regions 16. The pattern may include spots, pads, wells, posts, stripes, swirls, lines, triangles, rectangles, circles, arcs, checks, plaids, diagonals, arrows, squares, and/or cross-hatches.

The layout or pattern may be characterized with respect to the density of the depressions 14 (i.e., number of depressions 14) in a defined area. For example, the depressions 14 may be present at a density of approximately 2 million per mm$^2$. The density may be tuned to different densities including, for example, a density of at least about 100 per mm$^2$, about 1,000 per mm$^2$, about 0.1 million per mm$^2$, about 1 million per mm$^2$, about 2 million per mm$^2$, about 5 million per mm$^2$, about 10 million per mm$^2$, about 50 million per mm$^2$, or more. Alternatively or additionally, the density may be tuned to be no more than about 50 million per mm$^2$, about 10 million per mm$^2$, about 5 million per mm$^2$, about 2 million per mm$^2$, about 1 million per mm$^2$, about 0.1 million per mm$^2$, about 1,000 per mm$^2$, about 100 per mm$^2$, or less. It is to be further understood that the density of depressions 14 on the substrate 12 can be between one of the lower values and one of the upper values selected from the ranges above. As examples, a high density array may be characterized as having depressions 14 separated by less than about 100 nm, a medium density array may be characterized as having depressions 14 separated by about 400 nm to about 1 µm, and a low density array may be characterized as having depressions 14 separated by greater than about 1 µm. While example densities have been provided, it is to be understood that substrates with any suitable densities may be used.

The layout or pattern may also or alternatively be characterized in terms of the average pitch, i.e., the spacing from the center of the depression 14 to the center of an adjacent interstitial region 16 (center-to-center spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 about 0.5 about 1 about 5 about 10 about 100 or more. Alternatively or additionally, the average pitch can be, for example, at most about 100 about 10 about 5 about 1 about 0.5 about 0.1 µm, or less. The average pitch for a particular pattern of sites 16 can be between one of the lower values and one of the upper values selected from the ranges above. In an example, the depressions 14 have a pitch (center-to-center spacing) of about 1.5 µm. While example average pitch values have been provided, it is to be understood that other average pitch values may be used.

In the examples shown in FIGS. 5A through 5L, the depressions 14 are wells 14', and thus the patterned substrate 12 includes an array of wells 14' in a surface thereof. The wells 14' may be micro wells or nanowells. Each well 14' may be characterized by its volume, well opening area, depth, and/or diameter.

Each well 14' can have any volume that is capable of confining a liquid. The minimum or maximum volume can be selected, for example, to accommodate the throughput (e.g. multiplexity), resolution, analyte composition, or analyte reactivity expected for downstream uses of the flow cell 10 (see FIGS. 5G and 5K). For example, the volume can be at least about $1\times10^3$ µm$^3$, about $1\times10^2$ µm$^3$, about 0.1 µm$^3$, about 1 µm$^3$, about 10 µm$^3$, about 100 µm$^3$, or more. Alternatively or additionally, the volume can be at most about $1\times10^4$ µm$^3$, about $1\times10^3$ µm$^3$, about 100 µm$^3$, about 10 µm$^3$, about 1 µm$^3$, about 0.1 µm$^3$, or less. It is to be understood that the functionalized polymer coating layer can fill all or part of the volume of a well 14'. The volume of the coating layer in an individual well 14' can be greater than, less than or between the values specified above.

The area occupied by each well opening on a surface can be selected based upon similar criteria as those set forth above for well volume. For example, the area for each well opening on a surface can be at least about $1\times10^{-3}$ µm$^2$, about $1\times10^{-2}$ µm$^2$, about 0.1 µm$^2$, about 1 µm$^2$, about 10 µm$^2$, about 100 µm$^2$, or more. Alternatively or additionally, the area can be at most about $1\times10^3$ µm$^2$, about 100 µm$^2$, about 10 µm$^2$, about 1 µm$^2$, about 0.1 µm$^2$, about $1\times10^2$ µm$^2$, or less. The area occupied by each well opening can be greater than, less than or between the values specified above.

The depth of each well 14' can be at least about 0.1 µm, about 1 µm, about 10 µm, about 100 µm, or more. Alternatively or additionally, the depth can be at most about $1\times10^3$ µm, about 100 µm, about 10 µm, about 1 µm, about 0.1 µm, or less. The depth of each well 14' can be greater than, less than or between the values specified above.

In some instances, the diameter of each well 14' can be at least about 50 nm, about 0.1 about 0.5 about 1 about 10 about 100 or more. Alternatively or additionally, the diameter can be at most about $1\times10^3$ µm, about 100 about 10 about 1 about 0.5 about 0.1 or less (e.g., about 50 nm). The diameter of each well 14' can be greater than, less than or between the values specified above.

The patterned substrate 12 may be exposed to a series of processes in order to add the surface chemistry 20, 22 in the depression(s) 14 and to form the water-soluble protective coating 24 on the surface chemistry 20, 22 and on at least a portion of the patterned substrate 12. FIGS. 5B through 5H together illustrate an example in which the surface chemistry 20, 22 is added before the protective coating 24 is formed; and FIGS. 5B through 5D and 5I through 5L together illustrate an example in which several protective coatings 24', 24 are formed in order to protect different surface chemistry 20, 22 at different stages of the method 200.

While not shown, it is to be understood that the patterned substrate 12 may be exposed to a plasma ashing in order to clean and activate the surface. For example, the plasma ashing process may remove organic material and introduce surface hydroxyl groups. Other suitable cleaning processes may be used to clean the substrate 12, depending, in part, on the type of substrate 12. For example, chemical cleaning may be performed with oxidizing agents or caustic solutions.

The patterned substrate 12 (shown in FIG. 5A) may then be exposed to a process that will prepare the surface 12 for deposition of the functionalized polymer coating layer 20 (FIG. 5C), which is one example of the surface chemistry disclosed herein. In an example, the patterned substrate 12 may be exposed to silanization, which attaches a silane or the silane derivative 18 (FIG. 5B) to the patterned wafer surface. Silanization introduces the silane or the silane derivative 18 across the surface, including in the depression 14, 14' (e.g., on the bottom surface and along the side walls) and on the interstitial regions 16.

Silanization may be accomplished using any silane or silane derivative 18. The selection of the silane or silane derivative 18 may depend, in part, upon the functionalized molecule that is to be used to form the functionalized polymer coating layer 20 (shown in FIG. 5C), as it may be desirable to form a covalent bond between the silane or silane derivative 18 and the functionalized polymer coating layer 20. The method used to attach the silane or silane derivative 18 to the substrate 12 may vary depending upon the silane or silane derivative 18 that is being used. Several examples are set forth herein.

In an example, the silane or silane derivative 18 is (3-aminopropyl)triethoxysilane (APTES) or 3-aminopropyl) trimethoxysilane (APTMS) (i.e., $X-R^B-Si(OR^C)_3$, wherein X is amino, $R^B$ is $-(CH_2)_3-$, and $R^C$ is ethyl or methyl). In this example, the substrate 12 surface may be pre-treated with the (3-aminopropyl)triethoxysilane (APTES) or 3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 $J/cm^2$ to 30 $J/cm^2$ of energy generates an active nitrene species, which can readily undergo a variety of insertion reactions with PAZAM (e.g., the functionalized molecule).

Other silanization methods may also be used. Examples of suitable silanization methods include vapor deposition, the YES method, spin coating, or other deposition methods. Some examples of methods and materials that may be used to silanize the substrate 12 are described herein, although it is to be understood that other methods and materials may be used.

In an example utilizing the YES CVD oven, the patterned substrate 12 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative 18 (e.g., liquid norbornene silane) may be deposited inside a glass vial and placed inside a glass vacuum desiccator with a patterned substrate 12. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivative 18, such as those silane or silane derivatives 18 including examples of the unsaturated moieties disclosed herein. As examples, these methods may be used when the silane or silane derivative 18 includes a cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo [4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl]trimethoxysilane. As other examples, these methods may be used when the silane or silane derivative 18 includes a cycloalkyne unsaturated moiety, such as cyclooctyne, a cyclooctyne derivative, or bicyclononynes (e.g., bicyclo[6.1.0]non-4-yne or derivatives thereof, bicyclo[6.1.0]non-2-yne, or bicyclo [6.1.0]non-3-yne). These cycloalkynes can be substituted with any of the R groups described herein.

Figure 5B:
Figure 5B:
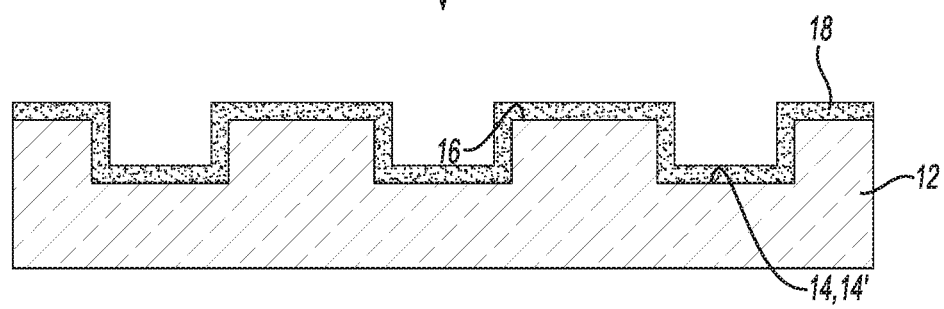

As shown in FIG. 5B, the attachment of the silane or silane derivative 18 forms a silanized patterned substrate, including silanized depressions and silanized interstitial regions.

The silanized patterned wafer may then be exposed to a process that will form the functionalized polymer coating layer 20 on the silanized depressions and silanized interstitial regions.

Figure 5C:
Figure 5C:
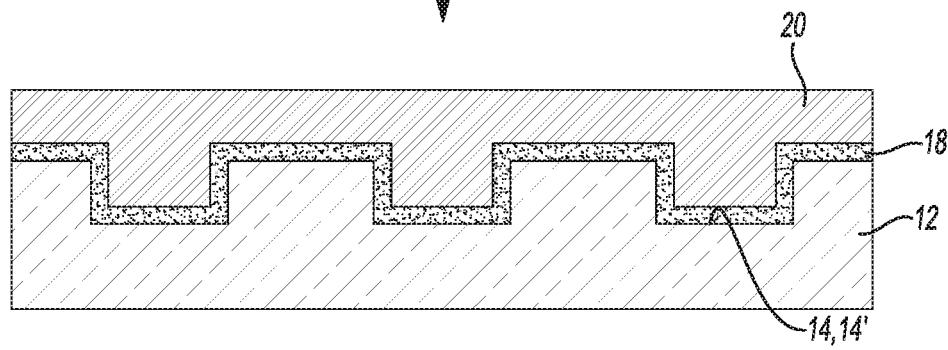

As described herein, examples of the functionalized polymer coating layer 20 include PAZAM, or any other molecule that is functionalized to interact with the patterned wafer 12 and the subsequently applied primer(s) 22. The functionalized polymer coating layer 20 may be formed on the surface of the silanized patterned wafer (i.e., onto the silanized depressions and the silanized interstitial regions) using any of the techniques described in reference to reference numeral 102'. The resulting coating layer 20 is shown in FIG. 5C.

The attachment of the functionalized polymer coating layer 20 to the silanized depressions and silanized interstitial regions (i.e., 18) may be through covalent bonding. The covalent linking of the functionalized polymer coating layer 20 to the silanized depressions is helpful for maintaining the functionalized polymer coating layer 20 in the depressions 14, 14' throughout the lifetime of the ultimately formed flow cell during a variety of uses. The following are some examples of reactions that can take place between the silane or silane derivative 18 and the functionalized polymer coating layer 20.

When the silane or silane derivative 18 includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; undergo a cycloaddition reaction with a hydrazone group attached to PAZAM; undergo a photo-click reaction with a tetrazole group attached to PAZAM; or undergo a cycloaddition with a nitrile oxide group attached to PAZAM.

When the silane or silane derivative 18 includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative 18 includes a bicyclononyne as the unsaturated moiety, the bicyclononyne can undergo similar SPAAC alkyne cycloaddition with azides or nitrile oxides attached to PAZAM due to the strain in the bicyclic ring system.

While not shown, it is to be understood that in some examples of the method, the patterned substrate 12 may not be exposed to silanization. Rather, the patterned substrate 12 may be exposed to plasma ashing, and then the functionalized polymer coating layer 20 may be directly spin coated (or otherwise deposited) on the plasma ashed patterned substrate 12. In this example, plasma ashing may generate surface-activating agent(s) (e.g., —OH groups) that can adhere the functionalized polymer coating layer 20 to the patterned substrate 12. In these examples, the functionalized polymer coating layer 20 is selected so that it reacts with the surface groups generated by plasma ashing.

Also while not shown, it is to be understood that the silanized and coated patterned substrate (shown in FIG. 5C) may be exposed to a cleaning process. This process may utilize a water bath and sonication. The water bath may be maintained at a relatively low temperature ranging from about 22° C. to about 45° C. In another example the water bath temperature ranges from about 25° C. to about 30° C.

Figure 5D:
Figure 5D:
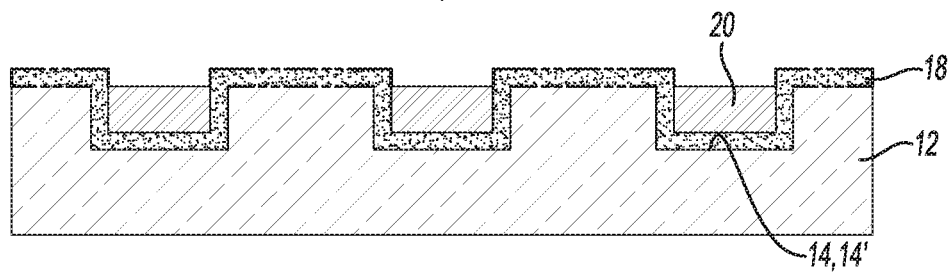

The silanized and coated patterned substrate is then exposed to polishing to remove portion(s) of the functionalized polymer coating layer 20 from the silanized interstitial regions. The silanized, coated, and polished patterned substrate is shown in FIG. 5D. The portions of the silane or silane derivative 18 that are adjacent to the interstitial regions 16 may or may not be removed as a result of polishing. As such, in FIGS. 5D through 5L, the portions of the silane or silane derivative 18 that are adjacent to the interstitial regions 16 are shown in phantom, as they may at least partially remain after polishing or they may be removed after polishing. When these silanized portions are completely removed, it is to be understood that the underlying substrate 12 is exposed. As such, in some examples, the spacer layer 28 may directly contact the substrate 12 at the bonding regions 25 (e.g., in FIGS. 5G and 5J) and the protective coatings 24', 24 may directly contact the substrate 12 at one or more interstitial region(s) 16 (e.g., in FIGS. 5F, 5J and 5L). When these silanized portions at least partially remain after polishing, the subsequently bonded lid and the subsequently formed protective coatings 24, 24' directly contact the silane or silane derivative 18 at the bonding regions 25 and the interstitial regions 16.

The polishing process may be performed with a gentle chemical slurry (including an abrasive) which can remove the thin functionalized polymer coating layer 20, and in some instances, at least part of the silane or silane derivative 18, from the interstitial regions 16 without deleteriously affecting the underlying substrate 12 at those regions. Alternatively, polishing may be performed with a solution that does not include the abrasive particles.

The gentle chemical slurry is a basic, aqueous slurry having a pH ranging from about 7.5 to about 11 and including an abrasive particle. Examples of the abrasive particle include calcium carbonate ($CaCO_3$), agarose, graphite, poly(methyl methacrylate) (PMMA), silica, aluminum oxide (i.e., alumina), ceria, polystyrene, and combinations thereof. In some examples, the abrasive particle is selected from the group consisting of calcium carbonate ($CaCO_3$), agarose, and graphite. The average particle size of the abrasive particles may range from about 15 nm to about 5 µm, and in one example is about 700 nm.

In addition to the abrasive particles, the basic, aqueous slurry may also include a buffer, a chelating agent, a surfactant, and/or a dispersant. An example of the buffer includes tris base (i.e., tris(hydroxymethyl)aminomethane), which may be present in a solution having a pH of about 9. An example of the chelating agent is ethylenediaminetetraacetic acid (EDTA), which may be present in a solution having a pH of about 8. An example of the surfactant is an anionic surfactant, such as sodium dodecyl sulfate. Polyacrylate dispersants having different molecular weights may be used. An example of the dispersant is poly(acrylic acid sodium salt). The dispersant may help to maintain the size of, and at least substantially prevent settling of the abrasive particles.

The basic, aqueous slurry may be used in a chemical mechanical polishing system to polish the surface of the silanized and coated patterned substrate shown in FIG. 5C. The polishing head(s)/pad(s) or other polishing tool(s) is/are capable of polishing the functionalized polymer coating layer 20 from the interstitial regions 16 while leaving the functionalized polymer coating layer 20 in the depressions 14, 14' and leaving the underlying substrate 12 at least substantially intact. As an example, the polishing head may be a Strasbaugh ViPRR II polishing head.

As mentioned above, polishing may be performed with a polishing pad and a solution without any abrasive. For example, the polish pad may be utilized with a solution free of the abrasive particle (i.e., a solution that does not include abrasive particles).

Polishing removes portion(s) of the functionalized polymer coating layer 20 (and in some instances at least part of the silane or silane derivative 18) from the interstitial regions 16 and leaves portion(s) of the functionalized polymer coating layer 20 in the silanized depressions, as shown in FIG. 5D. Also as mentioned above, the interstitial region(s) 16 may remain silanized after polishing is complete. In other words, the silanized interstitial regions may remain intact after the polishing. Alternatively (as indicated by the phantom portions of 18), the silane or silane derivative 18 may be removed from the interstitial region(s) 16 as a result of polishing.

While not shown, it is to be understood that the silanized, coated, and polished patterned substrate (shown in FIG. 5D) may be exposed to a cleaning process. This process may utilize a water bath and sonication. The water bath may be maintained at a relatively low temperature ranging from about 22° C. to about 30° C. The silanized, coated, and polished patterned substrate may also be spin dried, or dried via another suitable technique.

The silanized, coated, and polished patterned substrate shown in FIG. 5D may then be exposed to the processes shown in FIGS. 5E through 5H or to the processes shown in FIGS. 5I through 5L. In FIGS. 5E through 5H, a single water-soluble protective coating 24 is formed, and in FIGS. 5I through 5L, multiple water-soluble protective coatings 24', 24 are formed.

Figure 5E:
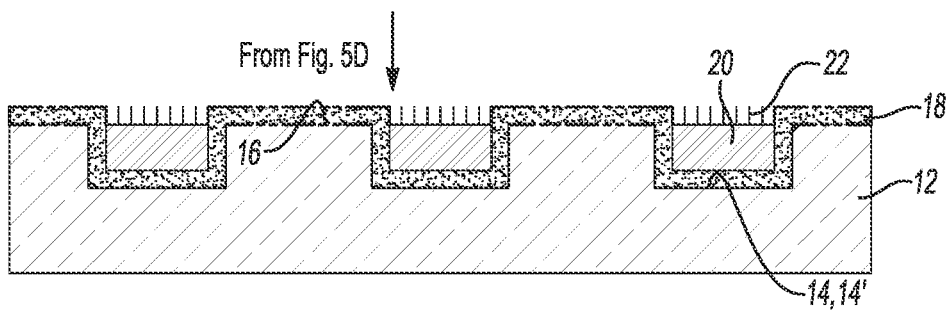

The example shown in FIGS. 5E though 5H will now be described. In FIG. 5E, the primer 22 is grafted to the functionalized polymer coating layer 20 in the depression(s) 14, 14'. Any of the primers described herein may be used. In this example, grafting may be accomplished by dunk coating, spray coating, puddle dispensing, or by another suitable method that will attach the primer(s) to the functionalized polymer coating layer 20 in at least some of the depressions 14, 14'. Each of these example techniques may utilize the primer solution or mixture described herein, which may include the primer(s), water, a buffer, and a catalyst.

Figure 5F:
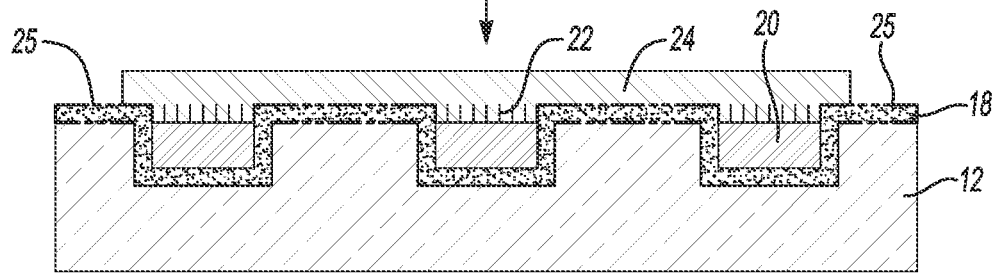

As shown in FIG. 5F, after the primer 22 is grafted to the functionalized polymer coating layer 20 in the depressions 14, 14', the water-soluble protective coating 24 is formed on the surface chemistry 20, 22 and on at least a portion of the patterned substrate. The water-soluble protective coating 24 may be formed on the exposed surface of the patterned substrate 12 that is not part of a bonding region 25. In this example, the water-soluble protective coating 24 is selectively deposited or patterned on the interstitial regions 16 between adjacent depressions 14, 14', but not at the edge/periphery of the patterned substrate 12 where the bonding region 25 is located. The selective deposition/patterning of the water-soluble protective coating 24 may be accomplished using the aqueous solution, as described herein. In this example, the material in the aqueous solution may be any of the examples disclosed herein (i.e., a water-soluble non-cationic synthetic polymer; a water-soluble natural polysaccharide or a derivative thereof; a water-soluble natural protein or a derivative thereof; a water-soluble salt; a water-soluble small molecule compound selected from the group consisting of a water-soluble surfactant, a sugar, an antioxidant, a chelator, a buffer, a glycol; or a cyclodextrin). In an example, the water-soluble material may be the polyvinyl alcohol/polyethylene glycol graft copolymer, sucrose, dextran, polyacrylamide, glycols, ethylenediaminetetraacetic acid sodium salt, tris(hydroxymethyl)aminomethane with ethylenediaminetetraacetic acid, (tris(2-carboxyethyl)phosphine), tris(3-hydroxypropyltriazolylmethyl)amine, bathophenanthrolinedisulfonic acid disodium salt, hydroxyl functional polymers, glycerol, or saline sodium citrate. After the aqueous solution is deposited, it may be dried to form the water-soluble protective coating 24.

Figure 5G:
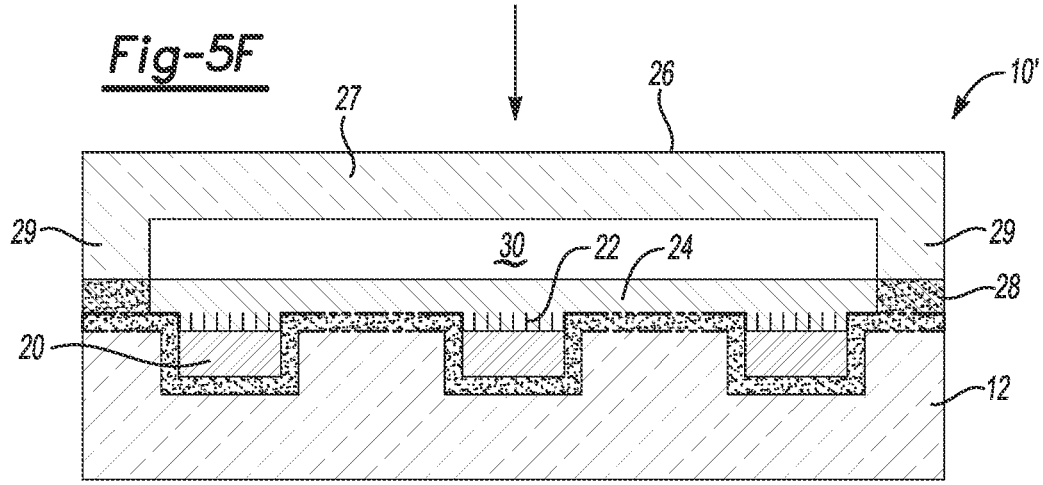

As depicted in FIG. 5G, the lid 26 may then be bonded to the bonding region 25. The lid 26 may be any of the materials and in any of the configurations described herein. The lid 26 may also be bonded to the bonding region 25 via any of the techniques described herein.

In the example shown in FIG. 5G, the lid 26 includes a top portion 27 integrally formed with sidewall(s) 29. The sidewall(s) 29 are bonded to the bonding region 25 of the patterned substrate 12 through the spacer layer 28.

Together, the lid 26 and the patterned substrate 12 (with the surface chemistry 20, 22) define the flow channel 30, which is in selective fluid communication with the depressions 14, 14'. The flow channel 30 may serve to, for example, selectively introduce fluid to the protective coating 24 in order to remove the coating 24, and to selectively introduce reaction components or reactants to the surface chemistry 20, 22 (after the protective coating 24 is removed) in order initiate designated reactions in/at the depressions 14, 14'.

When the lid 26 is bonded to the silanized, coated, polished, and grafted patterned substrate, an example of the flow cell 10' is formed, as shown in FIG. 5G. In this example, the protective coating 24 remains in place on the surface chemistry 20, 22 and on some of the patterned substrate surface. The flow cell 10' can be shipped, stored, etc. with the protective coating 24 in place.

Figure 5H:
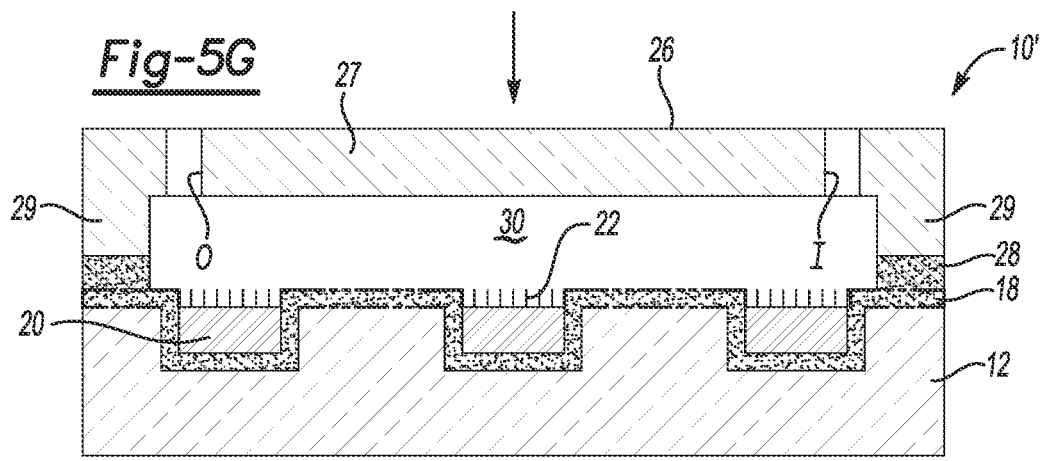

When it is desirable to utilize the flow cell 10' in an application (e.g., a sequencing operation), the protective coating 24 may be removed via the dissolution process described in reference to reference numeral 108. The water solubility of the protective coating 24 enables it to be removed via dissolution in the aqueous solution, which is not deleterious to the underlying surface chemistry 20, 22 or patterned substrate 12. FIG. 5H depicts the flow cell 10' after the protective coating 24 is removed.

Figure 5I:
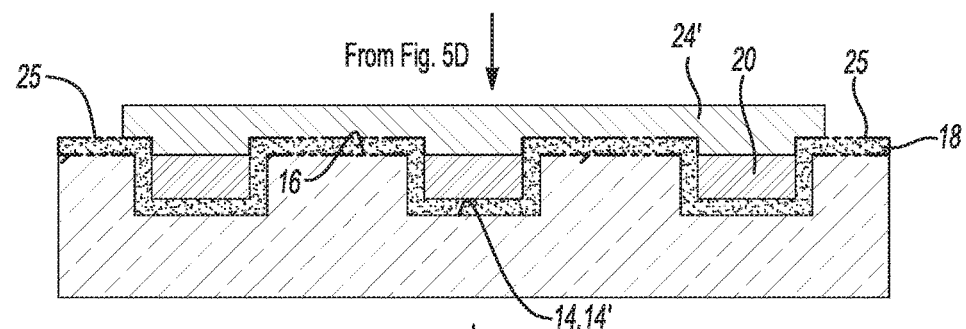

The example shown in FIGS. 5I though 5L will now be described. In FIG. 5I, the initial water-soluble protective coating 24' may be selectively deposited, or patterned, such that the functionalized polymer coating layer 20 is covered and such that the bonding region 25 of the patterned substrate 12 remains exposed. In this example, the initial water-soluble protective coating 24' is selectively deposited or patterned on the interstitial regions 16 between adjacent depressions 14, 14', but not at the edge/periphery of the patterned substrate 12 where the bonding region 25 is located. The selective deposition/patterning of the initial water-soluble protective coating 24' may be accomplished as described herein using the aqueous solution described in reference to reference numeral 104" (which includes water and, in some instances, up to about 15% (mass to volume) of the polyvinyl alcohol/polyethylene glycol graft copolymer, sucrose, or polyethylene glycol).

Figure 5J:
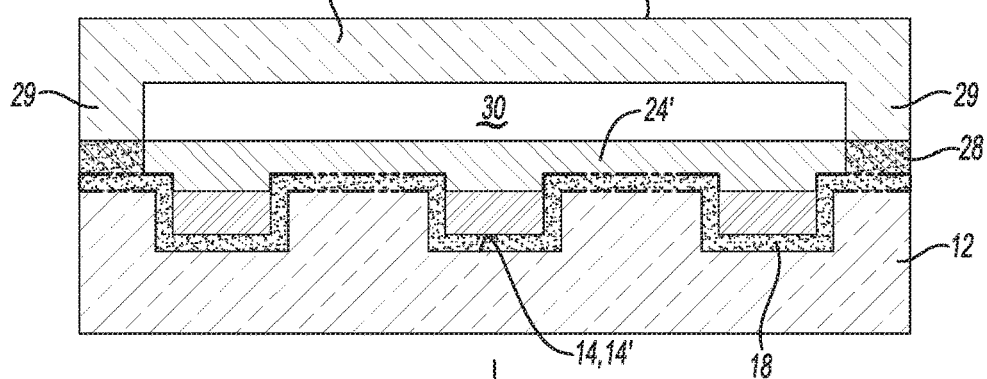

The initial protective coating 24 protects the functionalized polymer coating layer 20 during any assembly processes that are subsequently performed. As depicted in FIG. 5J, the assembly process may include bonding the lid 26 to the bonding region 25. While not shown, when the substrate wafer is used, the assembly process may include bonding and dicing. The lid 26 may be any of the materials and may have any of the configurations described herein. The lid 26 may be bonded to the bonding region 25 via any of the techniques described herein.

In the example shown in FIG. 5J, the lid 26 includes a top portion 27 integrally formed with sidewall(s) 29. The sidewall(s) 29 are bonded to the bonding region 25 of the patterned substrate 12 through the spacer layer 28. After the lid 26 is bonded, the flow channel 30 is formed between the lid 26 and the patterned substrate 12. The flow channel 30 may serve to selectively introduce various fluids to the flow cell 10'.

Figure 5K:
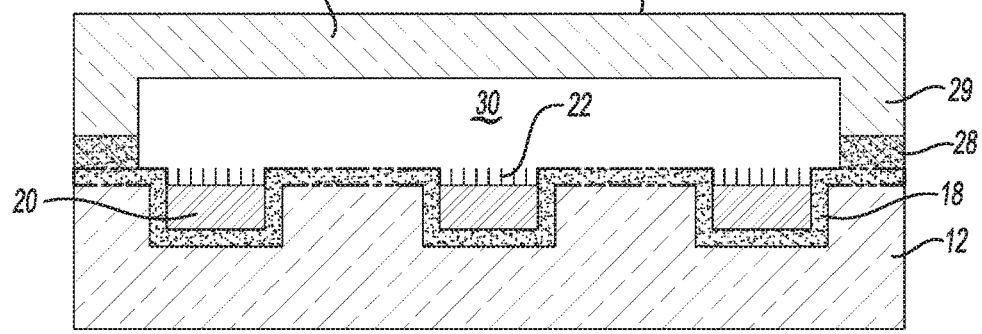

The initial water-soluble protective coating 24' then may be removed, as shown in FIG. 5K. Because the initial protective coating is water soluble, its removal may involve aqueous dissolution, as described in reference to reference numeral 108. Upon dissolution of the initial protective coating 24' and removal of the solution from the flow channel 30, the functionalized polymer coating layer 20 and any of the patterned substrate 12 (e.g., interstitial regions 16 not bonded to the lid 26) that had been coated by the initial protective coating 24' are exposed.

Also shown in FIG. 5K, after the initial protective coating 24' is removed, the primer 22 may be grafted to the functionalized polymer coating layer 20 in the depression(s) 14, 14'. Any of the primers 22 described herein may be used. In this example, grafting may be accomplished using the flow through process (reference numeral 102'''), and the primer solution or mixture described herein, which may include the primer(s), water, a buffer, and a catalyst. After the primer 22 is grafted, the flow cell 10' is formed.

Figure 5L:
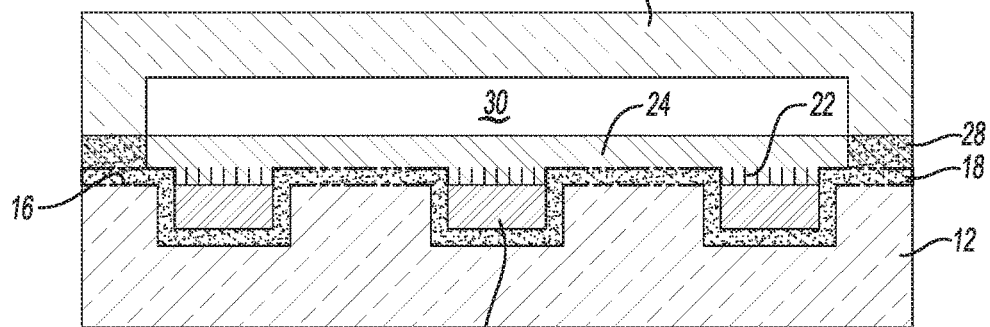

If the flow cell 10' is to be shipped, or stored for some period of time, the (second) water-soluble protective coating 24 may be applied to the surface chemistry 20, 22 and on at least a portion of the patterned substrate 12 (i.e., interstitial regions 16 exposed within the channel 30), as shown in FIG. 5L. The deposition of the (second) water-soluble protective coating 24 may be accomplished using the flow through process and the aqueous solution described in reference to reference numeral 104'''. To reiterate, the water-soluble material in the aqueous solution in this example may be any of the examples disclosed herein (i.e., a water-soluble non-cationic synthetic polymer; a water-soluble natural polysaccharide or a derivative thereof; a water-soluble natural protein or a derivative thereof; a water-soluble salt; a water-soluble small molecule compound selected from the group consisting of a water-soluble surfactant, a sugar, an antioxidant, a chelator, a buffer, a glycol; or a cyclodextrin). In an example, the water-soluble material may be the polyvinyl alcohol/polyethylene glycol graft copolymer, sucrose, dextran, polyacrylamide, glycols, ethylenediaminetetraacetic acid sodium salt, tris(hydroxymethyl)aminomethane with ethylenediaminetetraacetic acid, (tris(2-carboxyethyl)phosphine), tris(3-hydroxypropyltriazolylmethyl)amine, bathophenanthrolinedisulfonic acid disodium salt, hydroxyl functional polymers, glycerol, or saline sodium citrate.

Still another example of the method (e.g., method 100 or 200) involves a non-patterned substrate 12', as shown in FIGS. 6A through 6E.

Any of the substrates disclosed herein, and non-patterned substrate 12' does not include depressions 14 or interstitial regions 16. In this example method, the lid 26 is bonded to the non-patterned substrate 12' at the outset to form the flow channel(s) 30. The lid 26 may be any of the materials and in any of the configurations described herein. The lid 26 may also be bonded to the non-patterned substrate 12' via any of the techniques described herein.

In the example shown in FIG. 6B, the lid 26 includes a top portion 27 integrally formed with sidewall(s) 29. The sidewall(s) 29 are bonded to a bonding region of the non-patterned substrate 12' through the spacer layer 28. The bonding region may be at a periphery of the non-patterned substrate 12', or at any areas where it is desirable to form a boundary of a flow channel 30. In other examples, the spacer layer 28 may form the sidewall(s) and may be attached to an at least substantially planar lid 26.

Together, the lid 26 (including the sidewall(s) 29) and the non-patterned substrate 12 define the flow channel 30. The flow channel 30 may serve to, for example, selectively introduce fluids in order to form the surface chemistry 20, 22 and the protective coating 24, to remove the coating 24, and to selectively introduce reaction components or reactants to the surface chemistry 20, 22 (after the protective coating 24 is removed) in order initiate designated reactions within the flow channel 30.

Prior to forming the functionalized polymer coating layer 20 (shown in FIG. 6C), the method may involve exposing the non-patterned substrate (via a flow through process) to a cleaning process and/or to another process (e.g., silanization) that prepares the exposed surface of the non-patterned substrate for the subsequent deposition of the functionalized molecule.

Silanization of the non-patterned substrate 12' is shown in FIG. 6B. In this example, silanization attaches the silane or the silane derivative 18 to the exposed portions of the non-patterned wafer surface 12' that are present in the flow channel 30.

Silanization may be accomplished using any silane or silane derivative 18. The selection of the silane or silane derivative 18 may depend, in part, upon the functionalized molecule that is to be used to form the functionalized polymer coating layer 20 (shown in FIG. 6C), as it may be desirable to form a covalent bond between the silane or silane derivative 18 and the functionalized polymer coating layer 20. The method used to attach the silane or silane derivative 18 to the substrate 12' may be a flow through process.

As shown in FIG. 6C, in this example, the functionalized polymer coating layer 20 is then formed on the silane or silane derivative 18, or on other chemistry that has been deposited to prepare the exposed surface of the non-patterned substrate 12' within the flow channel 30.

Any of the functionalized molecules described herein may be used. In this example, functionalized polymer coating layer formation may be accomplished by a flow through process. In the flow through process, the functionalized molecule may be introduced into the flow channel(s) 30 through respective input port(s) and may be cured. The functionalized polymer coating layer 20 will form on the exposed surface of the non-patterned substrate 12' and polishing does not take place.

As shown in FIG. 6D, the primer 22 is grafted to the functionalized polymer coating layer 20 in the flow channel 30. Any of the primers described herein may be used. In this example, grafting may be accomplished by a flow through process. In the flow through process, the primer solution or mixture described herein may be introduced into the flow channel(s) 30 through respective input port(s), may be maintained in the flow channel(s) for a time sufficient (i.e., an incubation period) for the primer to attach to the functionalized polymer coating layer 20, and then may be removed from respective output port(s). After primer attachment, the additional fluid(s) may be directed through the flow channel(s) to wash the now functionalized flow channel (s) 30.

The resulting flow cell 10'' in this example is shown in FIG. 6D. This flow cell 10'' may be used in a sequencing operation, or may be coated with the protective coating 24 for shipping and/or storage.

As shown in FIG. 6E, in an example, after the primer 22 is grafted to the functionalized polymer coating layer 20 in the flow channel 30, the water-soluble protective coating 24 is formed on the surface chemistry 20, 22. In this example, water-soluble protective coating 24 formation may be accomplished by a flow through process. In the flow through process, the aqueous solution (including water and, in some instances, up to about 15% (mass to volume) of a water-soluble, film forming material) may be introduced into the flow channel(s) 30 through respective input port(s) and may be maintained in the flow channel(s). Enough of the aqueous solution may be introduced to cover the surface chemistry 20, 22 within the flow channel 30. While in the flow channel(s) 30, the flow cell(s) may be exposed to a dry down process where air, nitrogen, or vacuum is flushed through the input port for a set amount of time to dry the (second) water-soluble protective coating on the surface chemistry 20, 22.

In this example, the water-soluble material in the aqueous solution may be any of the examples disclosed herein (i.e., a water-soluble non-cationic synthetic polymer; a water-soluble natural polysaccharide or a derivative thereof; a water-soluble natural protein or a derivative thereof; a water-soluble salt; a water-soluble small molecule compound selected from the group consisting of a water-soluble surfactant, a sugar, an antioxidant, a chelator, a buffer, a glycol; or a cyclodextrin). In an example, the water-soluble material may be any of the polyvinyl alcohol/polyethylene glycol graft copolymer, sucrose, dextran, polyacrylamide, glycols, ethylenediaminetetraacetic acid sodium salt, tris (hydroxymethyl)aminomethane with ethylenediaminetetraacetic acid, (tris(2-carboxyethyl)phosphine), tris(3-hydroxypropyltriazolylmethyl)amine, bathophenanthrolinedisulfonic acid disodium salt, hydroxyl functional polymers, glycerol, or saline sodium citrate.

It is to be understood that primer grafting and water-soluble protective coating 24 formation may occur simultaneously in some examples.

When it is desirable to utilize the flow cell 10" (having the protective coating 24 on the surface chemistry 20, 22) in an application (e.g., a sequencing operation or a genotyping operation), the protective coating 24 may be removed via the dissolution process described in reference to reference numeral 108. The water solubility of the protective coating 24 enables it to be removed via dissolution in the aqueous solution, which is not deleterious to the underlying surface chemistry 20, 22.

Moreover, the methods disclosed herein may involve performing a quality control assay. In an example, the assay may be a CFR or a HP-TET assay or another suitable dye-based assay. The assay may be performed prior to introducing the protective coating 24 (but after primer grafting), and then again after the protective coating 24 is removed (and the primers are re-exposed). The assay data may indicate whether any primer degradation has occurred. In an example, the method involves removing the water-soluble protective coating; and performing a dye-based assay to detect any degradation of the primer. In an example, flow cell 10, 10', 10" disclosed herein may exhibit less than a 15% drop in CFR retention after 2 days of storage with the protective coating thereon, and in another example, less than a 10% drop in CFR retention after 2 days of storage with the protective coating thereon. In still another example, the flow cell 10, 10', 10" may not exhibit a drop in CFR retention, but rather, may exhibit an increased CFR retention (ranging, for example, from about 1% to about 25%, or for another example, from about 5% to about 20%). In another example, following primer grafting but prior to application of the water-soluble coating, the primer grafting efficiency may be detected by hybridization of the grafted primers to labeled quality control oligonucleotides. The hybridized quality control oligonucleotides are detected and then dehybridized from the grafted primers. The water-soluble coating is then applied.

The examples disclosed herein illustrate that the protective coating 24 is not formed on bonding regions 25. In other examples, however, the protective coating 24 may be formed on the entire substrate 12, 12' surface (i.e., on the surface chemistry 20, 22, in some examples on interstitial regions 16, and on the bonding regions 25), and the lid 26 may be bonded to the substrate 12, 12' through the protective coating 24.

While not shown, it is to be understood that some examples of the flow cell 10, 10', 10" may be affixed directly to, and thus be in physical contact with, a detection device (not shown) through one or more securing mechanisms (e.g., adhesive, bond, fasteners, and the like). The detection device may include a CMOS device (which includes a plurality of stacked layers including, for example, silicon layer(s), dielectric layer(s), metal-dielectric layer(s), metal layer(s), etc.) and optical components. The optical components may be arranged such that an optical sensor of the detection device is at least substantially aligned with, and thus is operatively associated with, a single optical waveguide of the detection device and the surface chemistry 20, 22 within a single depression 14, 14' of the flow cell 10, 10', 10".

Also while not shown, it is to be understood that instead of being bonded to a lid 26, a functionalized substrate (with surface chemistry, 20, 22 thereon or in depression(s) 14 thereof) may be bonded to another functionalized substrate with surface chemistry, 20, 22 thereon on in depression(s) thereof. The two functionalized surfaces can face each other and can have a flow channel defined therebetween. A spacer layer and suitable bonding method may be used to bond two of the functionalized substrates together.

The flow cells 10, 10', 10" disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques and in examples using a patterned substrate, since the functional molecule layer 20 and attached sequencing primer(s) 22 are present in the functionalized depressions (i.e., 14, 14' with surface chemistry 20, 22 thereon) and not on the interstitial regions 16, amplification will be confined to the functionalized depressions. In other examples, amplification can take place across an entire flow cell lane.

As one example, a sequencing by synthesis (SBS) reaction may be run on a system such as the HiSeq™, HiSeqX™, MiSeq™, NovaSeq™, or NextSeq™ sequencer systems from Illumina (San Diego, Calif.). In SBS, extension of a nucleic acid primer along a nucleic acid template is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the primer 22 (thereby extending the primer 22) in a template dependent fashion such that detection of the order and type of nucleotides added to the primer 22 can be used to determine the sequence of the template. For example, to initiate a first SBS cycle, one or more labeled nucleotides, DNA polymerase, etc., may be delivered into/through the flow channel 30, 30A, etc. that houses an array of primers 22. The functionalized depressions (i.e., 14, 14' with surface chemistry 20, 22 thereon), where primer extension causes a labeled nucleotide to be incorporated, can be detected through an imaging event. During an imaging event, an illumination system (not shown) may provide an excitation light to the functionalized depressions (i.e., 14, 14' with surface chemistry 20, 22 thereon).

In some examples, the nucleotides can further include a reversible termination property that terminates further primer extension once a nucleotide has been added to the primer 22. For example, a nucleotide analog having a reversible terminator moiety can be added to the primer 22 such that subsequent extension cannot occur until a deblocking agent is delivered to remove the moiety. Thus, for examples that use reversible termination, a deblocking reagent can be delivered to the flow channel 30, 30A, etc. (before or after detection occurs).

Wash(es) may take place between the various fluid delivery steps. The SBS cycle can then be repeated n times to extend the primer 22 by n nucleotides, thereby detecting a sequence of length n.

While SBS has been described in detail, it is to be understood that the flow cells 10, 10', 10" described herein may be utilized with other sequencing protocol, for genotyping, or in other chemical and/or biological applications.

To further illustrate the present disclosure, examples are given herein. It is to be understood that these examples are provided for illustrative purposes and are not to be construed as limiting the scope of the disclosure.

In some of these examples, the protective coatings are dried and some of the protective coatings are wet. The wet coatings are referred to as "wet storage" or "wet stored". While the coatings that were exposed to a drying process were visibly dry and appeared solid, it is to be understood that traces of moisture may have been present. The wet coatings were in liquid form.

NON-LIMITING WORKING EXAMPLES

Example 1

The example flow cells (1A and 1B) included several flow channels/lanes defined on a patterned silicon and/or a tantalum oxide substrate, where each lane was in fluid communication with a plurality of wells. A PAZAM layer was formed in each well, and 1 µm primers were grafted on the PAZAM layer. Protective coatings were ultimately formed on the surface chemistry (as described below). Some of the protective coatings were dried and one of the protective coatings was wet.

A comparative flow cell was tested. The surface chemistry was the same as the example flow cells. No protective coating was formed on the surface chemistry of the comparative flow cell.

A first HP-TET quality control assay was performed in each of the lanes of each of the example and comparative flow cell before the protective coatings were added to the example flow cells. HP or hairpin defines the secondary structure part of the DNA molecule used to probe the primers on the grafted flowcell surface, and TET (or TET+ DNA) is a dye labeled oligonucleotide having complementary sequence to the primers used. TET was hybridized to the primers, the excess TET was washed away, and the fluorescence of the attached dye was measured by fluorescence detection.

After the first HP-TET assay, several aqueous solutions of a polyvinyl alcohol/polyethylene glycol graft copolymer (in this example KOLLICOAT® IR) were prepared. Each solution had a different concentration of the copolymer ranging from 0.10% to 10% (mass to volume). A flow through process was used to introduce one of the aqueous solutions into one of the lanes of each of the flow cells, and onto the PAZAM layers and primers within the respective lanes. The aqueous solution was dried to form a protective coating. Each of the dried protective coatings had a different concentration of the copolymer. These example cells and the comparative cell were dried using nitrogen gas.

The dried example flow cells were then dry stored for 3 days at 60° C. (equivalent to dry storage for 1 month at 25° C. or ambient conditions) with the protective coating in place.

The comparative uncoated flow cell ("uncoated") was exposed to the same dry storage conditions.

Another protective coating was formed by introducing a liquid sodium chloride-sodium citrate (SSC) buffer using a flow through process. Thus, this example flow cell was exposed to wet storage conditions in which the sodium chloride-sodium citrate (SSC) buffer at 4° C. was left to soak on the flow cell surface chemistry.

After storage, the protective coating was removed from the lanes of the respective example flow cells via aqueous dissolution during washing, and the wet stored flow cell was rinsed out. Another HPTET quality control assay was performed in each of the lanes of each of the example and comparative flow cells.

The HP-TET retention rate results were calculated using the before coating and after storage HP-TET results. The retention rates are shown in FIG. 7. As depicted, the HP-TET retention generally increased with increasing copolymer concentrations for both flow cells 1A and 1B. At or below 1%, the copolymer coating was not as effective as the comparative example or the wet storage. This example illustrates that at copolymer concentrations ranging from about 2.5% to about 10%, the protective coating improves the dry storage stability of the surface chemistry compared to uncoated surface chemistry stored at the same dry conditions and approaches the stability of the wet storage conditions.

Example 2

Figure 8:
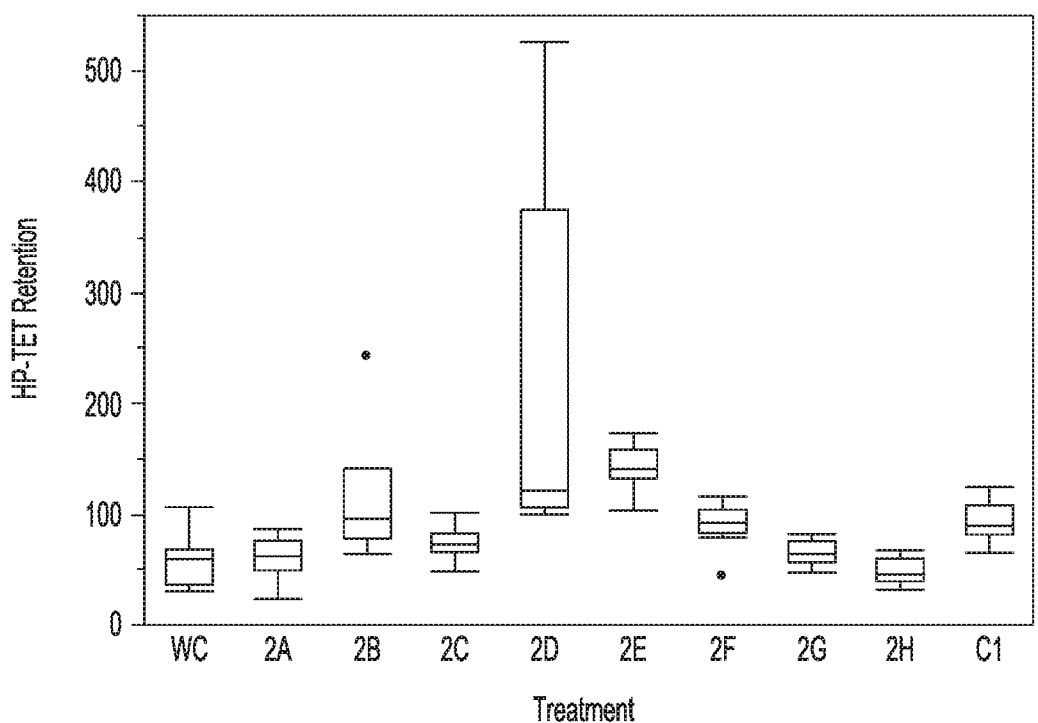
FIG. 8 is a plot depicting the HP-TET retention for flow cells having had an example of the protective coating thereon and for an uncoated control.

The example flow cells (two of each of 2A through 2H) included one lane defined on a tantalum oxide coated silicon substrate. A PAZAM layer was formed in the lane, and 1 µm primers were grafted on the PAZAM layer. Protective coatings were ultimately formed on the surface chemistry. As described below, two example flow cells were tested for each type of protective coating, and the results in FIG. 8 are the average for the two flow cells having the same type of protective coating. Some of the protective coatings were dried (2A through 2H) and one of the protective coatings was wet.

A comparative flow cell was tested. The surface chemistry was the same as the example flow cells. No protective coating was formed on the surface chemistry of the comparative flow cell.

A first HP-TET quality control assay was performed in each of the lanes of the example and comparative flow cells before the protective coatings were added to the example flow cells.

After the first HP-TET assay, several aqueous solutions of different potential protective coating materials were prepared. The solutions were prepared with ethylenediaminetetraacetic acid sodium salt (EDTA) (0.1 wt %), glycerol (1 wt %), hydroquinone (0.1 wt %), KOLLICOAT® IR (1%), polyethylene glycol 3000 (1%), (tris(2-carboxyethyl)phosphine) (TCEP) (0.1 wt %), Tris Base (pH 7-8) (100 mM), and TWEEN® 20 (a nonionic emulsifying agent) (1%).

A flow through process was used to introduce one of the aqueous solutions into two of the example flow cells (i.e., the EDTA solution was in two flow cells (collectively referred to as 2A), the glycerol solution was in another two flow cells (collectively referred to as 2B), the hydroquinone solution was in two more flow cells (collectively referred to as 2C), the KOLLICOAT® IR solution was in two other flow cells (collectively referred to as 2D), the polyethylene glycol 3000 solution was in two additional flow cells (collectively referred to as 2E), the TCEP solution was in two more flow cells (collectively referred to as 2F), the Tris Base solution was in still two more flow cells (collectively referred to as 2G), and the TWEEN® 20 solution was in two other flow cells (collectively referred to as 2H)), and onto the PAZAM layers and primers within the respective flow cells. The aqueous solutions were dried to form protective coatings. Drying of the example and comparative cells was performed using nitrogen gas.

The example flow cells were then dry stored for 3 days at 60° C. (equivalent to dry storage for 1 month at 25° C. or ambient conditions) with the protective coating in place.

The comparative uncoated flow cell (C1) was exposed to the same dry storage conditions.

Another protective coating was formed by introducing a liquid sodium chloride-sodium citrate (SSC) buffer using a flow through process. Thus, this example flow cell (WC) was exposed to wet storage conditions in which the sodium chloride-sodium citrate (SSC) buffer at 4° C. was left to soak on the flow cell surface chemistry.

After storage, the protective coating was removed from the lanes of the example flow cell via aqueous dissolution during washing, and the wet stored flow cell (WC) was rinsed out. Another HP-TET quality control assay was performed in each of the lanes of each of the example and comparative flow cells.

The HP-TET retention results were calculated using the before coating and after storage HP-TET results. The retention data are shown in FIG. 8. As depicted, the HP-TET retention for the flow cells with coatings of glycerol (2B), the copolymer (2D), the polyethylene glycol (2E), and the TCEP (2F) were comparable with or better than the dry stored comparative example (C1) stored at similar conditions. The results for coatings 2A, 2C, 2G and 2H indicate that these coatings, at these concentrations and/or applied by a flow through process, may hinder the accessibility of the primers and/or may not prevent degradation of the surface chemistry as well as the coatings 2B and 2D-2F. It is believed that the coatings 2A, 2C, 2G, and 2H may perform better at different concentrations and/or when applied by a different coating process.

Example 3

The flow cells used in this Example each included a non-patterned glass substrate with 4 lanes defined thereon. In one of the flow cells, two of the lanes (collectively referred to as 3A) were used as example lanes, and two of the lanes (collectively referred to C2A) were used as comparative example lanes. In another of the flow cells, two of the lanes (collectively referred to as 3B) were used as example lanes, and two of the lanes (collectively referred to C2B) were used as comparative example lanes. In a third of the flow cells, two of the lanes (collectively referred to as 3C) were used as example lanes, and two of the lanes (collectively referred to as C2C) were used as comparative example lanes.

A PAZAM layer was formed in each lane, and primers were grafted on the PAZAM layer. In the example lanes (3A, 3B, 3C), KOLLICOAT® IR protective coatings were formed on the surface chemistry using a flow through process. In the comparative example lanes (C2A, C2B, C2C), no protective coating was formed. Drying of the example lanes and the comparative example lanes was performed by flowing nitrogen gas through each lane for 30 seconds.

The flow cell with example flow lanes 3A and comparative flow lanes C2A were stored with 84% relative humidity in the packaging for 7 days and 14 days. The flow cell with example flow lanes 3B and comparative flow lanes C2B were stored with 5% relative humidity in the packaging for 7 days and 14 days.

These flow cells were removed from storage and were used for sequencing. The example lanes 3A, 3B and the comparative example lanes C2A, C2B were exposed to wash steps during sequencing. It is believed that washing at least partially removes the protective coating from the example lanes 3A, 3B. However, sequencing may also be performed without removing the protective coating.

Figure 9:
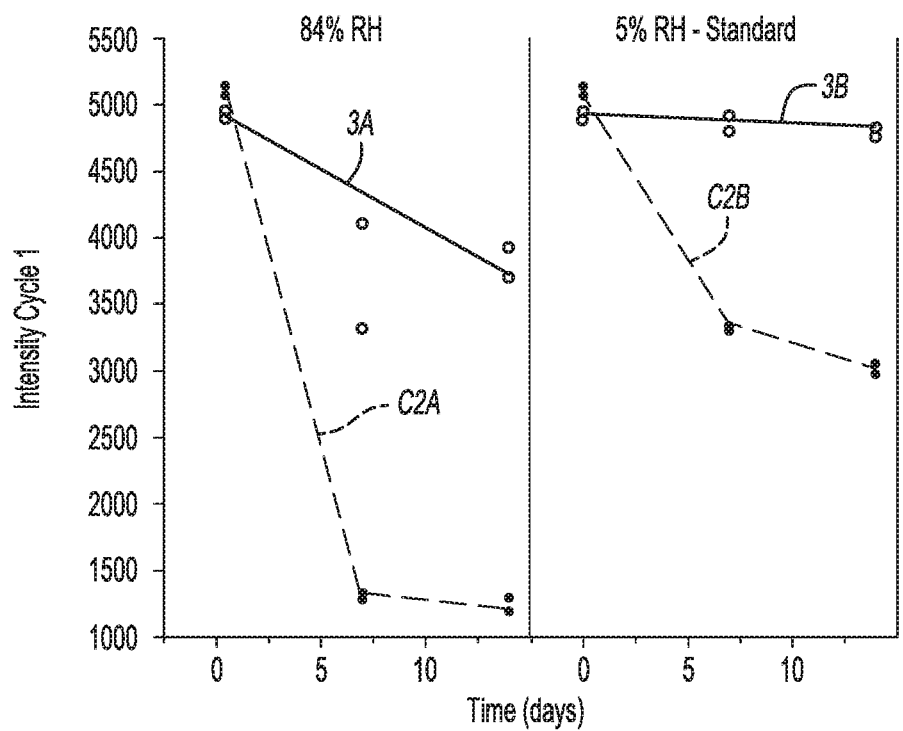
FIG. 9 is a plot of the fluorescence intensity after a first or initial sequencing cycle for flow cells with example flow lanes and comparative flow lanes packaged in different humidity conditions.

FIG. 9 shows a plot of the fluorescence intensity for the lanes (3A, 3B, C2A, C2B) after the first sequencing cycle. The data show that the cycle 1 intensities were minimally impacted by the humidity storage conditions when the protective coating was in place, compared to when the protective coating was not used (i.e., compare 3A with C2A and compare 3B with C2B). The cycle 1 intensities for the uncoated lanes C2A, C2B indicate that the surface chemistry decayed as a result of the humidity exposure. The effect on intensity of 5% humidity (flow lanes 3B) was also much less than the effect observed at 84% humidity (flow lanes 3A).

The flow cell with example flow lanes 3CA and comparative flow lanes C2C were stored under external temperature fluctuations for between 2 days and 19 days. The temperature profile ramp ranged from about −23° C. to about 60° C. during each 24 hour period over the respective time period. From hour 0 to about hour 8, the temperature was maintained between about −23° C. to −25° C. The temperature was then ramped up to about 60° C. and maintained for about 8 hours. The temperature was then ramped back down to between about −23° C. to −25° C., and from about hour 18 to hour 24, the temperature was maintained between about −23° C. to −25° C.

This flow cell was removed from storage and was used for sequencing. The example lanes 3C and the comparative example lanes C2C were exposed to wash steps during sequencing, and these steps are believed to at least partially remove the protective coating from the example lanes 3C (although sequencing can be performed before without protective coating removal).

Figure 10:
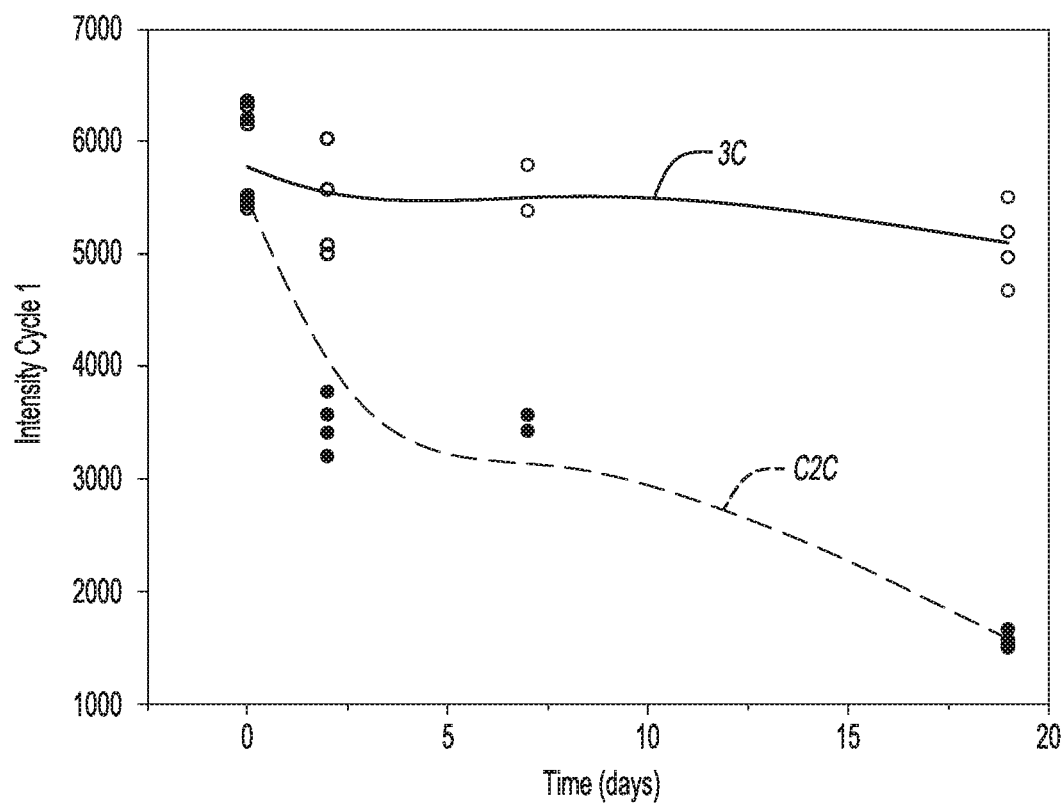
FIG. 10 is a plot of the fluorescence intensity after the first sequencing cycle for a flow cell with example flow lanes and comparative flow lanes exposed to a temperature ramp profile for different time periods ranging from 2 days to 19 days.

FIG. 10 shows a plot of the fluorescence intensity for the lanes (3C, C2C) after the first sequencing cycle. The data show that the cycle 1 intensity was minimally impacted by external temperature fluctuations when the protective coating was in place, compared to when the protective coating was not used (i.e., compare 3C with C2C. The cycle 1 intensity for the uncoated lanes C2C indicates that the surface chemistry decayed as a result of the external temperature fluctuations.

Example 4

Two open flow cells (i.e., no lids were attached) were used in this example. Each open flow cell included a single lane (4A, 4B) defined on a patterned silicon substrate, where each lane was in fluid communication with a plurality of wells. A PAZAM layer was formed in each well, and 1 µm primers were grafted on the PAZAM layer.

Prior to forming any protective coatings, the two open flow cells were exposed to sequencing.

KOLLICOAT® IR protective coatings were then formed on half of the surface chemistry of each open flow cell using a dip coating process. The open flow cells were dried in nitrogen gas. As such, in this example, the coated halves are referred to as examples 4A and 4B and the uncoated halves are referred to as comparative examples C3 and C4.

After the protective coatings were formed, the sample flow cell including coated side 4A and comparative uncoated side C3 was exposed to 6 days of open storage at 60° C. In open storage, the protective coating and the exposed surface chemistry of the uncoated side were directly exposed to the 60° C. temperature. The sample flow cell including coated side 4B and comparative uncoated side C4 was exposed to 7 days of open storage at room temperature.

The entire flow cells (i.e., previously coated halves 4A and 4B) and uncoated halves (C3 and C4) were removed from storage used for sequencing. The protective coatings were believed to be at least partially removed from the coated halves 4A and 4B via aqueous dissolution during washing step(s).

Figure 11A:
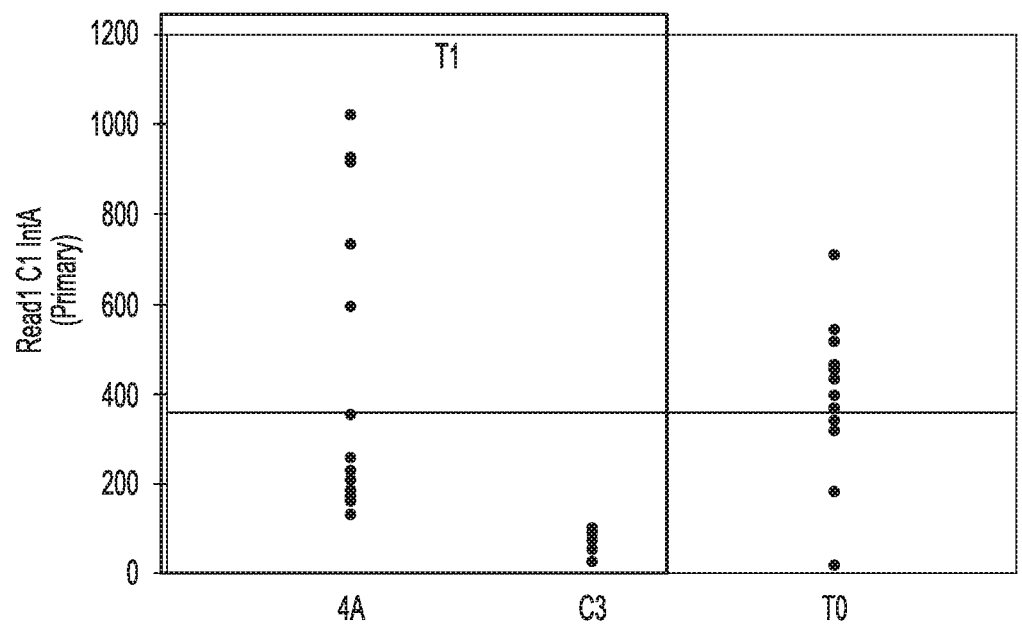
FIG. 11A is a plot of the read 1 (R1) fluorescence intensity after the first initial sequencing cycle (C1) for an example flow cell and a comparative flow cell aged at 60° C. for 6 days.

FIG. 11A shows a plot of the fluorescence intensity after the first sequencing cycle for the flow cell including 4A and C3 at time T0 (i.e., pre-coating on 4A) and after storage at time T1. The data show that the cycle 1 intensity was minimally impacted by the open storage at 60° C. when the protective coating was in place, compared to when the protective coating was not used (i.e., compare 4A with C3). The cycle 1 intensity for the uncoated half C3 indicates that the surface chemistry decayed as a result of the open storage.

Figure 11B:
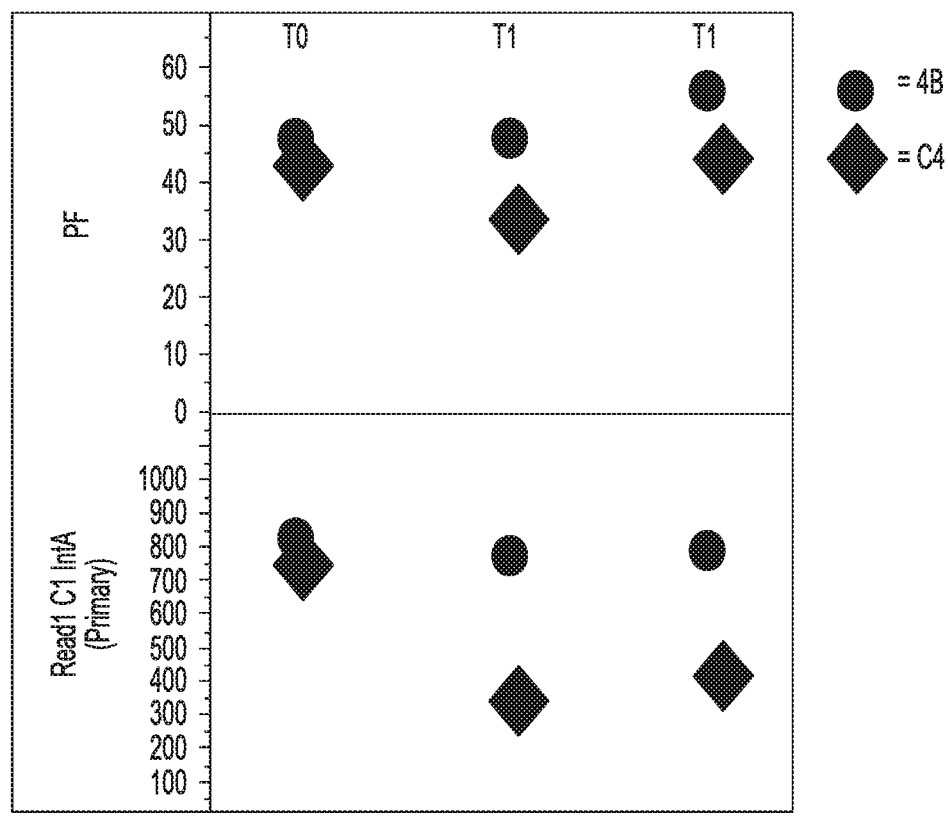
FIG. 11B includes a plot of the percentage of clusters passing filter (top) and a plot of the read 1 (R1) fluorescence intensity after the first sequencing cycle (C1) for an example flow cell and a comparative flow cell aged at room temperature for 7 days.

FIG. 11B shows two plots—the top illustrates the percentage of clusters passing through a filter (% passing filter (PF)) and the bottom illustrates the fluorescence intensity after the first sequencing cycle for the flow cell including 4B and C4 at time T0 (i.e., pre-coating on 4B) and two runs taken after storage at time T1. % Passing filter (PF) is the metric used to describe clusters which pass a chastity threshold and are used for further processing and analysis of sequencing data. Higher % passing filter result in increased yield of unique clusters used for sequencing data. The data in FIG. 11B shows that the % passing filter was improved when the protective coating was used (compare 4B to C4 at times T0 and both T1 data points). The data in FIG. 11B also shows that cycle 1 intensity was minimally impacted by the open storage at room temperature when the protective coating was in place, compared to when the protective coating was not used (i.e., compare 4B with C4 at times T0 and both T1 data points). The cycle 1 intensity for the uncoated half C4 indicates that the surface chemistry decayed as a result of the open storage, even at room temperature.

Example 5

An open patterned glass wafer had a PAZAM layer formed in each of its wells. After polishing, the wafer was diced, and a KOLLICOAT® IR protective coating was spray coated on one of the diced cells. A comparative diced cell was formed in a similar manner (with a PAZAM coating), except that the KOLLICOAT® IR protective coating was not formed.

The example and comparative diced cells were stored for 1 hour at 20° C., 60° C., and 80° C. After storage, the protective coating was removed from the example diced cell via aqueous dissolution during washing. 1 µm primers were then grafted on the PAZAM layers of the example and comparative diced cells to form, respectively an example flow cell and a comparative flow cell.

A CFR assay was performed to determine whether grafting of the primers was impacted by the different storage conditions. During a CFR assay, primer grafted surfaces are exposed to fluorescently tagged (Cal Fluor Red) complementary oligos in a buffer solution. These oligos bind to surface bound primers and excess CFR is washed off. The surface is then scanned in a fluorescent detector to measure CFR intensity on the surface to provide a quantitative measure of primers' concentration and health on the surface. After measurement, the oligos are removed with a mild base solution and surfaces are rescanned to confirm all CFR was removed.

Figure 12A:
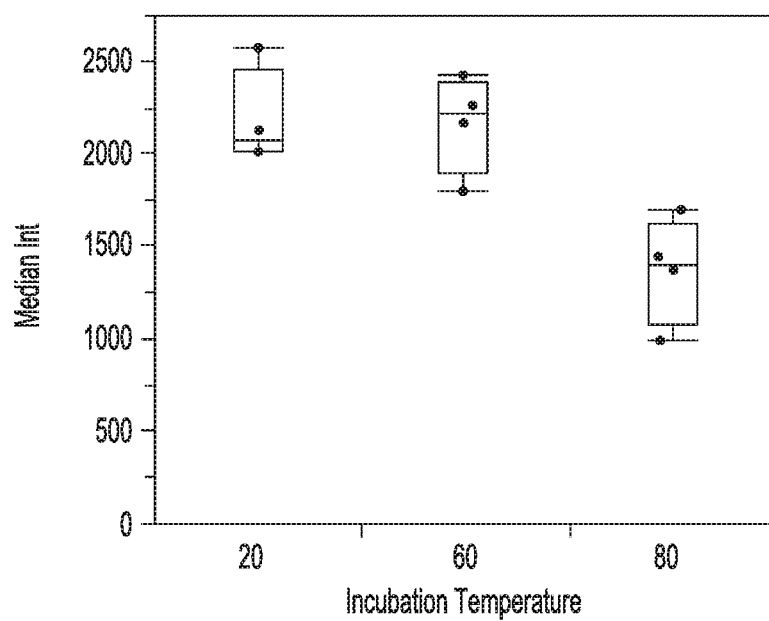
FIG. 12A is a plot of the median intensity for an example flow cell incubated at different temperatures for one hour.
Figure 12B:
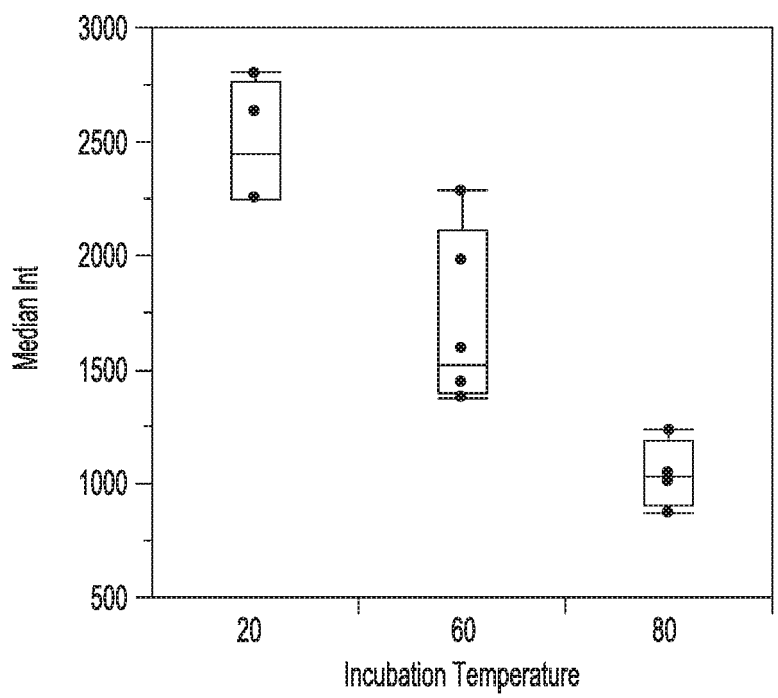
FIG. 12B is a plot of the median intensity for a comparative flow cell incubated at different temperatures for one hour.

The median intensity results for the example flow cell are shown in FIG. 12A and the median intensity results for the comparative flow cell are shown in FIG. 12B. Clearly, the ability of the uncoated PAZAM layer of the comparative flow cell to graft the primers was deleteriously affected at exposure to 60° C. or higher temperatures (FIG. 12B). The coated PAZAM layer of the example flow cell was able to graft the primers better at all tested temperatures than the uncoated PAZAM layer of the comparative diced cell (compare FIGS. 12A and 12B). While median intensity decreased for both the example and comparative flow cells at 80° C., the example flow cell seemed to degrade slower compared to the comparative flow cell.

Example 6

The flow cells used in this Example each included a non-patterned glass substrate with 4 lanes defined thereon. In each of the flow cells, two of the lanes were example lanes having the protective coating formed thereon, and two of the lanes were comparative lanes that did not have the protective coating formed thereon.

In each lane of each cell, a PAZAM layer was formed, and primers were grafted on the PAZAM layer using a flow through process. In each of the two example lanes of each flow cell, a KOLLICOAT® IR protective coating was formed on the surface chemistry using a flow through process. In each of the two comparative example lanes of each flow cell, the protecting coating was not formed. Drying of the example lanes and the comparative lanes was performed by flowing nitrogen gas through each lane for 30 seconds.

Each flow cell (including two example lanes and two comparative example lanes) was stored at a particular temperature, namely 25° C., 40° C., 60° C., or 80° C. The number of days for which the cells were stored varied from 1 day for up to 120 days.

The flow cells were removed from storage and were used for sequencing. The example lanes and the comparative example lanes were exposed to wash steps during sequencing, and these steps are believed to at least partially remove the protective coatings from the example lanes (although sequencing can be performed without such removal).

Figure 13:
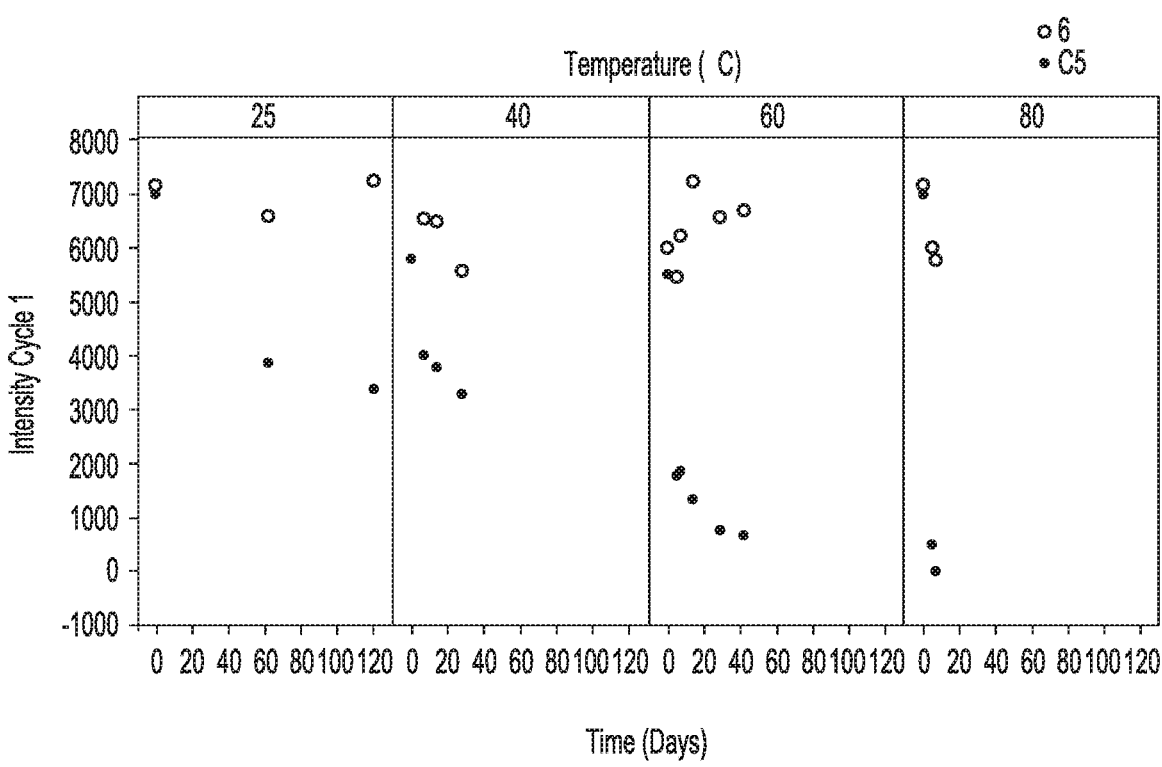
FIG. 13 is a plot of the read 1 (R1) fluorescence intensity after the first sequencing cycle for flow cells with example flow lanes and comparative flow lanes stored at different temperatures for different time periods.

FIG. 13 shows a plot of the average fluorescence intensity for the sets of lanes (example (i.e., 6) or comparative (i.e., C5)) after the first sequencing cycle. The intensity data is shown for example lanes and comparative example lanes, and the data is plotted by the temperature at which the cell was stored and the number of days for which the cell was stored. The data clearly show that the cycle 1 intensities were minimally impacted by the elevated temperature storage conditions when the protective coating was in place, regardless of the number of storage days, compared to when the protective coating was not used (i.e., compare data labeled "6" with comparative data labeled "C5". The cycle 1 intensities for the uncoated comparative example lanes indicate that the surface chemistry decayed as a result of the temperature exposure.

Example 7

Figure 14:
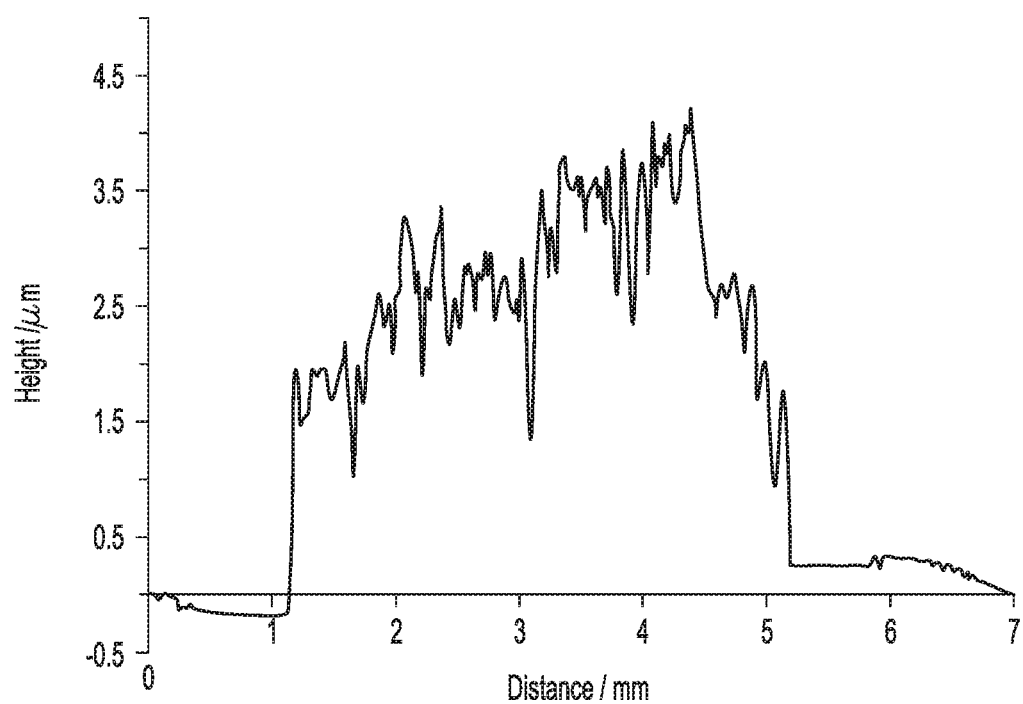
FIG. 14 is a graph depicting a distance across a protective coating on a patterned wafer in mm (x-axis) versus a distance of the coating thickness in μm (y-axis) (i.e., coating thickness (μm) as a function of distance across the wafer surface (mm))

KOLLICOAT® IR was spray coated onto a patterned CMOS wafer having a TaO$_x$ surface. The number of spray passes varied across the patterned CMOS wafer to determine the effect on the thickness of the resulting coating. The results are shown in FIG. 14 as the distance across the protective coating on the wafer in mm (x-axis) versus the distance of the protective coating thickness in μm (y-axis). The thickness of the copolymer coating increased slightly as the number of passes was increased across the wafer, and then decreased slightly as the number of passes was decreased. This data indicates that spray coating may be used to obtain a protective coating with a controlled thickness.

Example 8

An open patterned CMOS wafer had a PAZAM layer formed in each of its wells. After polishing, the wafer was diced to 700 nm cells, and a KOLLICOAT® IR protective coating was spray coated on three of the diced cells. Comparative diced cells were formed in a similar manner (with a PAZAM coating), except that the KOLLICOAT® IR protective coating was not formed.

One example diced cell and one comparative diced cell were stored for 28 days, or 35 days, or 71 days at room temperature (i.e., ~25° C.). After storage, the protective coatings were removed from the example diced cell via aqueous dissolution during washing. 1 μm primers were then grafted on the PAZAM layers of the example and comparative diced cells to form, respectively example flow cells (9A (28 day storage), 9B (35 day storage), 9C (71 day storage)) and comparative flow cells (C7A (28 day storage), C7B (35 day storage), C7C (71 day storage)).

Sequencing was then performed on each of the cells. The wash step(s) removed the protective coating from the example flow cells.

Figure 15:
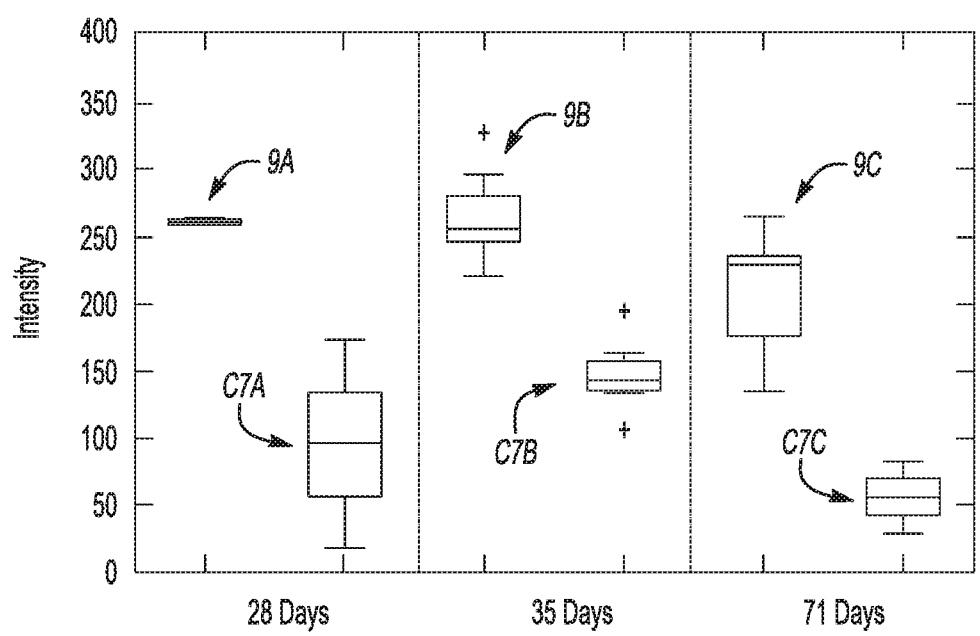
FIG. 15 is a plot of the fluorescence intensity after a surface primer accessibility test (CFR assay) for an example flow cell and a comparative flow cell after storage at room temperature for 28 days, 35 days, and 71 days.

FIG. 15 shows a plot of the fluorescence intensity after the first sequencing cycle. At each of the storage periods, the comparative flow cells C7A, C7B, C7C (stored without the protective coating) exhibited reduced intensity when compared to the example flow cells 9A, 9B, 9C (stored with the protective coating). The cycle 1 intensities for the uncoated flow cells C7A, C7B, C7C indicate that the surface chemistry decayed as a result of the exposure, even at room temperature.

Example 9

An open patterned silicon wafer had a PAZAM layer formed in each wells. After polishing, the wafer was diced to form cells, and an initial KOLLICOAT® IR protective coating was selectively spray coated on two of the diced cells, so that a bonding region remained exposed. Comparative diced cells were formed in a similar manner (with a PAZAM coating), except that the KOLLICOAT® IR protective coating was not formed. Lids were bonded to the respective bonding regions of the example and comparative diced cells to form flow cells. The initial KOLLICOAT® IR protective coatings were then removed from the PAZAM layers within the example flow cells via aqueous dissolution using a flow through process.

Primers were then grafted to each of the PAZAM layers within each of the example and comparative example flow cells using a flow through process.

After primer grafting, another KOLLICOAT® IR protective coating was formed on the primers and PAZAM layers within the example flow cells via a flow through process and drying.

The example flow cells (10A and 10B) were then dry stored for 2 weeks or 6 weeks at 30° C. with the protective coating in place. Two comparative uncoated flow cells (C8A, C8B) were exposed to the same dry storage conditions (2 week storage or 6 week storage at 30° C.), and the another example flow cell (WC2) was exposed to wet storage conditions for 6 weeks, during which sodium chloride-sodium citrate (SSC) buffer was left to soak at 4° C. on the flow cell surface chemistry.

After storage, sequencing was then performed on each of the cells. During washing step(s), the protective coating was believed to be at least partially removed from the example flow cells 10A, 10B, and the SSC buffer was rinsed from the wet stored flow cell WC2.

Figure 16:
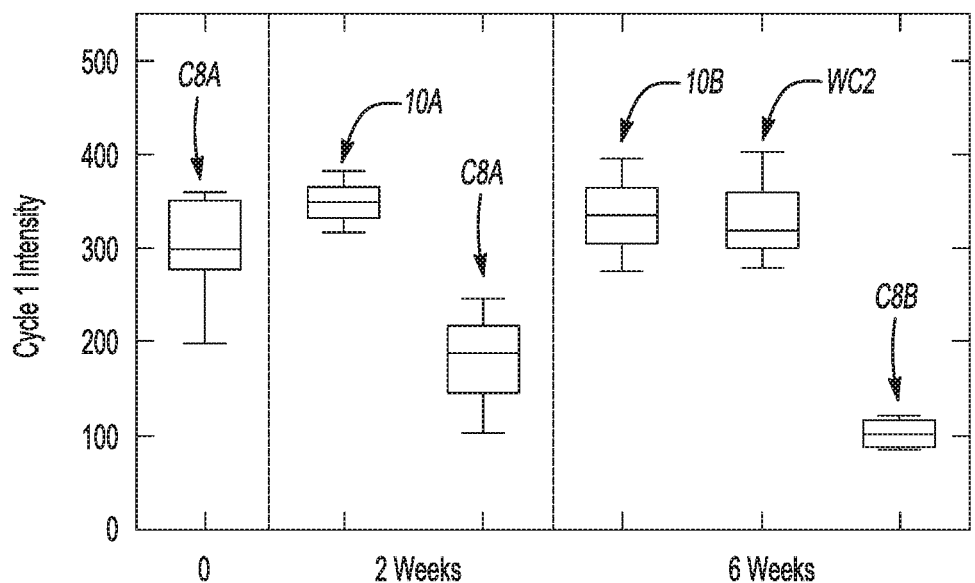
FIG. 16 is a plot of the fluorescence intensity after the first sequencing cycle for an example flow cell after dry storage at 30° C. for 0 weeks, 2 weeks, and 6 weeks, for a comparative flow cell after dry storage at 30° C. for 2 weeks and 6 weeks, and for an example flow cell after wet storage at 4° C. for 6 weeks.

FIG. 16 shows a plot of the fluorescence intensity after the first sequencing cycle. At each of the storage periods, the comparative flow cells C8A, C8B (stored at dry conditions without the protective coating) exhibited reduced intensity when compared to the example flow cells 10A, 10B (stored with the protective coating). At 6 weeks, the dry protective coating provided as good of protection for the surface chemistry as the wet storage protective coating (compare 10B with WC2).

Example 10

Open faced patterned tantalum oxide coated substrates had a PAZAM layer formed in each of the wells, and primers were grafted on the PAZAM layers using a flow through process. Comparative flow cells were also tested. The surface chemistry was the same as the example flow cells. No protective coatings were formed on the surface chemistry of the comparative flow cells.

A first CFR assay was performed prior to any protective coatings being formed on the example flow cells.

After the first CFR assay, several aqueous solutions of different potential protective coating materials were prepared. The solutions were prepared with ethylenediaminetetraacetic acid sodium salt (EDTA), polyethylene glycol, (tris(2-carboxyethyl)phosphine) (TCEP), tris(3-hydroxypropyltriazolylmethyl)amine (THPTA), tris(hydroxymethyl) aminomethane with EDTA (TE buffer), and bathophenanthrolinedisulfonic acid disodium salt (Bath). Each solution had a concentration as shown in Table 1. The aqueous solutions were applied by puddling the solutions on the surfaces of the example flow cells and the solutions were allowed to evaporate to form the coatings. The example flow cells were then dry stored for 11 days at 4° C. or at room temperature. Another example flow cell was a wet storage cell. The following Table 1 identifies the various cells tested and the conditions at which they were tested.

TABLE 1

| Identifier | Protective Coating | Storage Condition 4° C. | Room Temp. (RT) |
|---|---|---|---|
| WC3 | wet storage | yes | no |
| C11 (comparative example) | none | yes | no |
| 11A | 0.5M EDTA | yes | no |
| 11B | 4.4 wt % PEG | yes | no |
| 11C | 0.8 wt % TCEP | yes | no |
| 11D | 1.0 wt % THPTA | yes | no |
| 11E | 1x TE buffer | yes | no |
| C12 (comparative example) | none | no | yes |
| 11F | 1x TE buffer | no | yes |
| 11G | 1.6 wt % Bath | no | yes |
| 11H | 0.5M EDTA | no | yes |
| 11I | 4.4 wt % PEG | no | yes |
| 11J | 0.8 wt % TCEP | no | yes |
| 11K | 1.0 wt % THPTA | no | yes |

The comparative uncoated flow cell C11 and C12 exposed to the same dry storage conditions, respectively, as the example cells stored at dry 4° C. and at dry room temperature. The other flow cell WC3 was exposed to wet storage conditions in which sodium chloride-sodium citrate (SSC) buffer was left to soak at 4° C. on the flow cell surface chemistry.

After storage at the respective conditions, the protective coating was removed from each of the example flow cells (11A through 11K) via aqueous dissolution during washing, and the wet stored flow cell WC3 was rinsed out. Another CFR quality control assay was performed in each of the example and comparative flow cells.

Figure 17:
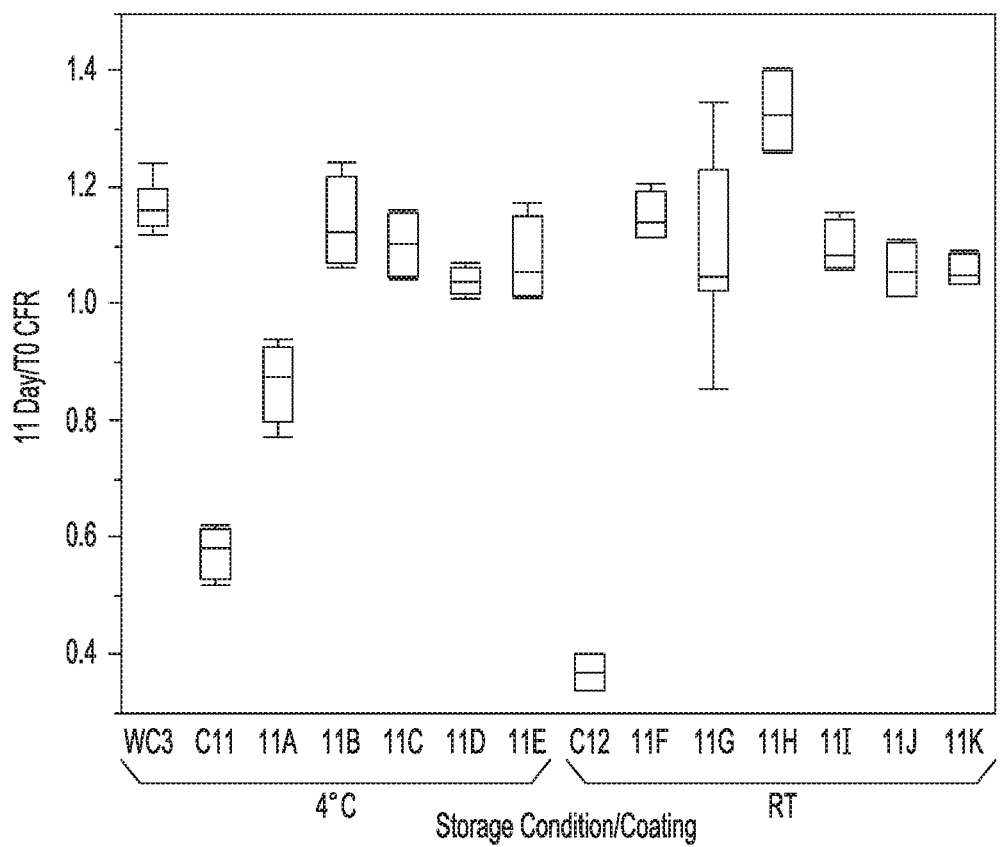
FIG. 17 is a plot depicting the results of a Cal Fluor Red (CFR) retention assay after 11 days of storage at different storage conditions, where CFR retention means the CFR signal at day 0 versus the CFR signal after storage.

The results shown in FIG. 17 are the 11 day CFR results divided by the T0 CFR results for each of the examples and comparative examples. As depicted, the CFR retention for the flow cells with each of the dry protective coatings were better than the dry stored comparative examples stored at similar conditions, and were on par with the wet storage conditions.

Example 11

Open faced patterned silicon substrates had a PAZAM layer formed in each of its wells. After polishing, 1 μm primers were then grafted on the PAZAM layers. A comparative example was formed in a similar manner.

Figure 18:
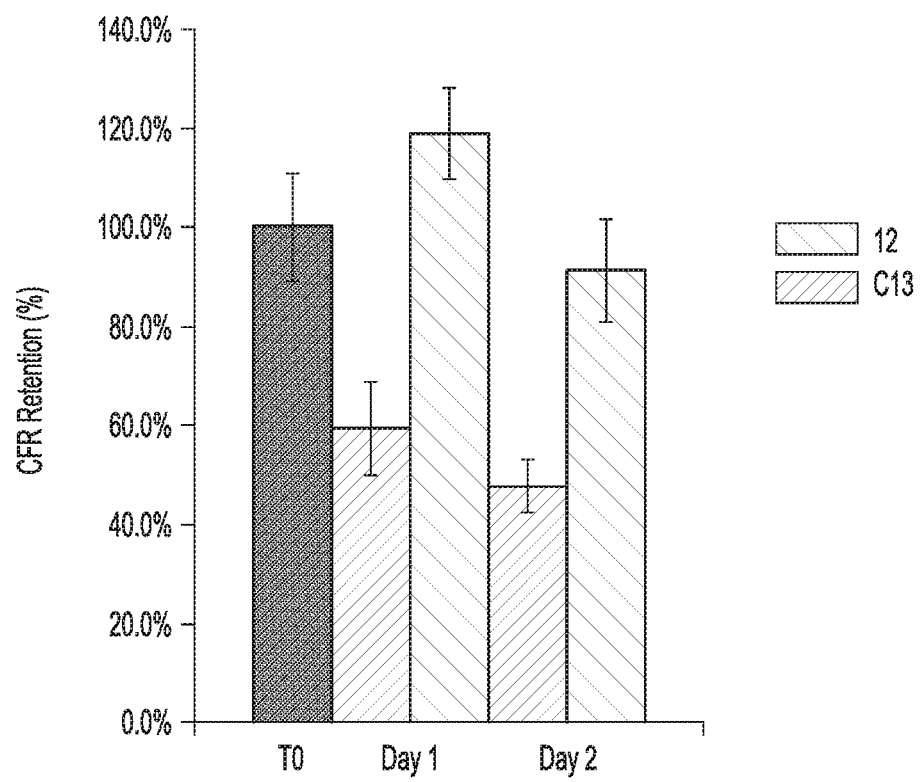
FIG. 18 is a bar graph depicting the CFR retention (%, ratio of CFR signal at day X/signal at day 0)) at time 0 (T0) and at day 1 and day 2 for an example flow cell and a comparative example flow cell.

A first CFR assay was performed prior to any protective coatings being formed on the example open faced flow cells. This data is shown in FIG. 18 as T0.

After the first CFR assay, an aqueous solution of KOLLICOAT® IR was prepared and used to form spray coated protective coatings on the example open faced cells.

The example open face flow cells were then dry stored for 1 day or 2 days at 60° C.

Sequencing was then performed on each of the open faced cells after their respective storage periods, and the protective coatings were removed during washing step(s).

FIG. 18 shows a bar graph of the CFR retention (%, ratio of the CFR signal at day X (X=1 or 2) divided by the signal at day 0) after the first sequencing cycle was performed following 1 storage day and 2 storage days. At each of the storage periods, the comparative flow cells C13 (stored without the protective coating) exhibited significantly reduced CFR retention when compared to the example flow cells 12 (stored with the protective coating). After one day of storage, the CFR of the comparative flow cell dropped 40%.

Example 12

A patterned CMOS wafer had a PAZAM layer formed in each of its wells. After polishing, KOLLICOAT® IR coatings of different thicknesses were spray coated on the patterned CMOS wafer and in respective wells (and the PAZAM layers therein) of the patterned CMOS wafer. The solution used to selectively spray the KOLLICOAT® IR coatings included about 5% KOLLICOAT® IR, about 5% ethanol, and about 90% water. The thicknesses of the various coatings ranged from 1.708 μm to 11.73 μm. Another portion of the wafer remained uncoated, and was used as a comparative example.

The wafer (including example portions and comparative example portion) was then dry stored at 40° C. for 2 days.

The respective coatings were removed from the wafer via aqueous dissolution, and primers were then dunk grafted on the PAZAM layers in the wells. A CFR assay was then performed.

Figure 19:
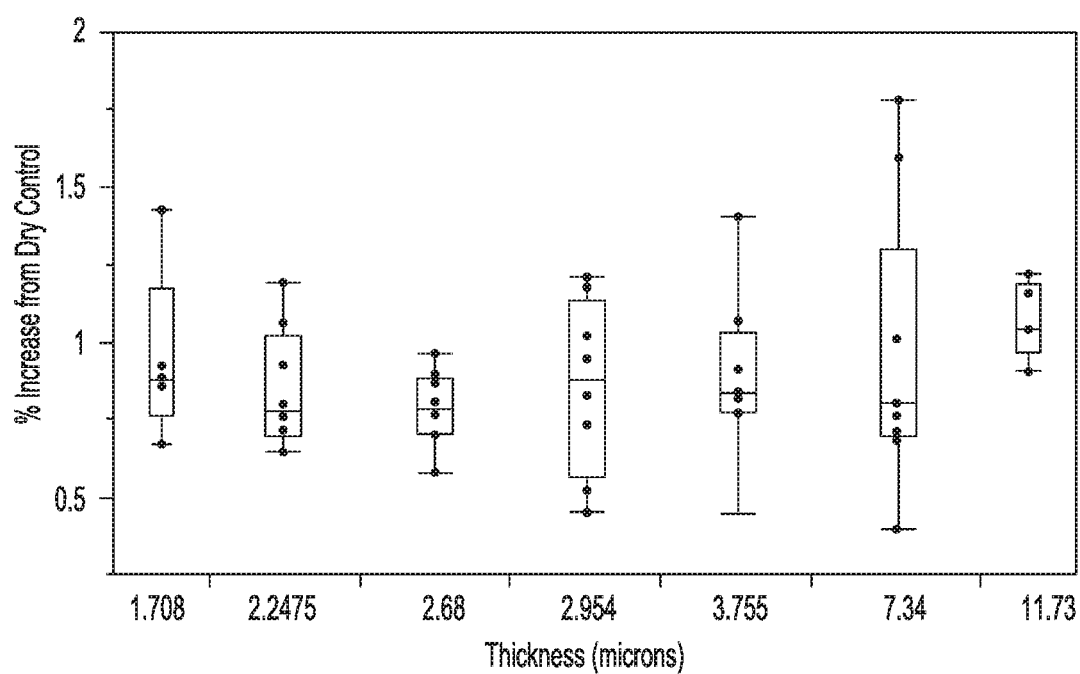
FIG. 19 is a plot of intensity percent increase for example flow cell portions compared to a dry control with respect to a thickness of the protective coating of respective example flow cell portions.

The % intensity increase, with respect to the comparative example portion, is shown for each of the example portions of the wafer that had been coated with a KOLLICOAT® IR coating. The results are shown in FIG. 19 and are labeled by the thickness of the KOLLICOAT® IR coating that has been used. The results indicate that the thickness of the protective coating does not seem to affect the functionality in preserving the performance of the PAZAM layer to graft primers after the protective coating is removed.

Example 13

The example flow cell included eight lanes defined on a patterned silicon substrate, where each lane was in fluid communication with a plurality of wells. A PAZAM layer was formed in each well, and 1 μm primers were grafted on the PAZAM layer.

Protective coatings were ultimately formed on the surface chemistry in four of the eight lanes. More particularly, four of the eight lanes were coated with a solution including about 5% KOLLICOAT® IR, about 5% ethanol, and about 90% water. The cell was dried using vacuum followed by 30 seconds of nitrogen gas exposure. The flowcell was stored for 2 days at 60° C.

The other four lanes were comparative flow lanes. The surface chemistry in the comparative flow lanes was the same as the example flow lanes, except that o protective coatings were formed on the surface chemistry of the comparative flow lanes.

After storage, sequencing was performed in each of the example flow lanes (collectively referred to as 13) and the comparative example flow lanes (collectively referred to as C14). The protective coating was removed using an aqueous wash as part of the sequencing.

Figure 20:
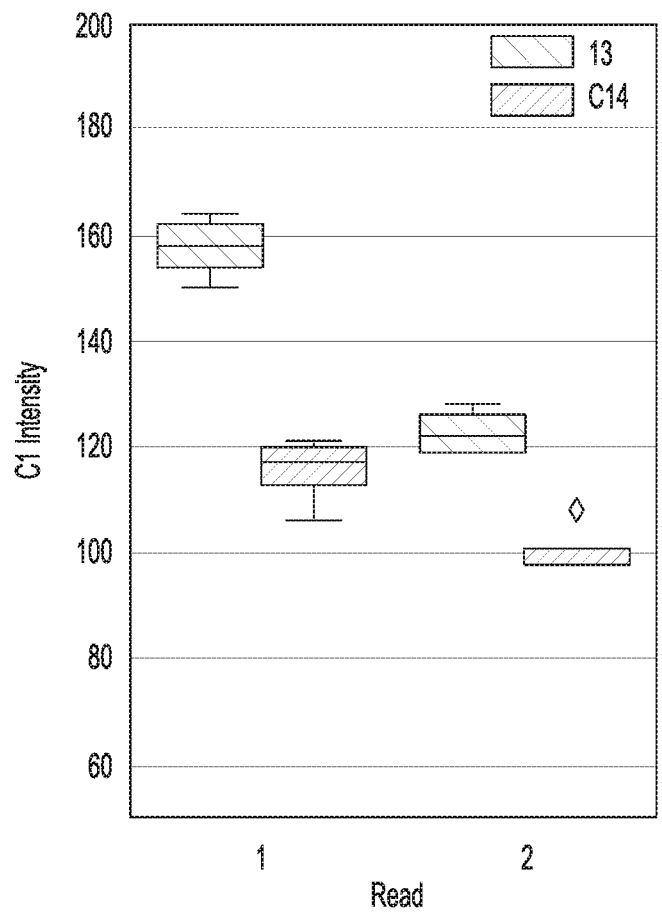
FIG. 20 is a plot of the fluorescence intensity of two reads after the first sequencing cycle (C1) for a flow cell including example lanes and comparative example lanes.

FIG. 20 shows a plot of the average fluorescence intensity for the example lanes (13) and the comparative example lanes (C14) for two reads after the first sequencing cycle. As depicted, the protective coating protected the example lanes of the flow cell against a significant decline in C1 intensity.

Example 14

The example flow cell included eight lanes defined on a patterned silicon substrate, where each lane was in fluid communication with a plurality of wells. A PAZAM layer was formed in each well, and 1 µm primers were grafted on the PAZAM layer.

A primer graft mix was prepared with varying amounts of KOLLICOAT® IR ranging from 5% to 0.1%, and was randomized among the eight lanes on the flow cell. This graft mix was allowed to incubate and then the cell was dried using vacuum followed by 30 seconds of nitrogen gas exposure in each hole/port.

The protective coatings were removed via aqueous dissolution, and a CFR assay was performed.

Figure 21:
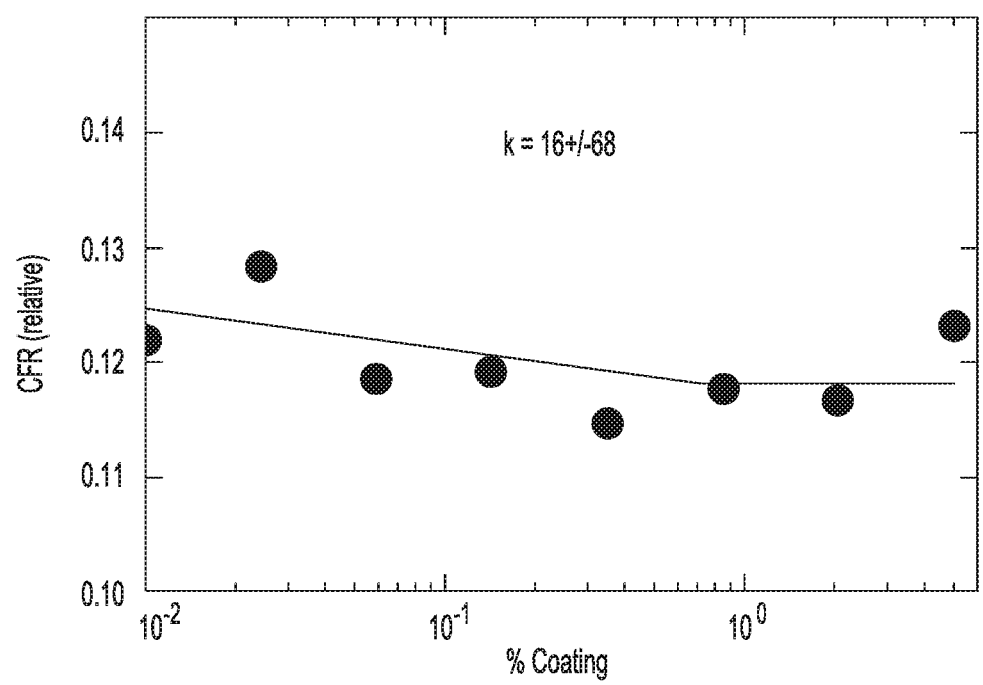
FIG. 21 is a graph of the CFR (relative signal) with respect to a percentage of the protective coating that was formed simultaneously with primer grafting.

FIG. 21 shows a plot of the relative CFR versus the percentage of KOLLICOAT® IR. The relatively consistent CFR data indicates that the primers may be grafted at the same time that the protective coating is deposited. This example provides evidence that the coating does not deleteriously affect the primer deposition chemistry used in this example.

Example 15

The three flow cells in this Example included eight lanes defined on a patterned silicon substrate, where each lane was in fluid communication with a plurality of wells. A PAZAM layer was formed in each well, and 1 µm primers were grafted on the PAZAM layer.

Polyacrylamide protective coatings were formed on the surface chemistry in one of the eight lanes. Comparative coatings (different water-soluble cationic polymers) were formed on the surface chemistry in five of the eight lanes, and one of the eight lanes was left uncoated. The comparative coatings were different cationic polymers. The following Table 2 identifies the various cells tested and the concentrations at which they were tested.

TABLE 2

| Identifier | Protective Coating | Concentration (%) | | |
|---|---|---|---|---|
| | | FC1 | FC2 | FC3 |
| No Coating (comparative example) | None | NA | NA | NA |
| 14 | Polyacrylamide | 0.01 | 0.1 | 1 |
| C15A (comparative example) | Luviquat ® HOLD | 0.01 | 0.1 | 1 |
| C15B (comparative example) | Luviquat ® FC 370 | 0.01 | 0.1 | 1 |
| C15C (comparative example) | Luviquat ® FC 550 | 0.01 | 0.1 | 1 |
| C15D (comparative example) | Polyquaternium-10 | 0.01 | 0.1 | 1 |
| C15E (comparative example) | Poly(ethylene imine) (PEI) | 0.01 | 0.1 | 1 |

The coatings were formed via a flow through process, and were dried using 30 seconds of nitrogen gas exposure. The cells were washed.

Figure 22:
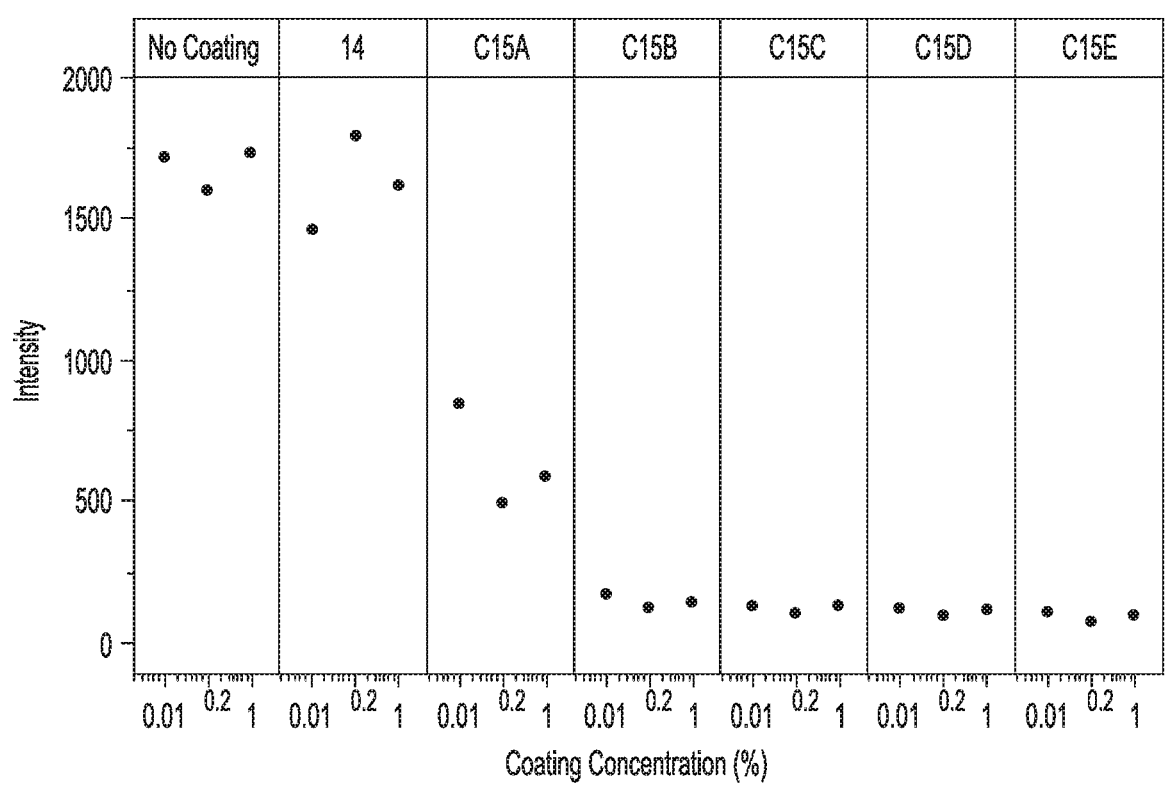
FIG. 22 is a graph of intensity (in arbitrary fluorescence units, AFU) versus concentration for an example protective coating and several comparative example protective coatings.

Clustering was performed in each of the flow cell lanes. A sequencing library was loaded into each flow lane, and fragments were captured by the complementary primers. Each fragment was amplified into distinct clonal clusters. The intensity was measured, and FIG. 22 illustrates the results as arbitrary fluorescence units, which quantifies the amount of double stranded DNA present on the flow cell lane surfaces. As depicted, the protective coating protected the example lane, while the cationic polymers hindered clustering (compare 14 to each of C15A through C15E). The cationic polymers were likely bound to the PAZAM and/or the primer surface chemistry.

ADDITIONAL NOTES

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range, as if the value(s) or sub-range(s) within the stated range were explicitly recited. For example, a range from about 200 mm to about 300 mm, should be interpreted to include not only the explicitly recited limits of from about 200 mm to about 300 mm, but also to include individual values, such as about 208 mm, about 245 mm, about 275.5 mm, etc., and sub-ranges, such as from about 225 mm to about 290 mm, from about 235 mm to about 280 mm, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A flow cell, comprising:
   a substrate including a bonding region at its periphery;
   a lid bonded to the bonding region of the substrate;
   a spacer layer positioned between the substrate and the lid so that the spacer layer contacts the bonding region, bonds the substrate and lid together, and forms sidewalls of the flow cell, wherein the lid and the substrate and the spacer layer define a flow channel between the substrate and the lid, and wherein the lid bonded to the substrate at the bonding region forms a boundary of the flow channel;
   an input port and an output port formed in the lid or the substrate;
   surface chemistry positioned on at least a portion of a surface of the substrate in the flow channel, the surface chemistry including:
      a functionalized polymer coating layer covalently bound to a chemical group on the surface; and
      a primer grafted to the functionalized polymer coating layer; and
   a water-soluble protective coating applied on the primer and the functionalized polymer coating layer.

2. The flow cell of claim 1, wherein the substrate is a patterned substrate comprising depressions separated by interstitial regions, and wherein a fluid introduced into the flow channel is introduced into the depressions.

3. The flow cell of claim 2, wherein the water-soluble protective coating is in the depressions and on at least a portion of the interstitial regions.

4. The flow cell of claim 1, wherein the substrate is a non-patterned substrate.

5. The flow cell of claim 1, wherein the water-soluble protective coating comprises: a non-cationic synthetic polymer; a natural polysaccharide or a derivative thereof; a natural protein or a derivative thereof; a water-soluble salt; or a small molecule compound selected from the group consisting of a water-soluble surfactant, a sugar, an antioxidant, a chelator, a buffer, a glycol, glycerol, and a cyclodextrin; or a combination thereof.

6. The flow cell of claim 1, wherein the water-soluble protective coating comprises a polyvinyl alcohol/polyethylene glycol graft copolymer, sucrose, dextran, a polyacrylamide, a glycol, tris(hydroxymethyl)aminomethane or a salt thereof, ethylenediaminetetraacetic acid or a salt thereof, (tris(2-carboxyethyl)phosphine), tris(3-hydroxypropyltriazolylmethyl)amine or a salt thereof, bathophenanthrolinedisulfonic acid disodium salt, a hydroxyl functional polymer, glycerol, or saline sodium citrate, or a mixture thereof.

7. The flow cell of claim 1, wherein the functionalized polymer coating layer is poly(N-(5-azidoacetamidylpentyl)acrylamide-co-acrylamide (PAZAM).

8. The flow cell of claim 7, wherein the surface of the substrate is silanized with a silane or silane derivative and wherein PAZAM is covalently attached to the silane or the silane derivative.

9. The flow cell of claim 8, wherein the silane or silane derivative is [(5-bicyclo[2.2.1]hept-2-enyl)ethyl]trimethoxysilane.

10. A method of using the flow cell of claim 1, comprising:
inserting the flow cell into a sequencing instrument; and
removing the water-soluble protective coating by exposing the water-soluble protective coating on the flow cell to water.

11. The method of claim 10, wherein the removing is done by performing a flow through process to remove the water-soluble protective coating.

* * * * *